(12) United States Patent
Thurieau et al.

(10) Patent No.: US 6,586,445 B1
(45) Date of Patent: Jul. 1, 2003

(54) β-CARBOLINE COMPOUNDS

(75) Inventors: Christophe Alain Thurieau, Paris (FR); Lydie Francine Poitout, Paris (FR); Marie-Odile Galcera, Bondoufle (FR); Christophe Philippe Moinet, Chatenay Malabry (FR); Thomas D. Gordon, Medway, MA (US); Barry A. Morgan, Franklin, MA (US); Dennis C. H. Bigg, Gif sur Yvette (FR); Jacques Pommier, Paris (FR)

(73) Assignee: Société de Conseils de Recherches et d'Applications Scientifiques, S.A.S., Paris (FR)

( * ) Notice: Subject to any disclaimer, the term of this patent is extended or adjusted under 35 U.S.C. 154(b) by 0 days.

(21) Appl. No.: 09/719,455
(22) PCT Filed: Jun. 8, 1999
(86) PCT No.: PCT/US99/12874
§ 371 (c)(1), (2), (4) Date: Jun. 13, 2001
(87) PCT Pub. No.: WO99/64420
PCT Pub. Date: Dec. 16, 1999

Related U.S. Application Data

(63) Continuation of application No. 09/097,297, filed on Jun. 12, 1998.
(60) Provisional application No. 60/089,180, filed on Jun. 12, 1998.
(51) Int. Cl.[7] .................. A61K 31/4165; A61K 31/407; C07D 471/02; C07D 233/54; C07D 403/02
(52) U.S. Cl. ................. 514/292; 514/397; 514/411; 546/85; 548/300.1; 548/311.7; 548/429
(58) Field of Search ................ 514/292, 411; 546/85; 548/300.1, 311.7, 429

(56) References Cited

U.S. PATENT DOCUMENTS 5,378,803 A * 1/1995 Morgan et al. ............. 530/317

OTHER PUBLICATIONS

Hirschmann, R. et al.; "De Novo Design and Synthesis of Somatostatin Non–Peptide Peptidomimetics Utilizing β–D–Glucose as a Novel Scaffolding"; J. Am. Chem. Soc. (1993) vol. 115; pgs. 12550–12568.

Yuichiro Yabe, et al.; "Synthesis and Biological Activity of Somatostatin Analogues modified at the Tryptophan Residue"; Chemical and Pharmaceutical Bulletin; vol. 26 No. 3 1978; pp. 993–997 XP002118335—Pharmaceutical Society of Japan Tokyo JP ISSN: 0009–23.

* cited by examiner

*Primary Examiner*—John M. Ford
*Assistant Examiner*—Sudhaker B. Patel
(74) *Attorney, Agent, or Firm*—Fish & Richardson; Brian R. Morrill; Alan F. Feeney

(57) ABSTRACT

The present invention is directed to compounds of the formula wherein the variables are defined in the specification, which bind to somatostatin receptors and block Na channels.

8 Claims, No Drawings

β-CARBOLINE COMPOUNDS

This application is a continuation of Ser. No. 09/097,297 filed Jun. 12, 1998 and claims benefit of Prov. No. 60/089, 180 filed Jun. 12, 1998.

BACKGROUND OF THE INVENTION

The present invention is directed to compounds of formulas (I) and (II) and compositions containing said compounds which bind selectively to somatostatin receptor subtypes and the use of said compounds for treating medical disorders which are mediated by somatostatin receptor subtypes. Somatostatin (somatotropin release inhibiting factor, SRIF), a tetradecapeptide hormone, originally isolated from bovine hypothalami (Brazeau, P. et al., Science 179, 77–79, 1973) has been shown to have a wide range of regulatory effects on the release of a variety of hormones such as growth hormone, prolactin, glucagon, insulin, gastrin (Bloom, S. R. and Poldack, J. M., Brit. Med. J. 295, 288–289, 1987). In addition, antiproliferative properties (Reichlin, S., N. Engl. J. Med. 309, 1495–1501, 1983) have been obtained with somatostatin analogs in metastatic prostatic cancer (Parmar, H. et al, Clin. Exp. Metastasis, 10, 3–11, 1992) and in several other neuroendocrine neoplasms in man (Anthony, L. et al, Acta Oncol., 32, 217–223, 1993). Metabolism of somatostatin by aminopeptidases and carboxypeptidases leads to a short duration of action.

The actions of somatostatin are mediated via membrane bound receptors. The heterogeneity of its biological functions has led to studies to identify structure-activity relationships of peptides analogs at the somatostatin receptors which resulted in the discovery of five receptor subtypes (Yamada, et al, Proc. Natl. Acad. Sci. U.S.A, 89, 251–255, 1992; Raynor, K. et al, Mol. Pharmacol., 44, 385–392, 1993). The functional roles of these receptors are under extensive investigation. Binding to the different types of somatostatin subtypes have been associated with the treatment of the following conditions and/or diseases. Activation of types 2 and 5 have been associated with growth hormone suppression and more particularly GH secreting adenomas (Acromegaly) and TSH secreting adenomas. Activation of type 2 but not type 5 has been associated with treating prolactin secreting adenomas. Other indications associated with activation of the somatostatin subtypes are restenosis, inhibition of insulin and/or glucagon and more particularly diabetes mellitus, hyperlipidemia, insulin insensitivity, Syndrome X, angiopathy, proliferative retinopathy, dawn phenomenon and Nephropathy; inhibition of gastric acid secretion and more particularly peptic ulcers, enterocutaneous and pancreaticocutaneous fistula, irritable bowel syndrome, Dumping syndrome, watery diarrhea syndrome, AIDS related diarrhea, chemotherapy-induced diarrhea, acute or chronic pancreatitis and gastrointestinal hormone secreting tumors; treatment of cancer such as hepatoma; inhibition of angiogenesis, treatment of inflammatory disorders such as arthritis; chronic allograft rejection; angioplasty; preventing graft vessel and gastrointestinal bleeding. Somatostatin agonists can also be used for decreasing body weight in a patient.

In drug research, it is a key issue to minimize side effects by developing highly potent and selective drug molecules. Recent work on the development of nonpeptide structures (Hirschmann, R. et al, J. Am. Chem. Soc. 115, 12550–12568, 1993; Papageorgiou, C. and Borer, X., Bioorg. Med. Chem. Lett. 6, 267–272, 1996) have described compounds with low somatostatin receptor affinity.

Further, compounds of Formula I and II are sodium channel blocker and, thus, exhibit useful pharmacological properties, especially utility for the alleviation of neuropathic pain. Neuropathic pain can be described as pain associated with damage or permanent alteration of the peripheral or central nervous system. Clinical manifestations of neuropathic pain include a sensation of burning or electric shock, feelings of bodily distortion, allodynia and hyperpathia.

Sodium channel-blocking agents have been reported to be effective in the treatment of various disease states. They are in particular useful as local anesthetics, and in the treatment of arrhythmia. It has also been reported for many years that sodium channel-blocking agents may be useful in the treatment of pain, including neuropathic pain; see, for example, Tanelian et al., Pain Forum., 4(2), 75–80, (1995). There is evidence that sodium channel-blocking agents selectively suppress ectopic neural firing in injured nerves, and it is via this mechanism that they are believed to be useful for relieving pain. However, studies carried out on well known sodium channel-blocking agents, for example carbamazepine, phenytoin, lidocaine, mexiletine, and the like, indicate that these agents are not very effective for the treatment of neuropathic pain conditions at moderate dose levels, and that even at these moderate dose levels they are associated with a range of undesirable side effects, such as vertigo, nausea, sommolence, tremor, slurred speech, etc. Pre-clinical evidence demonstrates that sodium channel-blocking agents selectively suppress abnormal ectopic neural firing in injured peripheral and central neurons, and it is via this mechanism that they are believed to be useful for relieving pain. Consistent with this hypothesis, it has been shown that sodium channel accumulate in the peripheral nerve at sites of axonal injury (Devor et al., J. Neurosci, 1993, 132, 1976–1992). Alterations in either the level of expression or distribution of sodium channels with an injured nerve, therefore, have a major influence on the pathophysiology of pain associated with this type of trauma. This concept is supported by the relative success of employing sodium channel modulating agents (e.g., anticonvulsants, local anesthesics) for the treatment of neuroplastic pain. However, pain relief has often been obtained concomitantly with numerous adverse events and/or limitations in efficacy which have restricted tolerability of these drugs. It can be seen that a need still exists for an orally active agent that is effective for the treatment of neuropathic pain, but having fewer side effects.

Another aspect of this invention relates to the use of a compound of Formula I or II for treating neuropathic pain conditions in a mammal that is responsive to sodium channel-blocking agents including: peripheral neuropathies, such as trigeminal neuralgia, postherapeutic neuralgia, radiculopathy, and neuropathy secondary to metastatic infiltration, adiposis dolorosa and burn pain; and central pain conditions following stroke, thalamic lesions and multiple sclerosis, by administering a therapeutically effective amount of a compound of Formula I or II to the mammal.

As a result, the compounds of the invention are indicated for the treatment of any pathology, disorder or clinical condition involving glutamate release in their etiology, including psychiatric disorders (such as schizophrenia, depression, anxiety, panic attacks, attention deficit and cognitive disorders, social withdrawal), hormonal conditions (excess GH, e.g. in the treatment of diabetes mellitus, angiopathy and acromegaly, or LH secretion, e.g., prostrate hypertrophy, menopausal syndrome, corticosterone secretion in stress), metabolic inducted brain damage (hypoglycaemia, non-ketotic hyperglycinaemia (glycine encephalopathy), sulphite oxidase deficiency, hepatic encephalopathy associated with liver failure), emesis, spasticity, epilepsy, tinnitus, pain (e.g. cancer pain, arthritis) and drug (ethanol, opiates, including synthetics with opiate-like effects, e.g. pethidine, methadone etc., cocaine, amphetamine, barbiturates and other sedatives, benzodiazephines, abuse and withdrawal.

Moreover, a compound of the present invention is indicated in the treatment of any pathology involving neuronal damage, for example neurodegenerative disorders such as Alzheimer's, Huntington's or Parkinson's diseases, virus (including HIV)-induced neurodegeneration, Amyotrophic lateral sclerosis (ALS), supra-nuclear palsy, olivoponto-cerebellar atrophy (OPCA), and the actions of environmental, exogenous neurotoxins.

SUMMARY OF THE INVENTION

In one aspect, the present invention is directed to a compound of formula (I),

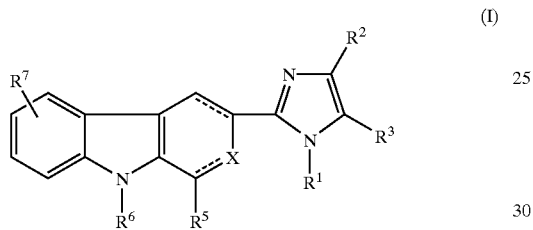

the racemic-diastereomeric mixtures and optical isomers of said compound of formula (I), the pharmaceutically-acceptable salts or prodrugs thereof or a pharmaceutically acceptable salt of said prodrug,
wherein
- - - represents an optional bond;
X is N or N—$R^4$, where X is N when both optional bonds are present and X is N—$R^4$ when the optional bonds are not present;
$R^1$ is H, —$(CH_2)_m$—C(O)—$(CH_2)_m$—$Z^1$, —$(CH_2)_m$—$Z^1$, —$(CH_2)_m$—O—$Z^1$ or $(C_0$–$C_6)$alkyl-C(O)—NH—$(CH_2)_m$—$Z^3$;
$Z^1$ is an optionally substituted moiety selected from the group consisting of $(C_1$–$C_{12})$alkyl, benzo[b]thiophene, phenyl, naphthyl, benzo[b]furanyl, thiophene, isoxazolyl, indolyl,

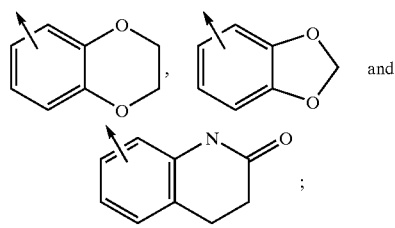

$R^2$ is $(C_1$–$C_{12})$alkyl, $(C_0$–$C_6)$alkyl-C(O)—O—$Z^5$, $(C_0$–$C_6)$alkyl-C(O)—NH—$(CH_2)_m$—$Z^3$ or optionally substituted phenyl;
$Z^5$ is H, $(C_1$–$C_{12})$alkyl or $(CH_2)_m$-aryl;
$Z^3$ is amino, $(C_1$–$C_{12})$alkylamino, N,N-di-$(C_1$–$C_{12})$alkylamino, —NH—C(O)—O—$(CH_2)_m$-phenyl, —NH—C(O)—O—$(CH_2)_m$—$(C_1$–$C_6)$alkyl or an optionally substituted moiety selected from the group consisting of imidazolyl, pyridinyl and morpholinyl, piperidinyl, piperazinyl, pyrazolidinyl, furanyl and thiophene;
$R^3$ is H;
$R^4$ is H, —C(=Y)—N($X^1X^2$), C(=O)$X^2$ or $X^2$;
Y is O or S;
$X^2$ is —$(CH_2)_m$—$Y^1$—$X^3$;
$X^3$ is H or an optionally substituted moiety selected from the group consisting of $(C_1$–$C_{12})$alkyl, $(C_3$–$C_8)$ cycloalkyl, $(C_1$–$C_{12})$alkoxy, aryloxy, $(C_1$–$C_{12})$ alkylamino, N,N-di-$(C_1$–$C_{12})$alkylamino, —CH—di-$(C_1$–$C_{12})$alkoxy or phenyl;
$R^5$ is $(C_1$–$C_{12})$alkyl, —$(CH_2)_m$—$Y^1$—$(CH_2)_m$-phenyl-$(X^1)_n$, $(C_3$–$C_{12})$cycloalkyl, —$(CH_2)_m$—S—$(C_1$–$C_{12})$ alkyl, $(C_1$–$C_{12})$alkyl-S—S—$(C_1$–$C_{12})$alkyl, —$(CH_2)_m$—$(C_1$–$C_{12})$alkenyl or an optionally substituted moiety selected from the group consisting of phenyl, furanyl, thiophene, pyrrolyl, pyridinyl and

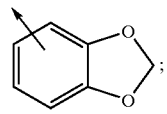

$Y^1$ is O, S, NH or a bond;
$R^6$ is H or $SO_2$-phenyl;
$R^7$ is H, alkyl optionally substituted with alkoxy or dialkylamino;
wherein an optionally substituted moiety or optionally substituted phenyl is optionally substituted by one or more substituents, each independently selected from the group consisting of Cl, F, Br, I, $CF_3$, $NO_2$, OH, $SO_2NH_2$, CN, $N_3$, —$OCF_3$, $(C_1$–$C_{12})$alkoxy, —$(CH_2)_m$-phenyl-$(X^1)_n$, —NH—CO—$(C_1$–$C_6)$alkyl, —S-phenyl-$(X^1)_n$, —O—$(CH_2)_m$-phenyl-$(X^1)_n$, —$(CH_2)_m$—C(O)—O—$(C_1$–$C_6)$ alkyl, —$(CH_2)_m$—C(O)—$(C_1$–$C_6)$alkyl, —O—$(CH_2)_m$—$NH_2$, —O—$(CH_2)_m$—NH—$(C_1$–$C_6)$alkyl, —O—$(CH_2)_m$—N-di-$((C_1$–$C_6)$alkyl) and —$(C_0$–$C_{12})$alkyl-$(X^1)_n$;
$X^1$ for each occurrence is independently selected from the group consisting of hydrogen, Cl, F, Br, I, $NO_2$, OH, —$CF_3$, —$OCF_3$, $(C_1$–$C_{12})$alkyl, $(C_1$–$C_{12})$alkoxy, —S—$(C_1$–$C_6)$alkyl, —$(CH_2)_m$-amino, —$(CH_2)_m$—NH—$(C_1$–$C_6)$alkyl, —$(CH_2)_m$—N—di-$((C_1$–$C_6)$ alkyl), —$(CH_2)_m$-phenyl and —$(CH_2)_m$—NH—$(C_3$–$C_6)$cycloalkyl;
m for each occurrence is independently 0 or an integer from 1 to 6; and
n for each occurrence is independently an integer from 1 to 5.
A preferred compound of formula (I) is where X is NH; $R^1$ is H; $R^2$ is —$CH(CH_3)_2$—CO—NH—$(CH_2)_m$—$Z^3$ where m in the definition of $R^2$ is 1, 2 or 3;
$Z^3$ is imidazolyl, pyridinyl, morpholino, or N,N-diethylamino;
$R^5$ is propyl, n-butyl, n-pentyl, —$(CH_2)$—O—$(CH_2)$-phenyl, 2-nitro-3-OMe-phenyl, p-t-Bu-phenyl, m-OMe-phenyl, o-OMe-phenyl, p-nitro-phenyl, —$(CH_2)_2$—S—Me, cyclohexyl, m-Br-phenyl, p-S-Me-phenyl, p-N,N-dimethylamino-phenyl, m-methyl-phenyl or

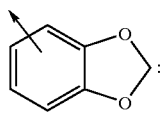

R[6] is H; and R[7] is H.

Another preferred compound of formula (I) is where X is NH; R[1] is H; R[2] is phenyl;

R[5] is propyl, n-butyl, n-pentyl, n-heptyl, isobutyl, neopentyl, cyclopropyl, cyclohexyl, —(CH$_2$)$_2$—S—Me, phenyl, —(CH$_2$)—O—(CH$_2$)-phenyl, 2-nitro-3-OMe-phenyl, p-t-Bu-phenyl, o-OMe-phenyl, m-OMe-phenyl, p-OMe-phenyl, 3,4,5-tri-OMe-phenyl, p-butoxy-phenyl, 3-ethoxy4-methoxy-phenyl, o-nitro-phenyl, p-nitro-phenyl, p-OCF$_3$-phenyl, o-CF$_3$-phenyl, 3-F-4-OMe-phenyl, o-F-phenyl, o-Br-phenyl, m-Br-phenyl, p-Br-phenyl, 2,4-di-Cl-phenyl, 3,4-di-Cl-phenyl, p-(3-(N,N-dimethylamino)propoxy)phenyl, —(CH$_2$)$_2$—S—Me, cyclohexyl, p-(Me-CO-NH-)-phenyl, p-t-Bu-phenyl, p-OH-phenyl, p-(-S-Me)-phenyl, p(-S-t-Bu)-phenyl, p-N,N-dimethylamino-phenyl, m-methyl-phenyl, 3-OH-4-Ome-phenyl, p-phenyl-phenyl,

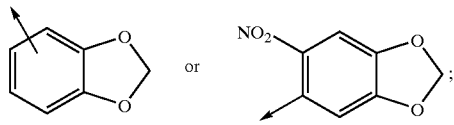

R[6] is H; and R[7] is H.

Another preferred compound of formula (I) is where X is NH; R[1] is H; R[2] is p-OMe-phenyl or p-nitro-phenyl;

R[5] is n-butyl, n-pentyl, n-hexyl, isobutyl, cyclohexyl, —(CH$_2$)$_2$—S—Me, phenyl, m-OMe-phenyl, 2-nitro-3-OMe-phenyl, p-nitro-phenyl, p-t-Bu-phenyl, p-thiomethyl-phenyl, m-Br-phenyl, 2-OMe-4-dimethylamino-phenyl, p-(3-(N,N-dimethylamino) propoxy)phenyl, p-dimethylamino-phenyl, 3-nitro4-Cl-phenyl, —(CH$_2$)—O—(CH$_2$)-phenyl or

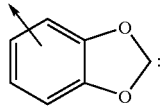

R[6] is H; and R[7] is H.

In another aspect, the present invention is directed to a compound of formula (II),

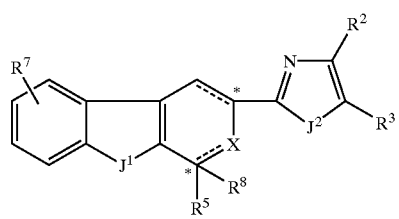

(II)

the racemic-diastereomeric mixtures and optical isomers of said compound of formula (II), the pharmaceutically-acceptable salts or prodrugs thereof or a pharmaceutically acceptable salt of said prodrug, wherein

- - - represents an optional bond;

J[1] is N—R[6] or S;

J[2] is N—R[1], O or S;

X is N or N—R[4], where X is N when both optional bonds are present and X is N—R[4] when the optional bonds are not present;

R[1] is H, —(CH$_2$)$_m$—C(O)—(CH$_2$)$_m$—Z[1], —(CH$_2$)$_m$—Z[1], —(CH$_2$)$_m$—O—Z[1] or (C$_0$–C$_6$)alkyl-C(O)—NH—(CH$_2$)$_m$—Z[3];

Z[1] is an optionally substituted moiety selected from the group consisting of (C$_1$–C$_{12}$)alkyl, benzo[b] thiophene, phenyl, naphthyl, benzo[b]furanyl, thiophene, isoxazolyl, indolyl,

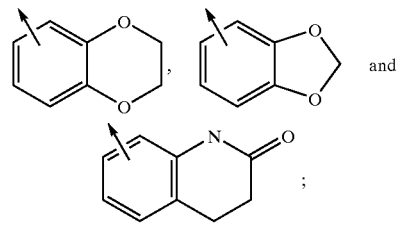 and

R[2] is (C$_1$–C$_{12}$)alkyl, (C$_0$–C$_6$)alkyl-C(O)—O—Z[5], (C$_0$–C$_6$)alkyl-C(O)—NH—(CH$_2$)$_m$—Z[3] or optionally substituted phenyl;

Z[5] is H, (C$_1$–C$_{12}$)alkyl or (CH$_2$)$_m$-aryl;

Z[3] is amino, (C$_1$–C$_{12}$)alkylamino, N,N-di-(C$_1$–C$_{12}$) alkylamino, —NH—C(O)—O—(CH$_2$)$_m$-phenyl, —NH—C(O)—O—(CH$_2$)$_m$—(C$_1$–C$_6$)alkyl or an optionally substituted moiety selected from the group consisting of phenyl, imidazolyl, pyridinyl and morpholinyl, piperidinyl, piperazinyl, pyrazolidinyl, furanyl and thiophene;

R[3] is H, (C$_1$–C$_6$)alkyl or optionally substituted phenyl;

R[4] is H, —C(=Y)—N(X[1]X[2]), C(=O)X[2] or X[2];

Y is O or S;

X[2] is H or —(CH$_2$)$_m$—Y[1]—X[3];

X[3] is H or an optionally substituted moiety selected from the group consisting of (C$_1$–C$_{12}$)alkyl, (C$_3$–C$_8$) cycloalkyl, (C$_1$–C$_{12}$)alkoxy, aryloxy, (C$_1$–C$_{12}$) alkylamino, N,N-di-(C$_1$–C$_{12}$)alkylamino, —CH—di-(C$_1$–C$_{12}$)alkoxy or phenyl;

R[5] and R[8] are each independently selected from the group consisting of H, (C$_1$–C$_{12}$)alkyl, —(CH$_2$)$_m$—Y[1]—(CH$_2$)$_m$-phenyl-(X[1])$_n$, (C$_3$–C$_{12}$)cycloalkyl, (C$_3$–C$_{12}$) cycloalkenyl, —(CH$_2$)$_m$—S—(C$_1$–C$_{12}$)alkyl, (C$_1$–C$_{12}$) alkyl-S—S—(C$_1$–C$_{12}$)alkyl, —(CH$_2$)$_m$—(C$_1$–C$_{12}$) alkenyl and an optionally substituted moiety selected from the group consisting of phenyl, furanyl, thiophene, pyrrolyl, pyridinyl and

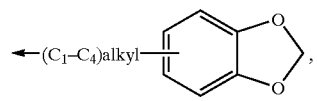

provided that R[5] and R[8] are not both H at the same time;

or R[5] and R[8] are taken together with the carbon atom to which they are attached to form

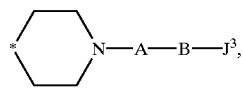

spiro($C_4$-$C_{12}$)cycloalkyl,

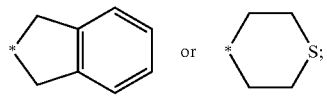

$Y^1$ is O, S, NH or a bond;

A is a bond, —CO—, —C(O)O—, —C(O)NH—, —C(S)NH—, or —$SO_2$—;

B is a bond or —$(CH_2)_q$—, where q is an integer from 1 to 6;

$J^3$ is H, ($C_1$-$C_6$)alkyl, optionally substituted phenyl, optionally substituted heteroaryl or N($R^9R^{10}$), where $R^9$ and $R^{10}$ are each independently selected from the group consisting of ($C_1$-$C_6$)alkyl, and optionally substituted phenyl, or $R^9$ and $R^{10}$ are taken together with the nitrogen to which they are attached to form a ring having 5 to 8 members including the nitrogen atom that $R^9$ and $R^{10}$ are attached to, where one of the ring members may optionally be an oxygen atom or $NR^{11}$, where $R^{11}$ is ($C_1$-$C_6$)alkyl, —C(O)—($C_1$-$C_6$)alkyl, —C(O)—N($V^1V^2$), —C(S)—N($V^1V^2$), or optionally-substituted-phenyl-($C_0$-$C_6$)alkyl-, where $V^1$ and $V^2$ are each independently H, ($C_1$-$C_6$)alkyl or optionally-substituted-phenyl-($C_0$-$C_6$)alkyl;

$R^6$ is H or $SO_2$-phenyl;

$R^7$ is H, Cl, F, Br, I, $CF_3$, $NO_2$, OH, $SO_2NH_2$, CN, $N_3$, —$OCF_3$, ($C_1$-$C_{12}$)alkoxy, —$(CH_2)_m$-phenyl-$(X^1)_n$, —NH—CO—($C_1$-$C_6$)alkyl, —S—($C_1$-$C_{12}$)alkyl, —S-phenyl-$(X^1)_n$, —O—$(CH_2)_m$-phenyl-$(X^1)_n$, —$(CH_2)_m$—C(O)—O—($C_1$-$C_6$)alkyl, —$(CH_2)_m$—C(O)—($C_1$-$C_6$)alkyl, —O—$(CH_2)_m$—$NH_2$, —O—$(CH_2)_m$—NH—($C_1$-$C_6$)alkyl, —O—$(CH_2)_m$—N—di-(($C_1$-$C_6$)alkyl) and —($C_0$-$C_{12}$)alkyl-$(X^1)_n$;

wherein an optionally substituted moiety or optionally substituted phenyl is optionally substituted by one or more substituents, each independently selected from the group consisting of Cl, F, Br, I, $CF_3$, $NO_2$, OH, $SO_2NH_2$, CN, $N_3$, —$OCF_3$, ($C_1$-$C_{12}$)alkoxy, —$(CH_2)_m$-phenyl-$(X^1)_n$, —NH—CO—($C_1$-$C_6$)alkyl, —S—($C_1$-$C_{12}$)alkyl, —S-phenyl-$(X^1)_n$, —O—$(CH_2)_m$-phenyl-$(X^1)_n$, —$(CH_2)_m$—C(O)—O—($C_1$-$C_6$)alkyl, —$(CH_2)_m$—C(O)—($C_1$-$C_6$)alkyl, —O—$(CH_2)_m$—$NH_2$, —O—$(CH_2)_m$—NH—($C_1$-$C_6$)alkyl, —O—$(CH_2)_m$—N—di-(($C_1$-$C_6$)alkyl) and —($C_0$-$C_{12}$)alkyl-$(X^1)_n$;

$X^1$ for each occurrence is independently selected from the group consisting of hydrogen, Cl, F, Br, I, $NO_2$, OH, —$CF_3$, —$OCF_3$, ($C_1$-$C_{12}$)alkyl, ($C_1$-$C_{12}$)alkoxy, —S—($C_1$-$C_6$)alkyl, —$(CH_2)_m$-amino, —$(CH_2)_m$—NH—($C_1$-$C_6$)alkyl, —$(CH_2)_m$—N—di-(($C_1$-$C_6$)alkyl), —$(CH_2)_m$-phenyl and —$(CH_2)_m$—NH—($C_3$-$C_6$)cycloalkyl;

m for each occurrence is independently 0 or an integer from 1 to 6; and n for each occurrence is independently an integer from 1 to 5.

A preferred group of compounds of the compounds of formula (II) are those having the formula (IIa)

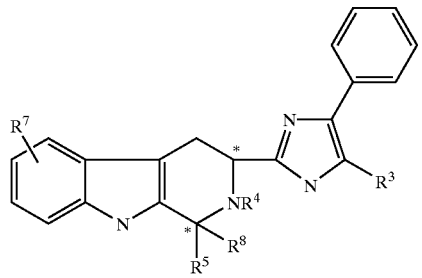

(IIa)

wherein $R^3$ is H or methyl;

$R^4$ is H or methyl;

$R^5$ is H, methyl, ethyl, butyl, pentyl or hexyl;

$R^8$ is ethyl, butyl, pentyl, hexyl, or cyclohexyl;

or $R^5$ and $R^8$ are taken together with the carbon to which they are attached to form spirocyclohexyl, spirocycloheptyl, spiroadamantyl,

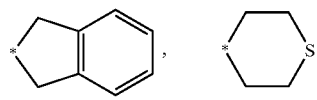

or

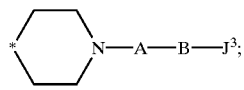

where A is a bond or —C(O)O—; B is a bond, —$(CH_2)$— or —$(CH_2)_2$—;

$J^3$ is H, or phenyl; and $R^7$ is H, Me, F, Cl, OH, —O-methyl or —O—$CH_2$-phenyl.

A more preferred group of compounds of the formula (IIa) are those compounds wherein:

$R^3$, $R^4$ and $R^7$ are each hydrogen, $R^5$ and $R^8$ are together

and the imidazolyl is in the R-configuration;

$R^3$, $R^4$ and $R^7$ are each hydrogen, $R^5$ and $R^8$ are together

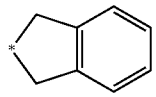

and the imidazolyl is in the R-configuration;

$R^3$, $R^4$ and $R^7$ are each hydrogen, $R^5$ and $R^8$ are together

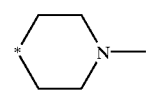

and the imidazolyl is in the R-configuration;

$R^3$, $R^4$ and $R^7$ are each hydrogen, $R^5$ and $R^8$ are together

and the imidazolyl is in the R-configuration, or its hydrochloride salt;

$R^3$ is methyl, $R^4$ and $R^7$ are each hydrogen, $R^5$ and $R^8$ are each n-butyl and the imidazolyl is in the R-configuration;

$R^3$, $R^4$ and $R^7$ are each hydrogen, $R^5$ and $R^8$ are together

and the imidazolyl is in the R-configuration, or its hydrochloride salt;

$R^3$ and $R^4$ are each hydrogen, $R^7$ is 6-O—$CH_2$-phenyl, $R^5$ and $R^8$ are each n-butyl and the imidazolyl is a racemic mixture of the S- and R-configurations;

$R^3$, $R^4$ and $R^7$ are each hydrogen, $R^5$ and $R^8$ are together

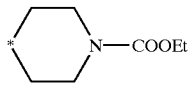

and the imidazolyl is in the R-configuration, or its hydrochloride salt;

$R^3$, $R^4$ and $R^7$ are each hydrogen, $R^5$ and $R^8$ are together

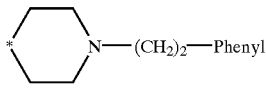

and the imidazolyl is in the R-configuration;

$R^3$ and $R^7$ are each hydrogen, $R^4$ is methyl, $R^5$ and $R^8$ are each n-butyl and the imidazolyl is in the R-configuration;

$R^3$, $R^4$ and are each hydrogen, $R^7$ is 7-fluoro, $R^5$ and $R^8$ are each n-pentyl and the imidazolyl is the racemic mixture of the S- and R-configurations;

$R^3$, $R^4$ and $R^7$ are each hydrogen, $R^5$ and $R^8$ are each n-hexyl and the imidazolyl is in the R-configuration:

$R^3$, $R^4$ and $R^7$ are each hydrogen, $R^5$ is hydrogen and $R^8$ is hexyl in the S-configuration and the imidazolyl is in the R-configuration, or its fumarate salt;

$R^3$, $R^4$ and $R^7$ are each hydrogen, $R^5$ and $R^8$ are each n-butyl and the imidazolyl is in the R-configuration, or its fumarate salt;

$R^3$, $R^4$ and $R^7$ are each hydrogen, $R^5$ and $R^8$ are together

and the imidazolyl is in the R-configuration;

$R^3$, $R^4$ and $R^7$ are each hydrogen, $R^5$ and $R^8$ are each n-butyl and the imidazolyl is in the S-configuration;

$R^3$, $R^4$ and $R^7$ are each hydrogen, $R^5$ and $R^8$ are each ethyl and the imidazolyl is in the R-configuration;

$R^3$, $R^4$ and $R^7$ are each hydrogen, $R^5$ and $R^8$ are each n-pentyl and the imidazolyl is in the R-configuration;

$R^3$, $R^4$ and $R^7$ are each hydrogen, $R^5$ is methyl and $R^8$ is cyclohexyl and the imidazolyl is in the R-configuration;

$R^3$ and $R^4$ are each hydrogen, $R^7$ is 6-methyl $R^5$ and $R^8$ are each n-butyl and the imidazolyl is a racemic mixture of the S- and R-configurations;

$R^3$ and $R^4$ are each hydrogen, $R^7$ is 7-fluoro, $R^5$ and $R^8$ are each n-butyl and the imidazolyl is a racemic mixture of the S- and R-configurations;

$R^3$ and $R^4$ are each hydrogen, $R^7$ is 6-methoxy, $R^5$ and $R^8$ are each n-butyl and the imidazolyl is a racemic mixture of the S- and R-configurations;

$R^3$ and $R^4$ are each hydrogen, $R^7$ is 6-hydroxy, $R^5$ and $R^8$ are each n-butyl and the imidazolyl is a racemic mixture of the S- and R-configurations;

$R^3$ and $R^4$ are each hydrogen, $R^7$ is 6-fluoro, $R^5$ and $R^8$ are each n-butyl and the imidazolyl is a racemic mixture of the S- and R-configurations, or its hydrochloride salt;

$R^3$ and $R^4$ are each hydrogen, $R^7$ is 8-methyl, $R^5$ and $R^8$ are each n-butyl and the imidazolyl is a racemic mixture of the S- and R-configurations;

$R^3$ and $R^4$ are each hydrogen, $R^7$ is 6-methyl, $R^5$ and $R^8$ are each n-pentyl and the imidazolyl is a racemic mixture of the S- and R-configurations; or $R^3$ and $R^4$ are each hydrogen, $R^7$ is 6-chloro, $R^5$ and $R^8$ are each n-butyl and the imidazolyl is a racemic mixture of the S- and R-configurations.

An even more preferred group of compounds of the formula (IIa) are those compounds selected from the group consisting of $R^3$, $R^4$ and $R^7$ are each hydrogen, $R^5$ is hydrogen and $R^8$ is hexyl in the S-configuration and the imidazolyl is in the R-configuration, or its fumarate salt;

$R^3$, $R^4$ and $R^7$ are each hydrogen, $R^5$ and $R^8$ are each n-butyl and the imidazolyl is in the R-configuration, or its fumarate salt;

$R^3$, $R^4$ and $R^7$ are each hydrogen, $R^5$ and $R^8$ are together

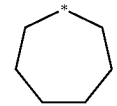

and the imidazolyl is in the R-configuration;

$R^3$, $R^4$ and $R^7$ are each hydrogen, $R^5$ and $R^8$ are each n-butyl and the imidazolyl is in the S-configuration;

$R^3$, $R^4$ and $R^7$ are each hydrogen, $R^5$ and $R^8$ are each ethyl and the imidazolyl is in the R-configuration;

$R^3$, $R^4$ and $R^7$ are each hydrogen, $R^5$ and $R^8$ are each n-pentyl and the imidazolyl is in the R-configuration;

$R^3$, $R^4$ and $R^7$ are each hydrogen, $R^5$ is methyl and $R^8$ is cyclohexyl and the imidazolyl is in the R-configuration;

$R^3$ and $R^4$ are each hydrogen, $R^7$ is 6-methyl $R^5$ and $R^8$ are each n-butyl and the imidazolyl is a racemic mixture of the S- and R-configurations;

$R^3$ and $R^4$ are each hydrogen, $R^7$ is 7-fluoro, $R^5$ and $R^8$ are each n-butyl and the imidazolyl is a racemic mixture of the S- and R-configurations;

$R^3$ and $R^4$ are each hydrogen, $R^7$ is 6-methoxy, $R^5$ and $R^8$ are each n-butyl and the imidazolyl is a racemic mixture of the S- and R-configurations;

$R^3$ and $R^4$ are each hydrogen, $R^7$ is 6-hydroxy, $R^5$ and $R^8$ are each n-butyl and the imidazolyl is a racemic mixture of the S- and R-configurations;

$R^3$ and $R^4$ are each hydrogen, $R^7$ is 6-fluoro, $R^5$ and $R^8$ are each n-butyl and the imidazolyl is a racemic mixture of the S- and R-configurations, or its hydrochloride salt;

$R^3$ and $R^4$ are each hydrogen, $R^7$ is 8-methyl, $R^5$ and $R^8$ are each n-butyl and the imidazolyl is a racemic mixture of the S- and R-configurations;

$R^3$ and $R^4$ are each hydrogen, $R^7$ is 6-methyl, $R^5$ and $R^8$ are each n-pentyl and the imidazolyl is a racemic mixture of the S- and R-configurations; and $R^3$ and $R^4$ are each hydrogen, $R^7$ is 6-chloro, $R^5$ and $R^8$ are each n-butyl and the imidazolyl is a racemic mixture of the S- and R-configurations.

In another aspect, this invention is directed to a pharmaceutical composition comprising one or more of a compound of formula (I) or formula (II) or a pharmaceutically acceptable salt thereof, as defined hereinabove, and a pharmaceutically acceptable carrier.

In yet another aspect, the present invention is directed to a method of eliciting an agonist effect from one or more of a somatostatin subtype receptor in a subject in need thereof, which comprises administering a compound of formula (I) or (II) or a pharmaceutically acceptable salt thereof, as described hereinabove, to said subject.

In still another aspect, the present invention is directed to a method of eliciting an antagonist effect from one or more of a somatostatin subtype receptor in a subject in need thereof, which comprises administering a compound of formula (I) or (II) or a pharmaceutically acceptable salt thereof, as described hereinabove, to said subject.

In a further aspect, the present invention is directed to a method of binding one or more somatostatin subtype receptor in a subject in need thereof, which comprises administering a compound of formula (I) or (II) or a pharmaceutically acceptable salt thereof, as described hereinabove, to said subject.

In an even further aspect, this invention is directed to a method of treating acromegaly, restenosis, Crohn's disease, systemic sclerosis, external and internal pancreatic pseudocysts and ascites, VIPoma, nesidoblastosis, hyperinsulinism, gastrinoma, Zollinger-Ellison Syndrome, diarrhea, AIDS related diarrhea, chemotherapy related diarrhea, scleroderma, Irritable Bowel Syndrome, pancreatitis, small bowel obstruction, gastroesophageal reflux, duodenogastric reflux, Cushing's Syndrome, gonadotropinoma, hyperparathyroidism, Graves' Disease, diabetic neuropathy, Paget's disease, polycystic ovary disease, cancer, cancer cachexia, hypotension, postprandial hypotension, panic attacks, GH secreting adenomas and TSH secreting adenomas, in a subject in need thereof, which comprises administering a compound of formula (I) or (II) or a pharmaceutically acceptable salt thereof, as described hereinabove to said subject.

Another aspect of this invention provides a method of treating diabetes mellitus, hyperlipidemia, insulin insensitivity, Syndrome X, angiopathy, proliferative retinopathy, dawn phenomenon and Nephropathy; inhibition of gastric acid secretion and more particularly peptic ulcers, enterocutaneous and pancreaticocutaneous fistula, Dumping syndrome, watery diarrhea syndrome, acute or chronic pancreatitis and gastrointestinal hormone secreting tumors, inhibition of angiogenesis, treatment of inflammatory disorders such as arthritis, chronic allograft rejection, angioplasty, preventing graft vessel and gastrointestinal bleeding in a subject in need thereof, which comprises administering a compound of formula (I) or (II) or a pharmaceutically acceptable salt thereof, as described hereinabove to said subject.

In still another aspect, this invention provides a method of inhibiting the proliferation of helicobacter pylori in a subject in need thereof, which comprises administering a compound of formula (I) or (II) or a pharmaceutically acceptable salt thereof, as described hereinabove, to said subject.

In still another aspect, this invention provides a method of blocking sodium channel in a subject in need thereof, which comprises administering a compound of formula (I) or a pharmaceutically acceptable salt thereof, to said subject.

In still another aspect, this invention provides a method of blocking sodium channel in a subject in need thereof, which comprises administering a compound of formula (II) or a pharmaceutically acceptable salt thereof, to said subject.

In still another aspect, this invention provides a method of alleviating neuropathic pain in a subject in need thereof, which comprises administering a compound of formula (I) or a pharmaceutically acceptable salt thereof, to said subject.

In still another aspect, this invention provides a method of alleviating neuropathic pain in a subject in need thereof, which comprises administering a compound of formula (II) or a pharmaceutically acceptable salt thereof, to said subject.

In still another aspect, this invention provides a pharmaceutical composition for use as a local anesthetic, comprising a compound of formula (I) or a pharmaceutically acceptable salt thereof, and optionally a pharmaceutically acceptable diluent.

In still another aspect, this invention provides a pharmaceutical composition for use as a local anesthetic, comprising a compound of formula (II) or a pharmaceutically acceptable salt thereof, and optionally a pharmaceutically acceptable diluent.

In still another aspect, this invention provides a method of treating any pathology, disorder or clinical condition involving glutamate release in their etiology in a subject in need thereof, comprising administering a compound of formula (I) or a pharmaceutically acceptable salt thereof, to said subject. A preferred method of the immediately foregoing method is wherein the pathology, disorder or clinical condition is selected from the group consisting of psychiatric disorders, hormonal conditions, metabolic inducted brain damage, sulphite oxidase deficiency, hepatic encephalopathy associated with liver failure, emesis, spasticity, epilepsy, tinnitus, pain and drug abuse and withdrawal.

In still another aspect, this invention provides a method of treating any pathology, disorder or clinical condition involving glutamate release in their etiology in a subject in need thereof, comprising administering a compound of formula (II) or a pharmaceutically acceptable salt thereof, to said subject. A preferred method of the immediately foregoing method is wherein the pathology, disorder or clinical condition is selected from the group consisting of psychiatric disorders, hormonal conditions, metabolic inducted brain damage, sulphite oxidase deficiency, hepatic encephalopathy associated with liver failure, emesis, spasticity, epilepsy, tinnitus, pain and drug abuse and withdrawal.

In still another aspect, this invention provides a method of treating any pathology involving neuronal damage in a subject in need thereof, comprising administering a compound of formula (I) or a pharmaceutically acceptable salt thereof, to said subject. A preferred method of the immediately foregoing method is wherein the pathology is selected from the group consisting of Alzheimer's disease, Huntington's disease, Parkinson's diseases, virus (including HIV)-induced neurodegeneration, amyotrophic lateral sclerosis (ALS), supra-nuclear palsy, olivoponto-cerebellar atrophy (OPCA), and the actions of environmental, exogenous neurotoxins.

In still another aspect, this invention provides a method of treating any pathology involving neuronal damage in a subject in need thereof, comprising administering a compound of formula (II) or a pharmaceutically acceptable salt thereof, to said subject. A preferred method of the immediately foregoing method is wherein the pathology is selected from the group consisting of Alzheimer's disease, Huntington's disease, Parkinson's diseases, virus (including HIV)-induced neurodegeneration, amyotrophic lateral sclerosis (ALS), supra-nuclear palsy, olivoponto-cerebellar atrophy (OPCA), and the actions of environmental, exogenous neurotoxins.

In still another aspect, this invention provides a method of treating arrhythmia in a subject in need thereof, comprising administering a compound of formula (I) or a pharmaceutically acceptable salt thereof, to said subject.

In still another aspect, this invention provides a method of treating arrhythmia in a subject in need thereof, comprising administering a compound of formula (II) or a pharmaceutically acceptable salt thereof, to said subject.

In still another aspect, this invention provides a method of treating epilepsy in a subject in need thereof, comprising administering a compound according to claim 1 or a pharmaceutically acceptable salt thereof to said subject.

In still another aspect, this invention provides a method of treating epilepsy in a subject in need thereof, comprising administering a compound according to claim 12 or a pharmaceutically acceptable salt thereof, to said subject.

DETAILED DESCRIPTION OF THE INVENTION

One of ordinary skill will recognize that certain substituents listed in this invention may have reduced chemical stability when combined with one another or with heteroatoms in the compounds. Such compounds with reduced chemical stability are not preferred.

In general, the compounds of Formula (I) and (II) can be made by processes which include processes known in the chemical arts for the production of compounds. Certain processes for the manufacture of Formula (I) and (II) compounds are provided as further features of the invention and are illustrated by the following reaction schemes and examples.

All of the references and patents cited throughout this disclosure are incorporated herein by reference.

In the above structural formulae and throughout the instant application, the following terms have the indicated meanings unless expressly stated otherwise:

The alkyl groups are intended to include those alkyl groups of the designated length in either a straight or branched configuration. Exemplary of such alkyl groups are methyl, ethyl, propyl, isopropyl, butyl, sec-butyl, tertiary butyl, pentyl, isopentyl, hexyl, isohexyl and the like.

When the definition $C_0$-alkyl occurs in the definition, it means a single covalent bond.

The alkoxy groups specified above are intended to include those alkoxy groups of the designated length in either a straight or branched configuration. Exemplary of such alkoxy groups are methoxy, ethoxy, propoxy, isopropoxy, butoxy, isobutoxy, tertiary butoxy, pentoxy, isopentoxy, hexoxy, isohexoxy and the like.

The term halogen or halo is intended to include the halogen atoms fluorine, chlorine, bromine and iodine.

The term cycloalkyl is intended to include a mono-cycloalkyl (e.g., cyclopentyl, cyclohexyl, etc.), a bi-cycloalkyl (e.g., bicyclo[2.2.1]hepta-2,5-diene, etc.) or a tri-cycloalkyl group (e.g., adamantyl, etc.) of the indicated carbon number known to those of skill in the art, optionally having double or triple bonds therein.

The term aryl is intended to include aromatic rings known in the art, which can be mono-cyclic, bi-cyclic or tri-cyclic, such as phenyl, naphthyl, indenyl, azulenyl and anthracene.

The term heterocycle includes mono-cyclic, bi-cyclic and tri-cyclic systems having one or more heteroatoms, such as oxygen, nitrogen and/or sulfur. The ring systems may be aromatic, for example pyridine, indole, quinoline, pyrimidine, thiophene (also known as thienyl), furan, benzothiophene, tetrazole, dihydroindole, indazole, N-formylindole, benzimidazole, thiazole, and thiadiazole. The ring systems may be non-aromatic, for example pyrrolidine, piperidine, morpholine and the like.

What is meant by the following description, which appears in the claims:

"$R^9$ and $R^{10}$ are taken together with the nitrogen to which they are attached to form a ring having 5 to 8 members including the nitrogen atom that $R^9$ and $R^{10}$ are attached to, where one of the ring members may optionally be an oxygen atom or $NR^{11}$, where $R^{11}$ is $(C_1-C_6)$alkyl, —C(O)—$(C_1-C_6)$alkyl, —C(O)—$NH_2$, —C(O)—NH—$(C_1-C_6)$alkyl, —C(O)—N$((C_1-C_6)$alkyl$)_2$, —C(S)—$NH_2$, —C(S)—NH—$(C_1-C_6)$alkyl, —C(S)—N$((C_1-C_6)$alkyl$)_2$, or optionally-substituted-phenyl-$(C_0-C_6)$alkyl-"

is that the following types of moities result:

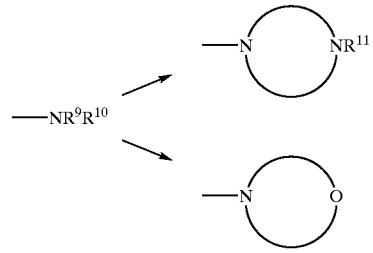

where $R^{11}$ is as defined hereinabove and the arcs represent the carbon members of the ring (however, the symmetry of the arcs is not intended to indicate that they are necessarily of equal number of carbons).

The chemist of ordinary skill will recognize that certain combinations of heteroatom-containing substituents listed in this invention define compounds which will be less stable under physiological conditions. Accordingly, such compounds are less preferred.

When a chemical structure as used herein has an arrow emanating from it, the arrow indicates the point of attachment. For example, the structure

is a pentyl group. When an arrow is drawn through a cyclic moiety, the arrow indicates that the cyclic moiety can be attached at any of the available bonding points, for example

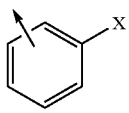

means that the phenyl can be bonded ortho, meta or para to the X group. When an arrow is drawn through a bi-cyclic or a tri-cyclic moiety, the arrow indicates that the bi-cyclic or tri-cyclic ring can be attached at any of the available bonding points in any of the rings, for example

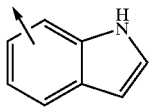

means that the indole is bonded either through the phenyl portion of the ring or the nitrogen containing ring portion.

In the definition for formula (II) when $R^5$ and $R^8$ are taken together with the carbon atom to which they are attached is defined to be, for example

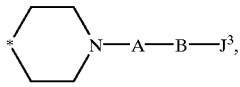

the * in the ring indicates that it is the carbon atom that $R^5$ and $R^8$ are attached to, thus, forming a spiro compound.

Compounds of the present invention having the following core structure are numbered according to the following scheme:

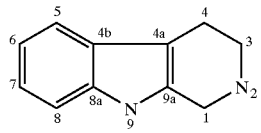

"Treatment" means any treatment of a condition in a mammal, particularly a human, and includes:

(i) preventing the disease from occurring in a subject which may be predisposed to the disease, but has not yet been diagnosed as having it;

(ii) inhibiting the condition, i.e., arresting its development; or (iii) relieving the condition, i.e. relieving the symptom of pain.

The term "subject" means the recipient of a compound of the present invention, preferrably a mammal and most preferrably a human.

"Disease state which is treatable by administration of a sodium channel blocker" is intended to cover all disease states which are generally acknowledged in the art to be usefully treated with sodium channel blockers in general, and those disease states which have been found to be usefully treated by the specific sodium channel blocker of our invention, the compounds of formula (I) or (II). Such disease states include, but are not limited to peripheral neuropathies, such as trigerinal neuralgia, postherapeutic neuralgia, diabetic neuropathy, glossopharymgeal neuralgia, lumbar and cervical radiculopathy, reflex sympathetic dystrophy and causalgia, and neuropathy secondary to metastatic infiltration, adiposis dolorosa, and burn pain; and central pain conditions following stroke, thalmic lesions and multiple sclerosis.

"Therapeutically effective amount" refers to that amount of a compound of formula (I) or (II) or a pharmaceutically acceptable salt thereof which is sufficient to effect treatment, as defined above, when administered to a mammal in need of such treatment. The therapeutically effective amount will vary depending on the subject and disease state being treated, the severity of the affliction and the manner of administration, and may be determined routinely by one of ordinary skill in the art. The term "therapeutically effective amount" is implicitly incorporated in the amount of compound administered in a method of the present invention or when said compound is a component in a pharmaceutical composition of the present invention.

The compounds of the instant invention have at least one asymmetric center as noted by the asterisk in the structural formula (I) and (II), above. Additional asymmetric centers may be present on the molecule depending upon the nature of the various substituents on the molecule. Each such asymmetric center will produce two optical isomers and it is intended that all such optical isomers, as separated, pure or partially purified optical isomers, racemic mixtures or diastereomeric mixtures thereof, be included within the scope of the instant invention.

The instant compounds can be generally isolated in the form of their pharmaceutically acceptable acid addition salts, such as the salts derived from using inorganic and organic acids. Examples of such acids are hydrochloric, nitric, sulfuric, phosphoric, acetic, propionic, maleic, succinic, D-tartaric, L-tartaric, malonic, methane sulfonic and the like. In addition, certain compounds containing an acidic function such as a carboxy can be isolated in the form of their inorganic salt in which the counter-ion can be selected from sodium, potassium, lithium, calcium, magnesium and the like, as well as from organic bases.

The pharmaceutically acceptable salts are formed by taking about 1 equivalent of a compound of formula (I) or (II) and contacting it with about 1 equivalent of the appropriate corresponding acid of the salt which is desired. Work-up and isolation of the resulting salt is well-known to those of ordinary skill in the art.

As is known in the art, agonists and antagonists of somatostatin are useful for treating a variety of medical conditions and diseases, such as inhibition of H. pylori proliferation, acromegaly, restenosis, Crohn's disease, systemic sclerosis, external and internal pancreatic pseudocysts and ascites, VIPoma, nesidoblastosis, hyperinsulinism, gastrinoma, Zollinger-Ellison Syndrome, diarrhea, AIDS related diarrhea, chemotherapy related diarrhea, scleroderma, Irritable Bowel Syndrome, pancreatitis, small bowel obstruction, gastroesophageal reflux, duodenogastric reflux and in treating endocrinological diseases and/or conditions, such as Cushing's Syndrome, gonadotropinoma, hyperparathyroidism, Graves' Disease, diabetic neuropathy, Paget's disease, and polycystic ovary disease; in treating various types of cancer such as thyroid cancer, hepatome, leukemia, meningioma and conditions associated with cancer such as cancer cachexia; in the treatment of such conditions as hypotension such as orthostatic hypotension and postprandial hypotension and panic attacks; GH secreting adenomas (Acromegaly) and TSH secreting adenomas. Activation of type 2 but not type 5 subtype receptor has been associated with treating prolactin secreting adenomas. Other indications associated with activation of the somatostatin subtypes are inhibition of insulin and/or glucagon and more particularly diabetes mellitus, hyperlipidemia, insulin insensitivity, Syndrome X, angiopathy, proliferative retinopathy, dawn phenomenon and Nephropathy; inhibition of gastric acid secretion and more particularly peptic ulcers, enterocutaneous and pancreaticocutaneous fistula, Dumping syndrome, watery diarrhea syndrome, acute or chronic pancreatitis and gastrointestinal hormone secreting tumors; inhibition of angiogenesis, treatment of inflammatory disorders such as arthritis; chronic allograft rejection: angioplasty; preventing graft vessel and gastrointestinal bleeding. Somatostatin agonists can also be used for decreasing body weight in a patient. Accordingly, the compounds of the instant invention are useful for the foregoing methods.

Accordingly, the present invention includes within its scope pharmaceutical compositions comprising, as an active ingredient, at least one of the compounds of Formula (I) or (II) in association with a pharmaceutically acceptable carrier.

The compounds of this invention can be administered by oral, parenteral (e.g., intramuscular, intraperitoneal, intravenous or subcutaneous injection, or implant), nasal, vaginal, rectal, sublingual or topical routes of administration and can be formulated with pharmaceutically acceptable carriers to provide dosage forms appropriate for each route of administration.

Solid dosage forms for oral administration include capsules, tablets, pills, powders and granules. In such solid dosage forms, the active compound is admixed with at least one inert pharmaceutically acceptable carrier such as sucrose, lactose, or starch. Such dosage forms can also comprise, as is normal practice, additional substances other than such inert diluents, e.g., lubricating agents such as magnesium stearate. In the case of capsules, tablets and pills, the dosage forms may also comprise buffering agents. Tablets and pills can additionally be prepared with enteric coatings.

Liquid dosage forms for oral administration include pharmaceutically acceptable emulsions, solutions, suspensions, syrups, the elixirs containing inert diluents commonly used in the art, such as water. Besides such inert diluents, compositions can also include adjuvants, such as wetting agents, emulsifying and suspending agents, and sweetening, flavoring and perfuming agents.

Preparations according to this invention for parenteral administration include sterile aqueous or non-aqueous solutions, suspensions, or emulsions. Examples of non-aqueous solvents or vehicles are propylene glycol, polyethylene glycol, vegetable oils, such as olive oil and corn oil, gelatin, and injectable organic esters such as ethyl oleate. Such dosage forms may also contain adjuvants such as preserving, wetting, emulsifying, and dispersing agents. They may be sterilized by, for example, filtration through a bacteria-retaining filter, by incorporating sterilizing agents into the compositions, by irradiating the compositions, or by heating the compositions. They can also be manufactured in the form of sterile solid compositions which can be dissolved in sterile water, or some other sterile injectable medium immediately before use.

Compositions for rectal or vaginal administration are preferably suppositories which may contain, in addition to the active substance, excipients such as coca butter or a suppository wax.

Compositions for nasal or sublingual administration are also prepared with standard excipients well known in the art.

Further, a compound of this invention of formula (I) or (II) can be administered in a sustained release composition such as those described in the following patents. U.S. Pat. No. 5,672,659 teaches sustained release compositions comprising a bioactive agent and a polyester. U.S. Pat. No. 5,595,760 teaches sustained release compositions comprising a bioactive agent in a gelable form. U.S. application Ser. No. 08/929,363 filed Sep. 9, 1997, teaches polymeric sustained release compositions comprising a bioactive agent and chitosan. U.S. application Ser. No. 08/740,778 filed Nov. 1, 1996, teaches sustained release compositions comprising a bioactive agent and cyclodextrin. U.S. application Ser. No. 09/015,394 filed Jan. 29, 1998, teaches absorbable sustained release compositions of a bioactive agent. The teachings of the foregoing patents and applications are incorporated herein by reference.

In general, an effective dosage of a compound of the present invention of the formula (I) or (II) in the compositions of this invention may be varied; however, it is necessary that the amount of the active ingredient be such that a suitable dosage form is obtained. The selected dosage depends upon the desired therapeutic effect, on the route of administration, and on the duration of the treatment, all of which are within the realm of knowledge of one of ordinary skill in the art. Generally, dosage levels of between 0.0001 to 100 mg/kg of body weight daily are administered to humans and other animals, e.g., mammals.

A preferred dosage range is 0.01 to 10.0 mg/kg of body weight daily, which can be administered as a single dose or divided into multiple doses.

Compounds of the instant invention can be and were assessed for its ability to bind to a somatostatin subtype receptor according to the following assays. Human somatostatin subtype receptor binding studies:

The affinity of a compound for human somatostatin subtype receptors 1 to 5 ($sst_1$, $sst_2$, $sst_3$, $sst_4$ and $sst_5$, respectively) is determined by measuring the inhibition of $[^{125}I$-$Tyr^{11}]$SRIF-14 binding to CHO-K1 transfected cells.

The human $sst_1$ receptor gene was cloned as a genomic fragment. A 1.5 Kb PstI-XmnI segment containg 100 bp of the 5'-untranslated region, 1.17 Kb of the entire coding region, and 230 bp of the 3'-untranslated region was modified by the BglII linker addition. The resulting DNA fragment was subcloned into the BamHI site of a pCMV-81 to produce the mammalian expression plasmid (provided by Dr. Graeme Bell, Univ. Chicago). A clonal cell line stably expressing the $sst_1$ receptor was obtained by transfection into CHO-K1 cells (ATCC) using the calcium phosphate co-precipitation method (1). The plasmid pRSV-neo (ATCC) was included as a selectable marker. Clonal cell lines were selected in RPMI 1640 media containing 0.5 mg/ml of G418 (Gibco), ring cloned, and expanded into culture.

The human $sst_2$ somatostatin receptor gene, isolated as a 1.7 Kb BamHI-HindIII genomic DNA fragment and subcloned into the plasmid vector pGEM3Z (Promega), was kindly provided by Dr. G. Bell (Univ. of Chicago). The mammalian cell expression vector is constructed by inserting the 1.7 Kb BamH1-HindII fragment into compatible restriction endonuclease sites in the plasmid pCMV5. A clonal cell line is obtained by transfection into CHO-K1 cells using the calcium phosphate co-precipitation method. The plasmid pRSV-neo is included as a selectable marker.

The human $sst_3$ was isolated at genomic fragment, and the complete coding sequence was contained within a 2.4 Kb BamHI/HindIII fragment. The mammalian expression plasmid, pCMV-h3 was constructed by inserting the a 2.0 Kb NcoI-HindIII fragment into the EcoR1 site of the pCMV vector after modification of the ends and addition of EcoR1 linkers. A clonal cell line stably expressing the $sst_3$ receptor was obtained by transfection into CHO-K1 cells (ATCC)

using the calcium phosphate co-precipitation method. The plasmid pRSV-neo (ATCC) was included as a selectable marker. Clonal cell lines were selected in RPMI 1640 media containing 0.5 mg/ml of G418 (Gibco), ring cloned, and expanded into culture.

The human $sst_4$ receptor expression plasmid, pCMV-HX was provided by Dr. Graeme Bell (Univ. Chicago). The vector contains the 1.4 Kb NheI—NheI genomic fragment encoding the human $sst_4$, 456 bp of the 5'-untranslated region and 200 bp of the 3'-untranslated region, clone into the XbaI/EcoR1 sites of PCMV-HX. A clonal cell line stably expressing the $sst_4$ receptor was obtained by transfection into CHO-K1 cells (ATCC) using the calcium phosphate co-precipitation method. The plasmid pRSV-neo (ATCC) was included as a selectable marker. Clonal cell lines were selected in RPMI 1640 media containing 0.5 mg/ml of G418 (Gibco), ring cloned, and expanded into culture.

The human $sst_5$ gene was obtained by PCR using a λ genomic clone as a template, and kindly provided by Dr. Graeme Bell (Univ. Chicago). The resulting 1.2 Kb PCR fragment contained 21 base pairs of the 5'-untranslated region, the full coding region, and 55 bp of the 3'-untranslated region. The clone was inserted into EcoR1 site of the plasmid pBSSK(+). The insert was recovered as a 1.2 Kb HindIII-XbaI fragment for subcloning into pCVM5 mammalian expression vector. A clonal cell line stably expressing the $SST_5$ receptor was obtained by transfection into CHO-K1 cells (ATCC) using the calcium phosphate co-precipitation method. The plasmid pRSV-neo (ATCC) was included as a selectable marker. Clonal cell lines were selected in RPMI 1640 media containing 0.5 mg/ml of G418 (Gibco), ring cloned, and expanded into culture.

CHO-K1 cells stably expressing one of the human sst receptor are grown in RPMI 1640 containing 10% fetal calf serum and 0.4 mg/ml geneticin. Cells are collected with 0.5 mM EDTA, and centrifuged at 500 g for about 5 min. at about 4° C. The pellet is resuspended in 50 mM Tris, pH 7.4 and centrifuged twice at 500 g for about 5 min. at about 4° C. The cells are lysed by sonication and centrifuged at 39000 g for about 10 min. at about 4° C. The pellet is resuspended in the same buffer and centrifuged at 50000 g for about 10 min. at about 4° C. and membranes in resulting pellet are stored at −80° C.

Competitive inhibition experiments of [$^{125}$I-Tyr$^{11}$]SRIF-14 binding are run in duplicate in polypropylene 96 well plates. Cell membranes (10 μg protein/well) are incubated with [$^{125}$I-Tyr$^{11}$]SRIF-14 (0.05 nM) for about 60 min. at about 37° C. in 50 mM HEPES (pH 7.4), 0.2% BSA, 5 mM $MgCl_2$, 200 KIU/ml Trasylol, 0.02 mg/ml bacitracin and 0.02 mg/ml phenylmethylsulphonylfluoride.

Bound from free [$^{125}$I-Tyr$^{11}$]SRIF-14 is separated by immediate filtration through GF/C glass fiber filter plate (Unifilter, Packard) presoaked with 0.1% polyethylenimine (P.E.I.), using Filtermate 196 (Packard) cell harvester. Filters are washed with 50 mM HEPES at about 0–4° C. for about 4 sec. and assayed for radioactivity using Packard Top Count.

Specific binding is obtained by subtracting nonspecific binding (determined in the presence of 0.1 μM SRIF-14) from total binding. Binding data are analyzed by computer-assisted nonlinear regression analysis (MDL) and inhibition constant (Ki) values are determined.

The determination of whether a compound of the instant invention is an agonist or an antagonist is determined by the following assay.

Functional assay: Inhibition of cAMP intracellular production:

CHO-K1 Cells expressing human somatostatin (SRIF-14) subtype receptors are seeded in 24-well tissue culture multidishes in RPMI 1640 media with 10% FCS and 0.4 mg/ml geneticin. The medium is changed the day before the experiment.

Cells at $10^5$ cells/well are washed 2 times by 0.5 ml and fresh RPMI with 0.2% BSA supplemented with 0.5 mM (1) 3-isobutyl-1-methylxanthine (IBMX) and incubated for about 5 min at about 37° C.

Cyclic AMP production is stimulated by the addition of 1 mM forskolin (FSK) for about 15–30 minutes at about 37° C.

The agonist effect of a compound is measured by the simultaneous addition of FSK (1 μM), SRIF-14 ($10^{-12}$ M to $10^{-6}$ M) and a test compound ($10^{-10}$ M to $10^{-5}$ M).

The antagonist effect of a compound is measured by the simultaneous addition of FSK (1 μM), SRIF-14 (1 to 10 nM) and a test compound ($10^{-10}$ M to $10^{-5}$ M).

The reaction medium is removed and 200 ml 0.1 N HCl is added. cAMP is measured using radioimmunoassay method (Kit FlashPlate SMP001A, New England Nuclear).

The compounds of the present invention can be tested for activity in blocking Na channels. The compounds of the invention display binding to the veratridine-sensitive sodium channel. For the binding procedure see for example J. B. Brown, Journal of Neuroscience 6, 2064–2070 (1986), the contents of which are incorporated herein by reference. They block veratridine-induced glutamate release in rat hippocampal slice preparations. The experiment is performed according to a modification of M. J. Leach et al., in Epilepsia 27, 490–497 (1986) and Stroke 24, 1063–1067 (1993), using exogenous glutamate.

The compounds of the instant invention are synthesized according to the following procedures and examples.

β-CARBOLINES

Tetrahydro-β-carbolines

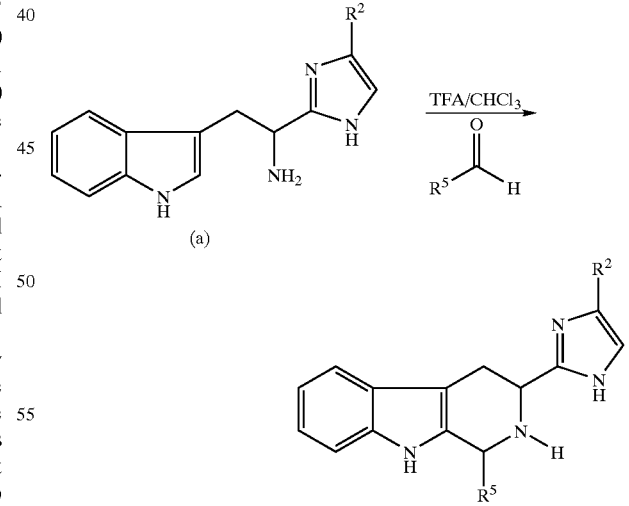

General procedure: An amine of formula (a) is treated with an aldehyde in a protic or aprotic solvent with or without an acid, preferably chloroform with TFA, at about 20–80° C. for about 5–72 hours. The resulting carboline (obtained as a mixture of diastereoisomers) can be isolated either by aqueous work-up followed by flash chromatography on silica gel, or by addition to the reaction mixture of a nucleophile supported on polymer (to trap the excess of

EXAMPLE 1

Diastereomic Mixture at $C_1$ of 1,2,3,4-Tetrahydro-1-(4-methoxyphenyl)-3(S)-(4-phenyl-1H-imidazol-2-yl)-9H-pyrido[3,4-b]indole:

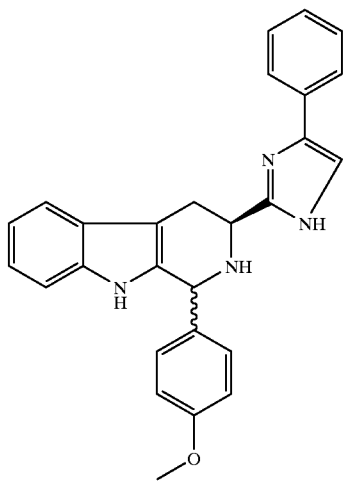

To 2-[1(S)-amino-2-(3-indolyl)ethyl]-)-4-phenyl-1H-imidazole (100 mg, 1 eq) in solution in chloroform (0.8 mL) were successively added p-anisaldehyde (80 mL, 2 eq) and TFA (256 mL, 10 eq). After about 2 days of stirring at about 20° C. the mixture was concentrated under reduced pressure and the residue was dissolved in THF (5 mL). Aminomethylpolystyrene resin (Novabiochem, loading=1.2 mmol/g, 550 mg, 2 eq) was added and the mixture was stirred overnight at about 20° C. and then filtered. The filtrate was then concentrated under reduced pressure and then purified by a rapid filtration on a silica gel pad (Alltech silica cartridges) with ethylacetate as eluent to afford the tetrahydro-β-carboline as a mixture of diastereoisomers (65:35) (yield=78%).

NMR ($^1H$, 400 MHz, $CDCl_3$): 12.2 (m, 1H, NH), 7.77–6.83 (m, 15H, Harom, NH), 5.29, 5.17 (2s, 1H, $H_1$), 4.42 (m, 1H, $H_3$), 3.82, 3.78 (2s, 3H, $OCH_3$), 3.49 (m, 1H, $H_4$), 3.17 (m, 1H, $H_4$), 1.90 (s, 1H, NH). LC/MS: calculated MW=420.51, m/z=421.05 (M+H), m/z=419.07 (M−H).

EXAMPLES 2–1303

The following compounds can be prepared analogously to the procedure described for Example 1 using the appropriate starting materials, which can be obtained from commercial sources or synthesized according to methods known to those skilled in the art or as enabled by the teachings herein. Each combination of $R^2$ and $R^5$, shown below, were or can be synthesized, therefore, the number of Examples are calculated by multiplying ($R^2$(21 substituents))($R^5$(62 substituents))=1302.

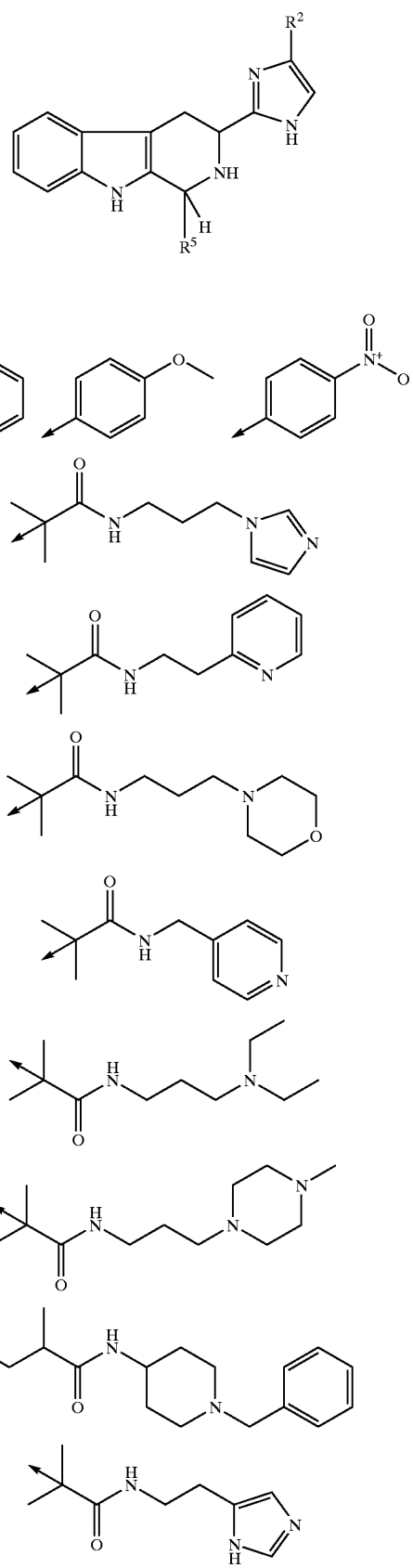

23
-continued
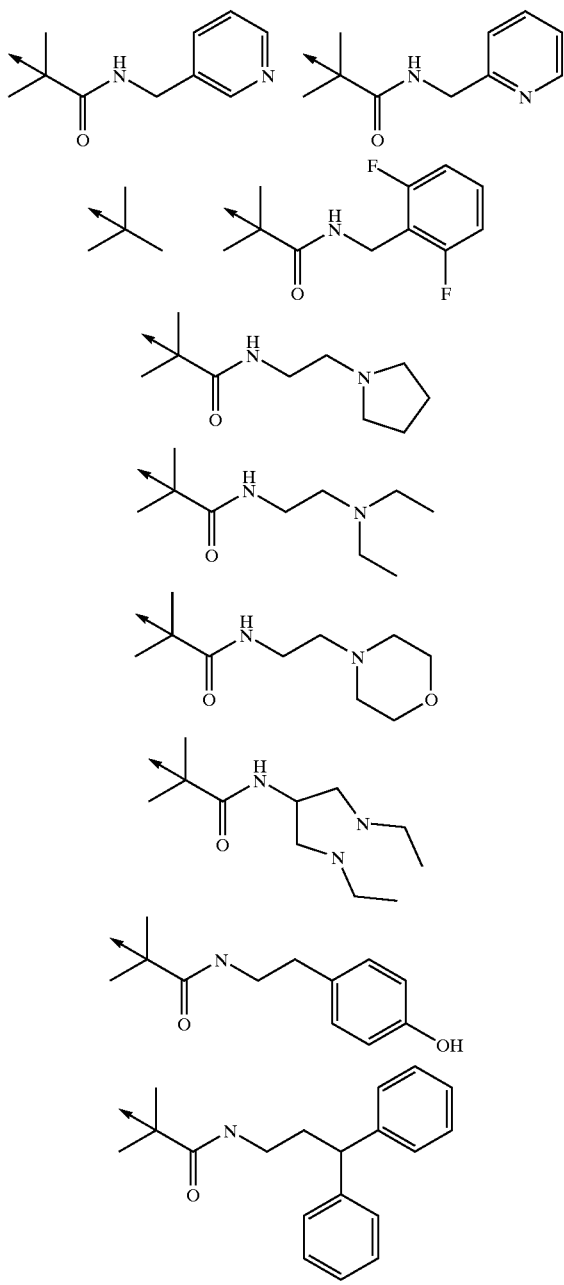
R5:
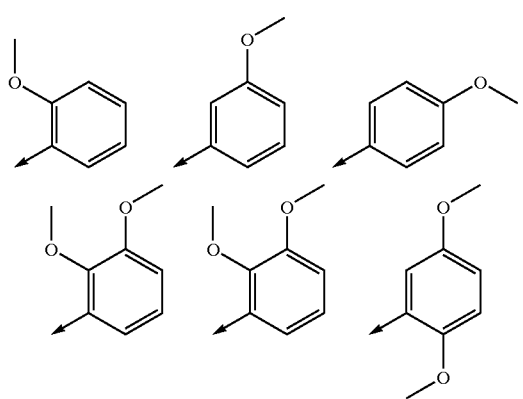
24
-continued
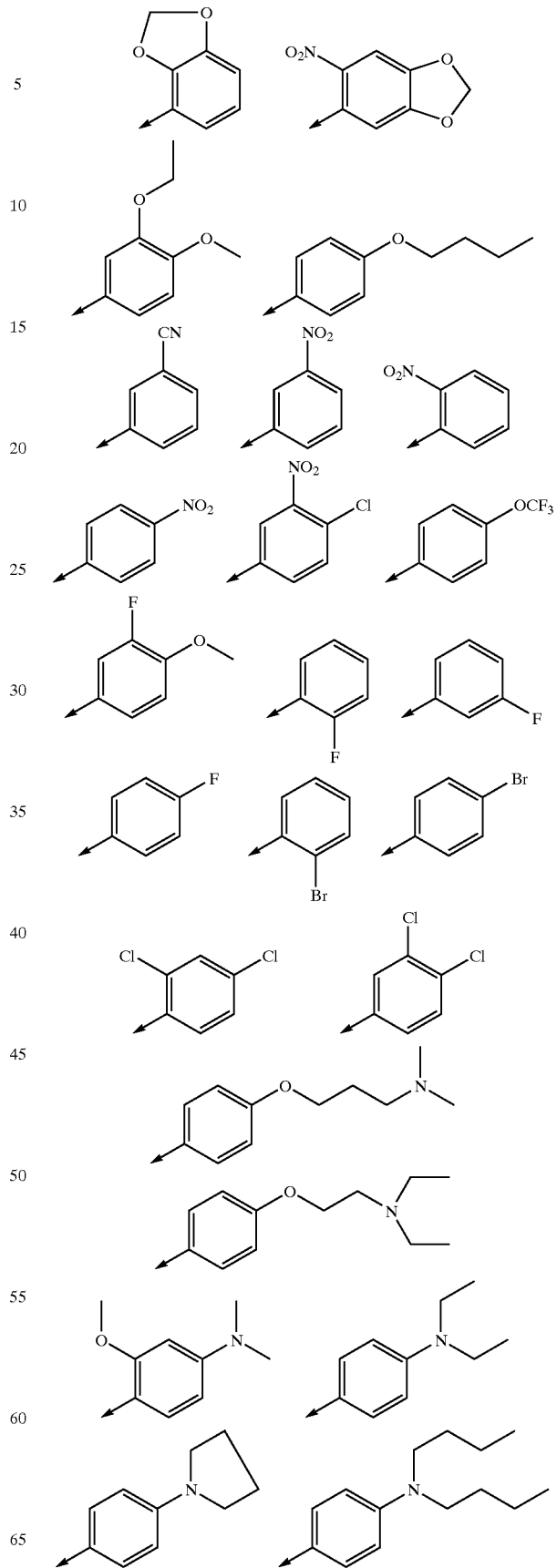

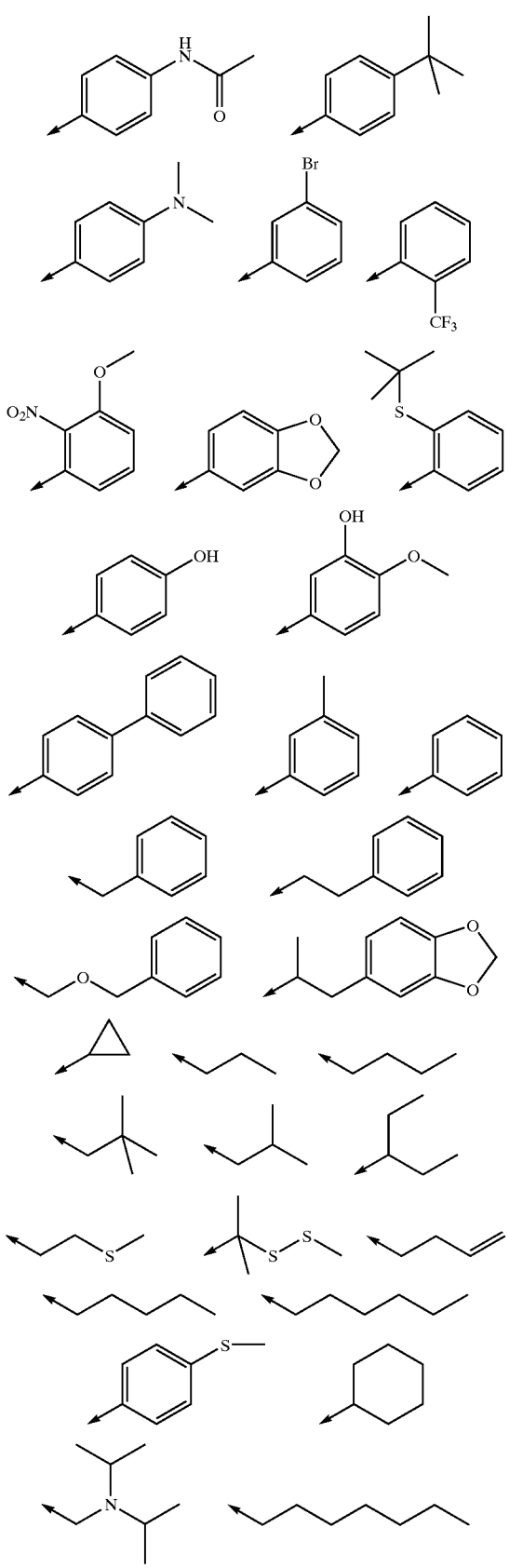

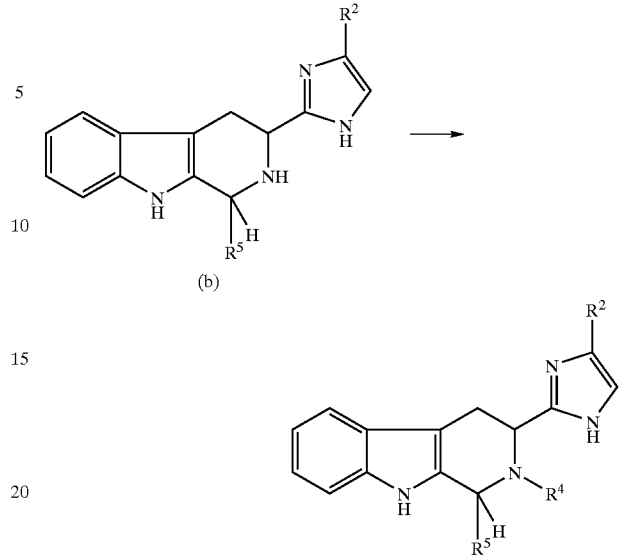

(b)

General procedure: A compound of formula (b) can react with isocyanates, isothiocyanates, N-succinimidyl carbamates, acyl chlorides or activated carboxylic acids in aprotic solvent at 20–70° C. for 2–18 hours. The resulting derivative can be isolated by evaporation of the mixture followed by flash chromatography on silica gel or by addition to the mixture of a nucleophile supported on polymer such as aminomethyl or thiomethyl polystyrene resin followed by filtration.

For protected basic derivatives ($R^4=(CH_2)_n NHBoc$), the corresponding deprotected compounds ($R^4=(CH_2)_n NH_2$) were obtained by treating the N-protected compound under acidic conditions (DCM/TFA 10%).

EXAMPLE 1304

Diastereomic Mixture at $C_1$ of 1,2,3,4-Tetrahydro-1-(4-methoxyphenyl)-2-[(phenylamino)carbonyl]-3(S)-(4-phenyl-1H-imidazol-2-yl)-9H-pyrido[3,4-b]indole:

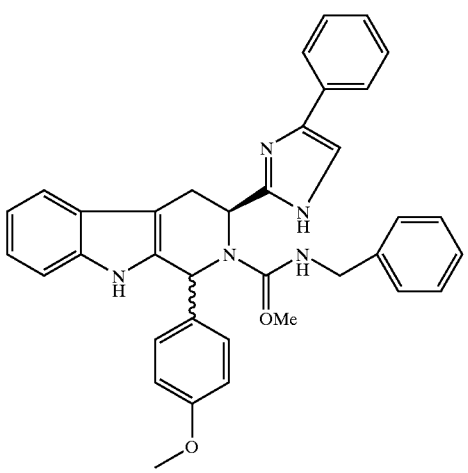

To a solution of a diastereomeric mixture of 1,2,3,4-tetrahydro-1-(4-methoxyphenyl)-3(S)-(4-phenyl-1H- imidazol-2-yl)-9H-pyrido[3,4-b]indole (50 mg) in chloroform (700 mL) was added benzyl isocyanate. The mixture was stirred overnight at about 20° C. and then diluted with chloroform (2 mL). Aminomethylpolystyrene resin (Novabiochem, loading 1.2 mmol/g, 198 mg, 2 eq) was added to the mixture. After about 15 hours of shaking at about 20° C., the mixture was filtered and the filtrate concentrated under reduced pressure to yield the title compound (60 mg, 92% yield).

NMR ($^1$H, 400 MHz, CDCl$_3$) δ: 9.2–6.7 (m, 22H, arom. H, NH), 6.25 (m, 1H, H$_1$), 5.80 (m, 1H, H$_3$), 4.52–4.32 (m, 2H, CH$_2$Ph), 3.81–3.28 (m, 5H, OCH$_3$, H$_4$, H$_4$). LC/MS: calculated MW: 553.66, m/z=554.2 (M+H).

EXAMPLES 1305–1332

The following compounds can be prepared analogously to the procedure described for Example 1304 using the appropriate starting materials, which can be obtained from commercial sources or synthesized according to methods known to those skilled in the art or as enabled by the teachings herein. Each combination of R$^4$ and R$^5$, shown below, were or can be synthesized, therefore, the number of Examples are calculated by multiplying (R$^4$(9 substituents))(R$^5$(3 substituents))=27.

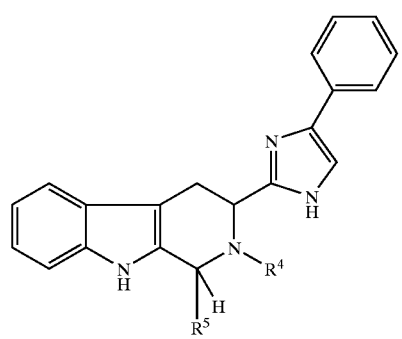

R$^4$ =

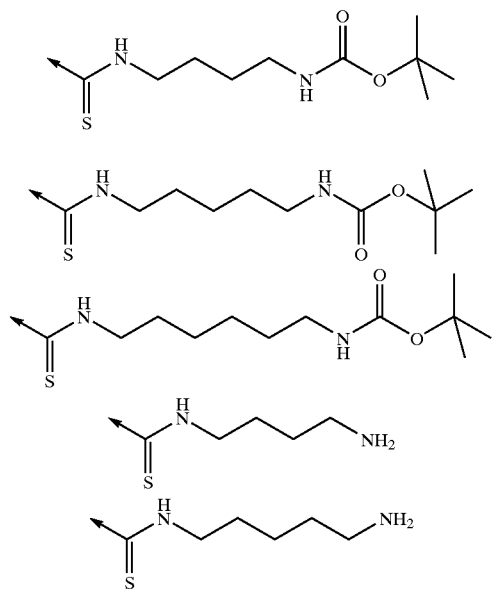

R$^5$ =

β-carbolines

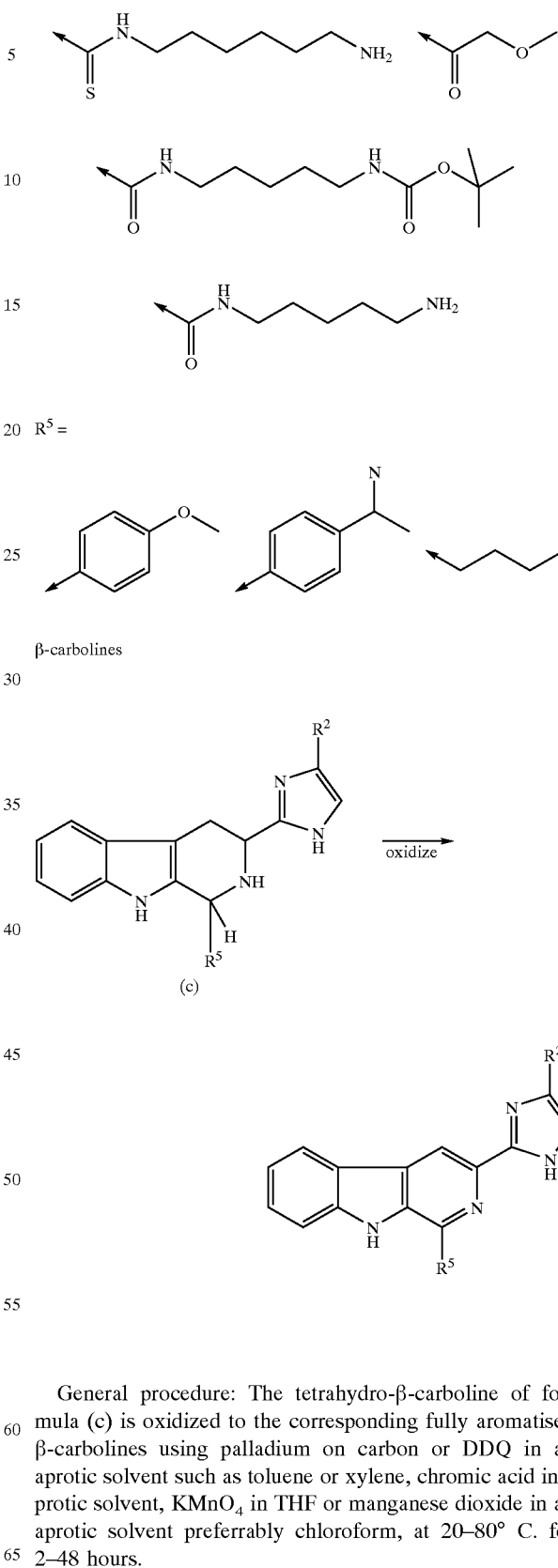

General procedure: The tetrahydro-β-carboline of formula (c) is oxidized to the corresponding fully aromatised β-carbolines using palladium on carbon or DDQ in an aprotic solvent such as toluene or xylene, chromic acid in a protic solvent, KMnO$_4$ in THF or manganese dioxide in an aprotic solvent preferrably chloroform, at 20–80° C. for 2–48 hours.

EXAMPLE 1333

1-Butyl-3-(4-phenyl-1H-imidazol-2-yl)-9H-pyrido[3,4-b]indole:

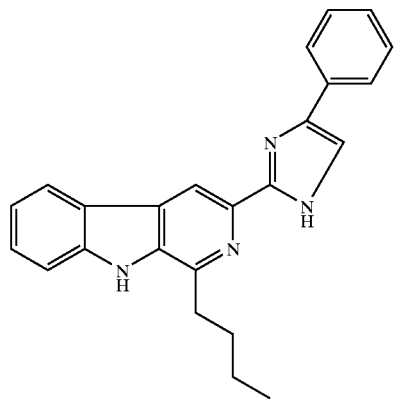

A mixture of 1,2,3,4-tetrahydro-1-butyl-3(R)-(4-phenyl-1H-imidazol-2-yl)-9H-pyrido[3,4-b]indole (100 mg, 1 eq) and manganese dioxide (600 mg) in chloroform (7 mL) was heated at about 40° C. for about 3 hours. The mixture was cooled down to about 20° C. and filtered over a CELITE® pad. The filtrate was concentrated under reduced pressure to yield quantitatively the fully aromatized carboline (97 mg).

NMR ($^1$H, 400 MHz, CDCl$_3$): 10.8 (s, 1H, NH), 8.77–7.25 (m, 11H, arom. H, NH), 3.07 (t, 2H, $^3$J=8 Hz, CH$_2$), 1.85 (m, 2H, CH$_2$), 2.42 (m, 2H, CH$_2$), 0.91 (t, 3H, $^3$J=8 Hz, CH$_3$). LC/MS: calculated MW=366.46, m/z=367.19 (M+H), m/z=479.15 (M+TFA).

EXAMPLE 1334–1336

The following compounds were prepared analogously to the procedure described for Example 1333 using the appropriate starting materials, which can be obtained from commercial sources or synthesized according to methods known to those skilled in the art or as enabled by the teachings herein.

Example 1334

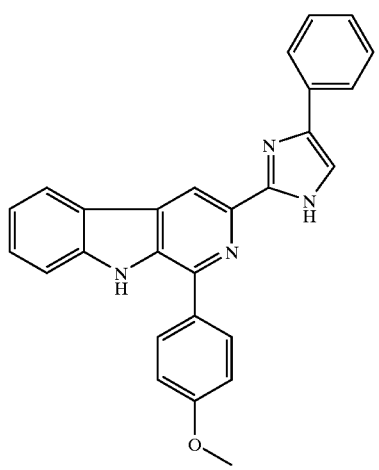

Example 1335

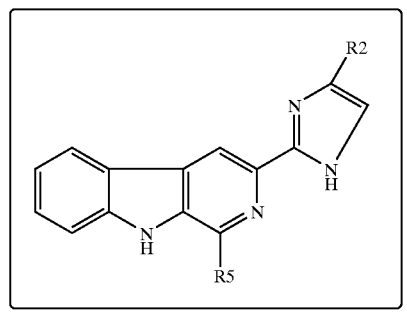

Example 1336

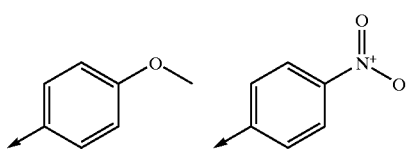

EXAMPLE 1337–1453

The following Examples can be made substantially according to the procedure of Example 1333 using the appropriate starting materials which are commercially available or can synthesized according to literature methods known to those skilled in the art or as enabled by the teachings herein. The number of examples are calculated as follows (R2(4 substituents))(R5(39 substituents))=156.

R5 =

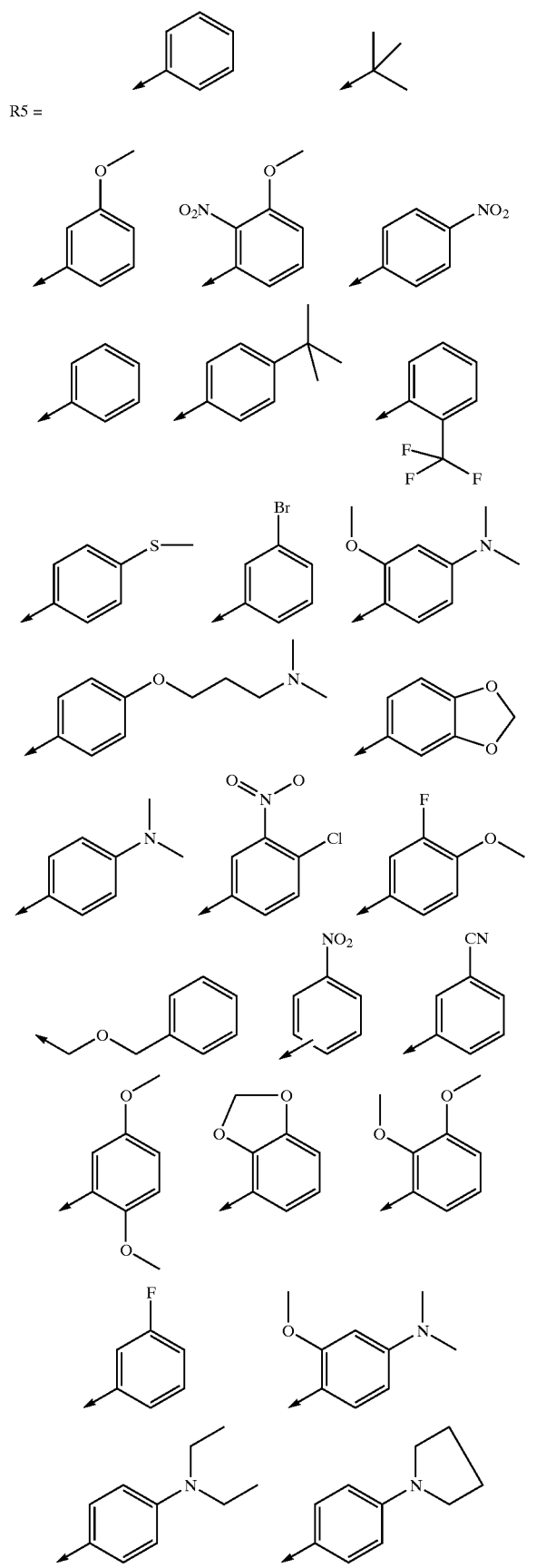

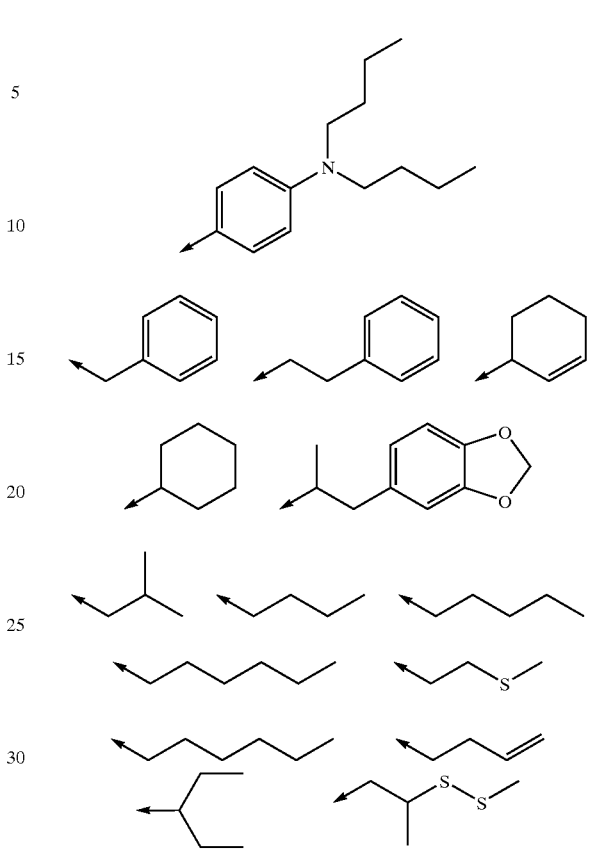

EXAMPLE 1494

(1R)-1-(4,5-Dimethyl-1,3-oxazol-2-yl)-2-(1H-indol-3-yl)-1-ethanamine Hydrochloride

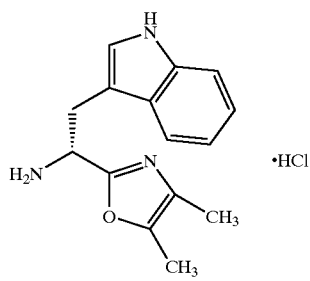

A solution of tert-butyl(1R)-1-(4,5-dimethyl-1,3-oxazol-2-yl)-2-(1H-indol-3-yl)ethylcarbamate (3 g, 8.4 mmol) in HCl/AcOEt 1N (80 ml) was stirred at room temperature for about 2.5 hours. The mixture was concentrated under reduced pressure, diethyl ether (100 ml) added, and the white precipitate collected by filtration, and washed with diethyl ether to afford the hydrochloride salt of the desired product (2.4 g). Melting point: 172–174° C.

(3R)-1,1-Dibutyl-3-(4,5-dimethyl-1,3-oxazol-2-yl)-2,3,4,9-tetrahydro-1H-β-carboline Hydrochloride

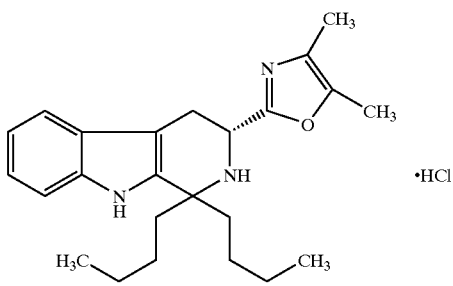

To a solution of (1R)-1-(4,5-dimethyl-1,3-oxazol-2-yl)-2-(1H-indol-3-yl)-1-ethanamine hydrochloride (1.2 g, 3.6 mmol) in isopropanol (20 ml) was added 5-nonanone (3.1 ml, 20 mmol) and the mixture was refluxed for about 24 hours. The solvent was evaporated under reduced pressure. To the residue was added water (20 ml) followed by NaHCO₃ (10%) solution until neutral pH, followed by ethyl acetate (3×15 ml). After decantation and extraction the combined organic extracts were washed with water (20 ml) and dried over MgSO₄. The solvent was evaporated under reduced pressure to afford an oil which was purified by column chromatography on silica gel using ethyl acetate/heptane 7:3 as eluent. The resulting oil was dissolved in ethyl acetate (15 ml) and a solution of HCl in ethyl acetate (1N) was slowly added at about 20° C. to give a precipitate. The suspension was stirred a few minutes and the precipitate collected by filtration, washed with diethyl ether, and dried to afford 0.14 g the desired product as the hydrochloride salt. Melting point: 128–134° C.

EXAMPLE 1495

(3R)-3-(4-Phenyl-1H-imidazol-2-yl)-2,3,4,9-tetrahydro-1'-benzoyl-spiro[1H-β-carboline-1,4'-piperidine]hydrochloride

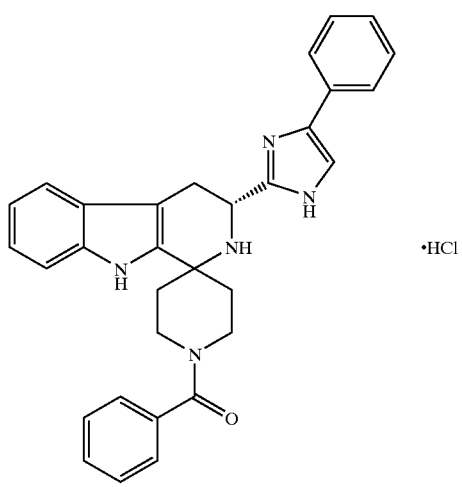

To a solution of (1R)-2-(1H-indol-3-yl)-1-(4-phenyl-1H-imidazol-2-yl)-1-ethanamine hydrochloride (1 g, 2.65 mmol) in isopropanol (15 ml) was added N-benzoyl-4-piperidone (2.64 g, 13 mmol). The solution was refluxed for about one hour and cooled to about 20° C. The solvent was removed under reduced pressure. The residue was treated with dichloromethane (30 ml) and stirred for about 30 min at about 20° C. The resulting precipitate was collected by filtration, washed with dichloromethane and diethyl ether, and dried to afford 1.2 g of the title product as the hydrochloride salt. Melting point: 240–244° C.

EXAMPLE 1496

(3R)-3-(4-Phenyl-1H-imidazol-2-yl)-2,3,4,9-tetrahydro-1'-(tert-butoxycarbonyl)-spiro[1H-β-carboline-1,4'-piperidine]

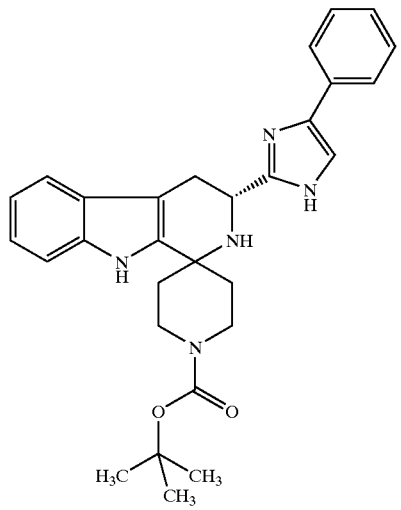

To a solution of (1R)-2-(1H-indol-3-yl)-1-(4-phenyl-1H-imidazol-2-yl)-1-ethanamine hydrochloride (14 g, 35 mmol) in isopropanol (210 ml) was added 1-tert-butoxycarbonyl-4-piperidone (35 g, 170 mmol) and the mixture refluxed for about two hours. The solvent was evaporated under reduced pressure. Water (150 ml) was added to the residue followed by 10% NaHCO₃ solution until neutral pH and extracted by ethyl acetate (4×50 ml). The combined organic extracts were washed with water (2×50 ml) and dried over MgSO₄. The solvent was removed under reduced pressure to afford an oil which solidified on addition of diisopropyl ether (150 ml). The precipitate was collected by filtration, washed with diisopropyl ether and dried to afford 13.5 g of the desired product. Melting point: 118–120° C.

EXAMPLE 1497

(3R)-3-(4-Phenyl-1H-imidazol-2-yl)-2,3,4,9-tetrahydro-spiro[1H-β-carboline-1,4'-piperidine

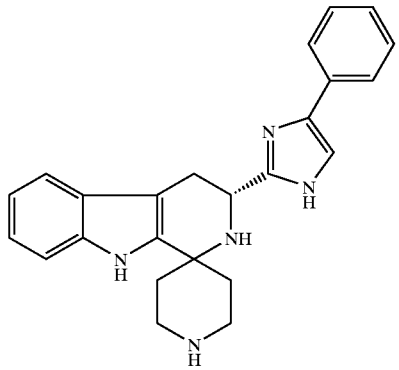

A solution of (3R)-3-(4-phenyl-1H-imidazol-2-yl)-2,3,4,9-tetrahydro-1'-(tert-butoxycarbonyl)-spiro[1H-β-carboline-1,4'-piperidine] (13.5 g, 28 mmol) in ethyl acetate (400 ml) was cooled to about 0° C. with an ice-bath and treated by a stream of anhydrous HCl gas for two hours. The solvent was removed under reduced pressure to afford a semi-solid. Trituration with acetone gave a white solid which was collected by filtration and washed with acetone and diethyl ether. The hydrochloride salt was converted to the free base with NaHCO₃ 10% solution and the aqueous layer was extracted with ethyl acetate (3×50 ml). The combined organic extracts were washed with water (2×50 ml), dried (MgSO₄), filtered and evaporated to afford 10 g of the desired product. Melting point: >250° C.

EXAMPLE 1498

(1R)-2-(1-Benzothiophen-3-yl)-1-(4-phenyl-1H-imidazol-2-yl)-1-ethanamine HCl

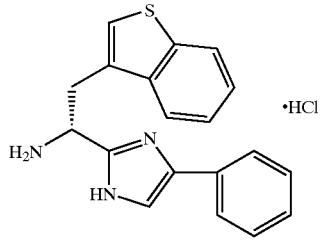

A solution of tert-butyl (1R)-2-(1-benzothiophen-3-yl)-1-(4-phenyl-1H-imidazol-2-yl) ethylcarbamate (4 g, 9.5 mmol) in 70 ml of 1N HCl/AcOEt was warmed up to about 50° C. for one hour. The mixture was concentrated and diethyl ether (50 ml) added. The resulting white precipitate was collected by filtration and washed with diethyl ether to afford the hydrochloride salt of the desired product (3 g). Melting point: 190–192° C.

(3R)-3-(4-Phenyl-1H-imidazol-2-yl)-2,3,4,9-tetrahydro-1'-[N-(3-pyridinyl)carbothio amide]spiro[1H-β-carboline-1,4'-piperidine]

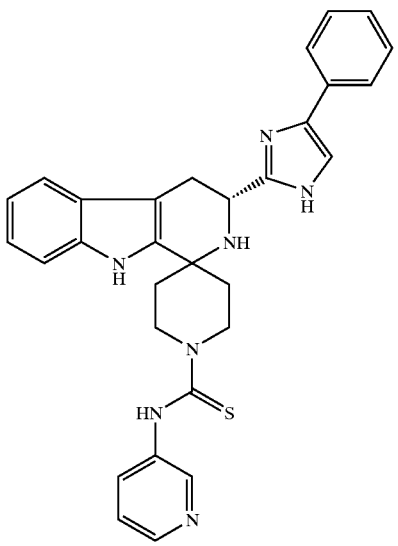

To a solution of (3R)-3-(4-phenyl-1H-imidazol-2-yl)-2,3,4,9-tetrahydro-spiro[1H-β-carboline-1,4'-piperidine] (0.38 g, 10 mmol) in dichloromethane (5 ml) was added 3-pyridyl isothiocyanate (0.136 g, 10 mmol). The mixture was stirred for about 30 min at about 20° C. and the resulting precipitate was collected by filtration and washed with dichloromethane and diethyl ether to afford 0.38 g of the desired product. Melting point: 234–236° C.

EXAMPLE 1499

(3R)-1,1-Dibutyl-3-(4-phenyl-1H-imidazol-2-yl)-1,2,3,4-tetrahydro[1]benzothieno[2,3-c]pyridine

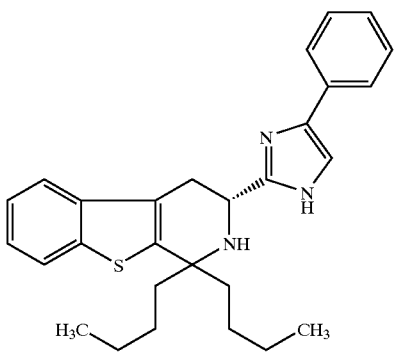

To a solution of (1R)-2-(1-benzothiophen-3-yl)-1-(4-phenyl-1H-imidazol-2-yl)-1-ethanamine (1 g, 2.5 mmol) in n-butanol (20 ml) was added 5-nonanone (2.2 ml, 13 mmol) and the mixture refluxed overnight. The solvent was removed under reduced pressure. To the residue was added water (15 ml) followed by a 10% NaHCO₃ solution until neutral pH and extracted with ethyl acetate (3×20 ml). The combined organic extracts were washed with water (2×10 ml), dried over MgSO₄, filtered. The solvent was evaporated under reduced pressure to afford an oil which was purified by column chromatography on silica gel using ethyl acetate/heptane 1:1 as eluent. After removing the solvent, diisopropyl ether was added to the residue. The resulting white precipitate was filtered off and washed with diisopropyl ether to afford 0.1 g of the title product. Melting point: 198–200° C.

EXAMPLE 1500

(3R)-1,1-Dibutyl-3-(4-phenyl-1H-imidazol-2-yl)-2,3,4,9-tetrahydro-1H-β-carboline Fumarate

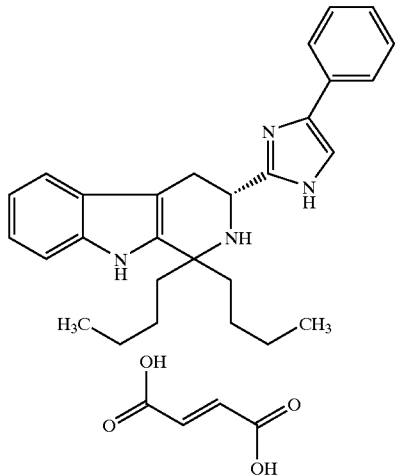

A mixture of (10 g, 33 mmol) of (1R)-2-(1H-indol-3-yl)-1-(4-phenyl-1H-imidazol-2-yl)-1-ethanamine hydrochloride, n-butanol (150 ml) and 5-nonanone (23.44 g, 165 mmol) was refluxed for about 4 hours and then 10 ml of n-butanol were removed using a Dean-Stark apparatus. After refluxing for about a further 2 hours, the mixture was heated at about 100° C. overnight. The solvent was evaporated and the resulting residue partitioned between ethyl acetate (100 ml) and 10% $NaHCO_3$ solution (50 ml). After decantation the organic layer was washed with 10% $NaHCO_3$ solution (50 ml) and water and dried over $MgSO_4$. Evaporation of the solvent afforded a brown residue which was purified by flash chromatography on silica gel (eluent: dichloromethane/ethylacetate 9:1). The pure fractions were collected and concentrated to give, after washing with diisopropyl ether, 3.6 g of the title compound as the free base. Melting point: 160–162° C.

The free base (1.3 g, 3 mmol) was dissolved in acetone (5 ml). Fumaric acid (448 mg, 3 mmol) was added. The mixture was warmed to about 50° C. to obtain a solution. On standing overnight, white crystals appeared. Diethyl ether (20 ml) was added and the dried compound (1.05 g) was collected by filtration. Melting point: 168–170° C.

EXAMPLE 1501

(3R)-3-(4-Phenyl-1H-imidazol-2-yl)-2,3,4,9-tetrahydro-spiro[1H-β-carboline-1,1-cycloheptyl]

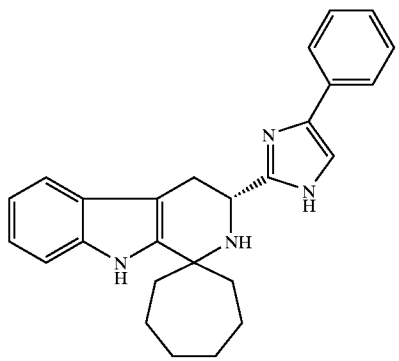

To (0.75 g, 2.5 mmol) of (1R)-2-(1H-indol-3-yl)-1-(4-phenyl-1H-imidazol-2-yl)-1-ethanamine was added 20 ml of 1,2-dichloroethane, trifluoroacetic acid (2 ml, 25 mmol) and cycloheptanone (560 mg, 5 mmol). The mixture was refluxed for about 4 hours. Further trifluoroacetic acid (1 ml) and cycloheptanone (560 mg) were added and reflux was continued for about 4 hours. The solvent was removed under reduced pressure. To the residue was added 20 ml of ethyl acetate and 10% $NaHCO_3$ solution. After decantation the organic layer was washed with water and dried over $MgSO_4$. Evaporation of the solvent afforded a residue which was purified by flash chromatography on silica gel (eluent: heptane/ethyl acetate 3:7). The pure fractions were collected and concentrated to give 80 mg of the title compound. Melting point: 208–210° C.

EXAMPLE 1502

(3R)-3-(4-Phenyl-1H-imidazol-2-yl)-2,3,4,9-tetrahydro-1'-[3-(4methylphenyl)-1-propionyl]spiro[1H-β-carboline-1,4'-piperidine]

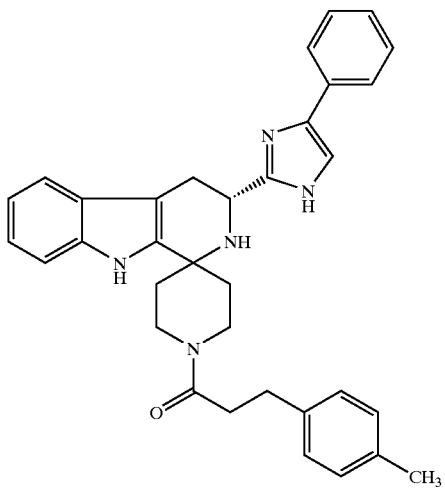

To 20 ml of anhydrous tetrahydrofurane were added (192 mg, 1 mmol) of 1-(3-dimethylaminopropyl)-3-ethylcarbodiimide hydrochloride and (0.14 ml, 1 mmol) of triethylamine. The mixture was stirred for about 15 min then (3R)-3-(4-phenyl-1H-imidazol-2-yl)-2,3,4,9-tetrahydro-spiro[1H-β-carboline-1,4'-piperidine] (383 mg, 1 mmol) and 3-(4-methylphenyl) propionic acid (164 mg, 1 mmol) were added. The reaction mixture was warmed to about 40° C. and stirred overnight at this temperature. The solvent was removed under reduced pressure. The residue was partitioned between ethyl acetate (20 ml) and water (10 ml). After decantation the organic layer was washed with 10% $NaHCO_3$ solution, water and dried over $MgSO_4$. Evaporation of the solvent afforded a residue which was purified by flash chromatography on silica gel (eluent: ethyl acetate/dichloromethane 1:1). The pure fractions were collected and concentrated. The white solid obtained was washed with diethyl ether and collected by filtration to give 100 mg of the title compound. Melting point: 180–182° C.

EXAMPLE 1503
(3R)-3-(4-Phenyl-1H-imidazol-2-yl)-2,3,4,9-tetrahydro-1'-[N-(4-trifluoromethylphenyl)carboxamide]spiro[1H-β-carboline-1,4'-piperidine]

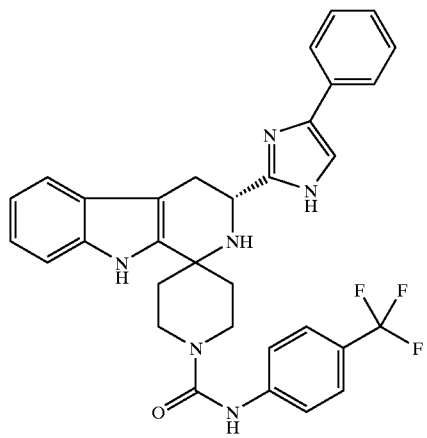

To a solution of (383 mg, 1 mmol) (3R)-3-(4-phenyl-1H-imidazol-2-yl)-2,3,4,9-tetrahydro-spiro[1H-β-carboline-1,4'-piperidine] in dichloromethane was added (187 mg, 1 mmol) of 4-trifluoromethylphenyl isocyanate. The mixture was stirred for about one hour and diluted with 20 ml diethyl ether. The light cream precipitate was collected by filtration, and washed with diethyl ether to give 140 mg of the title product. Melting point: 222–224° C.

EXAMPLE 1504
tert-Butyl (1R)-2-Amino-1-(1H-indol-3-ylmethyl)-2-oxoethylcarbamate

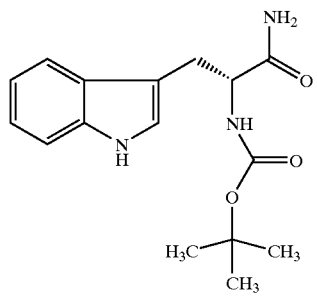

In a reactor under 200 psi of pressure was added (6.2 g, 22 mmol) of methyl (2R)-2-[(tert-butoxycarbonyl)amino]-3-(1H-indol-3-yl)propanoate and 120 ml of methanol saturated with NH$_3$. The solution was stirred at about 85° C. for about 24 hours. After cooling, the solution was evaporated and the residue precipitated by the addition of diisopropyl ether. Filtration gave 5.4 g of the title product as a white powder. Melting point: 142–143° C.

tert-Butyl (1R)-2-Amino-1-(1H-indol-3-ylmethyl)-2-thiooxoethylcarbamate

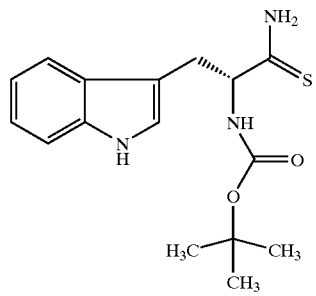

To a solution of (5 g, 160 mmol) of tert-butyl (1R)-2-amino-1-(1H-indol-3-ylmethyl)-2-oxoethylcarbamate in 85 ml of 1,2-dimethoxyethane was added 5.2 g (62 mmol) of NaHCO$_3$ and then (7.3 g, 32 mmol) of P$_2$S$_5$ over a period of about 45 min. The mixture was stirred overnight and the solvent was evaporated. The residue was suspended in ethyl acetate and washed with water, 10% NaHCO$_3$ solution and water. After drying over MgSO$_4$ the organic layer was concentrated and the crude product precipitated by addition of isopentane/diisopropyl ether 1:1. Filtration gave 4.3 g of the title product as a cream powder. MS: 320.2 (MH$^+$) TLC: R$_f$=0.7 (CH$_2$Cl$_2$/MeOH 90:10)

tert-Butyl (1R)-2-(1H-indol-3-yl)-1-(4-phenyl-1,3-thiazol-2-yl)ethylcarbamate

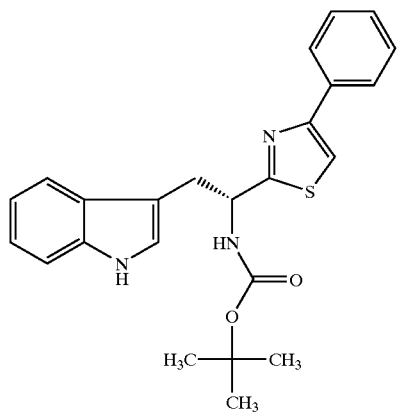

A mixture of (2.24 g, 7 mmol) of tert-butyl (1R)-2-amino-1-(1H-indol-3-ylmethyl)-2-thiooxoethylcarbamate and (1.4 g, 7 mmol) of α-bromoacetophenone was heated until complete melting (90° C.). The temperature was maintained at about 90° C. for about 10 min and after cooling ethyl acetate (50 ml) and water (25 ml) were added. The organic layer was decanted, washed with 10% NaHCO$_3$ solution, water, dried over MgSO$_4$. Evaporation of the solvent afforded a residue which was purified by flash chromatography on silica gel (eluent: dichloromethane/ethyl acetate 95:5). The pure fractions were collected and concentrated to give 1.1 g of the desired product as a cream powder. MS: 420.2 (MH$^+$); TLC: R$_f$=0.7 (SiO$_2$; CH$_2$Cl$_2$/EtOAc 95:5).

(1R)-2-(1H-Indol-3-yl)-1-(4-phenyl-1,3-thiazol-2-yl)-1-ethanamine Hydrochloride

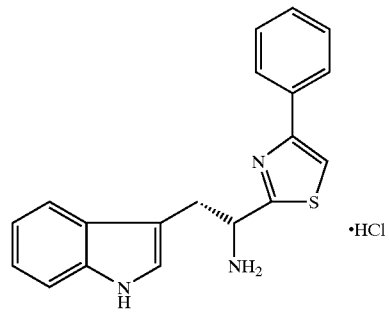

To (1.2 g, 2.85 mmol) of tert-butyl (1R)-2-(1H-indol-3-yl)-1-(4-phenyl-1,3-thiazol-2-yl)ethylcarbamate was added ethyl acetate (10 ml) and 20 ml of a 1N HCl solution in ethyl acetate. The solution was stirred for about 2 hours at about 20° C. followed by about 2 hours at about 50° C. The crystals which formed on cooling were collected by filtration and washed with diethyl ether to give 1 g of the title product as an orange powder. Melting point: 170–172° C.

(3R)-1,1-Dibutyl-3-(4-phenyl-1,3-thiazol-2-yl)-2,3,4,9-tetrahydro-1H-β-carboline

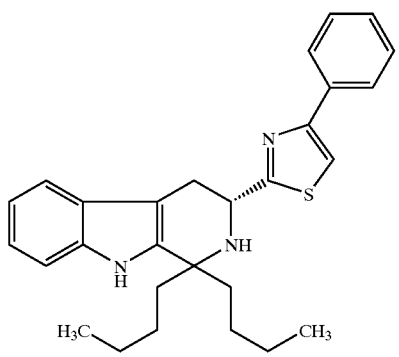

To a solution of (1R)-2-(1H-indol-3-yl)-1-(4-phenyl-1,3-thiazol-2-yl)-1-ethanamine hydrochloride (210 mg, 0.59 mmol) in n-butanol (15 ml) was added 0.45 ml (2.5 mmol) of 5-nonanone. The mixture was heated under reflux for about two hours and then 5 ml of n-butanol was removed by Dean-Stark. Reflux was continued for about 3 hours. The mixture was concentrated under reduced pressure and the residue partitioned between 15 ml ethyl acetate and 15 ml 10% NaHCO$_3$ solution. After decantation the organic layer was washed with water and dried over MgSO$_4$. Evaporation of the solvent afforded a residue which was purified by flash chromatography on silica gel (eluent: dichloromethane/ethyl acetate 97:3). The pure fractions were collected and concentrated. The residue was dissolved in diethyl ether, and 1N HCl in ethyl acetate was added. The hydrochloride was collected by filtration and washed with diethyl ether to give 85 mg of the title product as an orange powder. Melting point: 134–136° C.

Preparation 1

Tert-butyl(1R)-2-(1-benzothiophen-3-yl)-1-(4-phenyl-1H-imidazol-2-yl)ethyl Carbamate

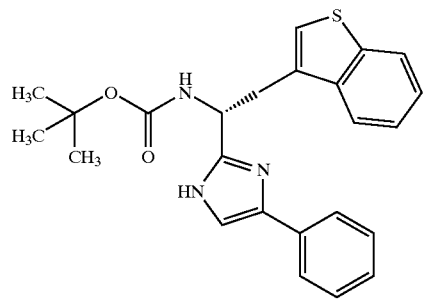

To a solution of Boc-D-3-benzothienylalanine (5 g, 15 mmol) in absolute ethanol (60 ml) and water (20 ml) was added cesium carbonate (2.4 g, 7.5 mmol) and the mixture stirred for about two hours at about 20° C. The solvent was removed under reduced pressure to afford a white powder which was dissolved in dimethylformamide (100 ml) and treated with 2-bromoacetophenone (3 g, 15 mmol). After stirring overnight at about 20° C., the solvent was concentrated under reduced pressure. The residue was treated with ethyl acetate (100 ml) and the precipitate thus obtained (CsBr) was filtered off, washed with ethyl acetate and the filtrate was concentrated under reduced pressure to afford a light brown solid. This solid was dissolved in xylene (100 ml), ammonium acetate (23 g, 300 mmol) was added and the mixture refluxed for about two hours. After cooling to about 20° C., water (50 ml) and ethyl acetate (100 ml) were added. The organic layer was decanted and washed with water (50 ml), 10% NaHCO$_3$ solution (2×50 ml), brine (50 ml) and dried over MgSO$_4$. The solvent was evaporated under reduced pressure. Isopentane (60 ml) was added to the residue which was then filtered to afford 4 g of the title compond as a white powder. Melting point: 116–120° C.

Preparation 2

Tert-butyl (1R)-1-(4,5-Dimethyl-1,3-oxazol-2-yl)-2-(1H-indol-3-yl)ethylcarbamate

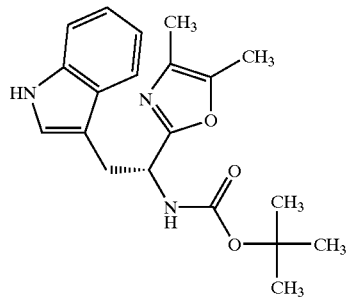

To a solution of Boc-D-TRP-OH (15 g, 34 mmol) in absolute ethanol (80 ml) was added cesium carbonate (5.5 g, 17 mmol). The mixture was stirred for about one hour at about 20° C. and concentrated under reduced pressure to afford a white powder which was dissolved in dimethylformamide (100 ml) and treated with 3-bromo-2-butanone (3.56 ml, 34 mmol). After stirring for about two hours at about 20° C. the solvent was removed under reduced pressure to afford a suspension which was treated with ethyl acetate. The precipitate (CsBr) was filtered off and the filtrate evaporated to afford an oil which was dissolved in xylene (400 ml). Ammonium acetate (52 g, 680 mmol) was added and the mixture was refluxed for about 45 min. After cooling to about 20° C., water (150 ml) and ethyl acetate (100 ml) were added. After decantation the organic layer was washed with water (100 ml), NaHCO$_3$ 10% (2×100 ml) and brine (100 ml), dried over MgSO$_4$ and the solvent evaporated under reduced pressure. The residue was purified by column chromatography on silica gel using ethyl acetate/heptane 1:1 as eluent to afford 3 g of the desired product as a white powder. Melting point: 138–140° C.

The following tables of compounds illustrate some of the compounds of the present invention that were synthesized and provide the HPLC retention time in minutes and mass spectra results of each compound.

Mass spectra were acquired on a single quadrupole electrospray mass spectrometer (Micromass, Platform model), 0.8 Da resolution. A monthly calibration, between 80 and 1000 Da, is performed with sodium and rubidium iodide solution isopropanol/water (1/1 Vol.).

HPLC retention times were acquired on an HPLC system: HP1100 (Hewlett-Packard) equipped with a photodiode array UV detector.

The HPLC conditions are as follows and the conditions used for each of the following tables of compounds are indicated in the column heading.

Condition A:

| Solvent: A: Water + 0.02% Trifluoroacetic acid B: Acetonitrile | | |
|---|---|---|
| T(min) | A % | B % |
| 0 | 100 | 0 |
| 1 | 100 | 0 |
| 8 | 30 | 70 |
| 10 | 30 | 70 |

Flow rate: 1.1 ml/min
Injection volume: 5 μL
Column: Uptisphere ODS 3 μm 33*4.6 mm i.d
Temp.: 40° C.
Wavelength: 220 nm Condition A was employed for the HPLC analysis of the compounds in the Tables of Compounds of Formulas 2, 3 and 4.

Condition B:

| Solvent: A: Water + 0.04% Trifluoroacetic acid B: Acetonitrile | | |
|---|---|---|
| T(min) | A % | B % |
| 0 | 100 | 0 |
| 1 | 100 | 0 |
| 8 | 30 | 70 |
| 10 | 30 | 70 |

Flow rate: 1.1 ml/min
Injection volume: 5 μL
Column: Uptisphere ODS 3 μm 33*4.6 mm i.d
Temp.: 40° C.
Wavelength: 220 nm Condition B was employed for the HPLC analysis of the compounds in the Table of Compounds of Formula 1

Condition C:

| Solvent: A: Water + 0.04% Trifluoroacetic acid B: Acetonitrile | | |
|---|---|---|
| T(min) | A % | B % |
| 0 | 90 | 10 |
| 1 | 90 | 10 |
| 8 | 0 | 100 |
| 10 | 0 | 100 |

Flow rate: 1.1 ml/min
Injection volume: 5 μL
Column: Uptisphere ODS 3 μm 33*4.6 mm i.d
Temp.: 40° C.
Wavelength: 250 nm Condition C was employed for the HPLC analysis of the compounds in the Table of Compounds of Formula 5.

FORMULA 1

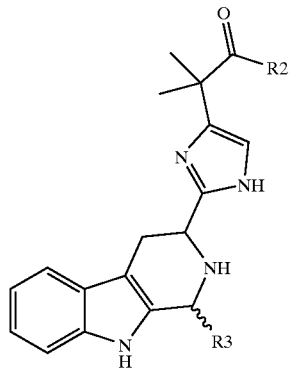

| | R2 | R3 | Analyses Rt (min) | (M + H)+ |
|---|---|---|---|---|
| 1 | *HN-CH2CH2-N(morpholine) | -CH2CH2CH2-* | 4.6 | 493.3 |
| 2 | benzyl-piperidin-4-yl-NH-* | -CH2CH2CH2-* | 5.1 | 553.3 |

| | | | | |
|---|---|---|---|---|
| | | -continued | | |
| 3 | (1,2-diethylpyrazolidin-4-yl)NH- | pentyl | 4.9 | 506.4 |
| 4 | (pyridin-2-ylmethyl)NH- | pentyl | 5.0 | 471.3 |
| 5 | Et$_2$N-CH$_2$CH$_2$CH$_2$- | pentyl | 4.7 | 493.4 |
| 6 | (pyridin-3-ylmethyl)NH- | pentyl | 4.7 | 471.3 |
| 7 | 4-HO-C$_6$H$_4$-CH$_2$CH$_2$-NH- | pentyl | 5.8 | 500.3 |
| 8 | Ph$_2$CH-CH$_2$CH$_2$-NH- | pentyl | 7.2 | 574.3 |
| 9 | pyrrolidin-1-yl-CH$_2$CH$_2$-NH- | pentyl | 4.7 | 477.4 |
| 10 | (4-methylpiperazin-1-yl)-CH$_2$CH$_2$CH$_2$- | pentyl | 4.4 | 520.4 |
| 11 | morpholin-4-yl-CH$_2$CH$_2$-NH- | cyclohexyl | 4.8 | 519.3 |
| 12 | 1-benzylpiperidin-4-yl-NH- | cyclohexyl | 5.3 | 579.4 |
| 13 | (1,2-diethylpyrazolidin-4-yl)NH- | cyclohexyl | 5.1 | 532.4 |

-continued

| # | R1 | R2 | t | MS |
|---|---|---|---|---|
| 14 | *–HN–CH2–(2-pyridyl) | cyclohexyl–* | 5.2 | 497.3 |
| 15 | *–(CH2)3–N(Et)2 | cyclohexyl–* | 4.9 | 519.4 |
| 16 | (3-pyridyl)–CH2–NH–* | cyclohexyl–* | 4.9 | 497.3 |
| 17 | *–HN–CH2CH2–(4-hydroxyphenyl) | cyclohexyl–* | 6.0 | 526.3 |
| 18 | Ph2CH–CH2CH2–NH–* | cyclohexyl–* | 7.4 | 600.4 |
| 19 | *–HN–CH2CH2–(1-pyrrolidinyl) | cyclohexyl–* | 4.9 | 503.4 |
| 20 | *–(CH2)4–(4-methylpiperazin-1-yl) | cyclohexyl–* | 4.6 | 546.4 |
| 21 | *–HN–CH2CH2–(morpholin-4-yl) | 2-NO2-3-OMe-phenyl–* | 5.0; 4.9 | 588.3 |
| 22 | (1-benzylpiperidin-4-yl)–NH–* | 2-NO2-3-OMe-phenyl–* | 5.4; 5.3 | 648.3 |
| 23 | (1,2-diethylpyrazolidin-4-yl)–NH–* | 2-NO2-3-OMe-phenyl–* | 5.2; 5.1 | 601.3 |

-continued
| | | | | |
|---|---|---|---|---|
| 24 | 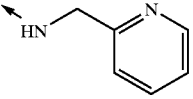 | 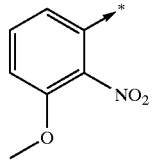 | 5.4; 5.3 | 566.2 |
| 25 | 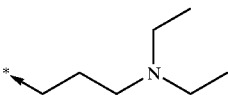 | 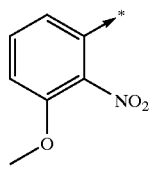 | 5.05; 4.97 | 588.3 |
| 26 | 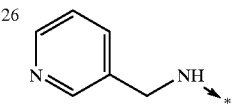 | 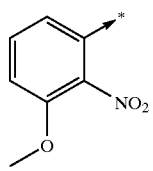 | 5.1; 5.0 | 566.2 |
| 27 | 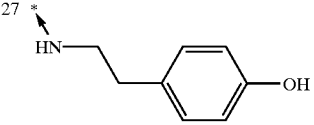 | 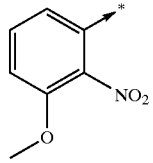 | 6.2; 6.1 | 595.3 |
| 28 | 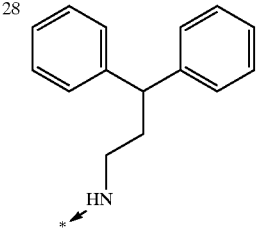 | 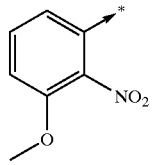 | 7.4 | 669.3 |
| 29 | 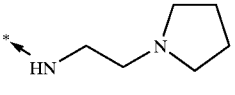 | 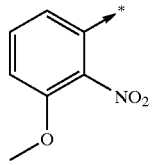 | 5.05; 4.95 | 572.3 |
| 30 | 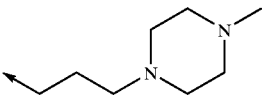 | 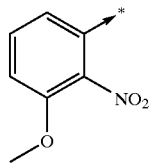 | 4.7 | 615.3 |
| 31 | 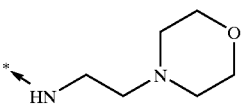 | 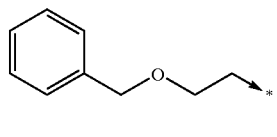 | 5.0 | 557.3 |
| 32 | 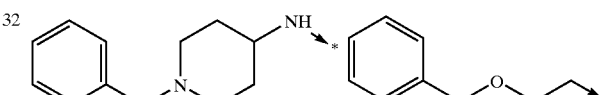 | 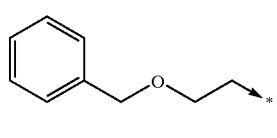 | 5.4 | 617.4 |

| | | | | |
|---|---|---|---|---|
| | | | -continued | |
| 33 | ![structure] 1,2-diethylpyrazolidin-4-ylamine | ![structure] benzyloxyethyl | 5.2 | 570.3 |
| 34 | ![structure] (pyridin-2-yl)methylamine | ![structure] benzyloxyethyl | 5.4 | 535.3 |
| 35 | ![structure] 3-(diethylamino)propyl | ![structure] benzyloxyethyl | 5.1 | 557.4 |
| 36 | ![structure] (pyridin-3-yl)methylamine | ![structure] benzyloxyethyl | 5.1 | 535.3 |
| 37 | ![structure] 2-(4-hydroxyphenyl)ethylamine | ![structure] benzyloxyethyl | 6.2 | 564.3 |
| 38 | ![structure] 3,3-diphenylpropylamine | ![structure] benzyloxyethyl | 7.5 | 638.4 |
| 39 | ![structure] 2-(pyrrolidin-1-yl)ethylamine | ![structure] benzyloxyethyl | 5.1 | 541.3 |
| 40 | ![structure] 4-(4-methylpiperazin-1-yl)butyl | ![structure] benzyloxyethyl | 4.8 | 584.4 |
| 41 | ![structure] 2-(morpholin-4-yl)ethylamine | ![structure] benzo[1,3]dioxol-5-yl | 4.7 | 557.3 |
| 42 | ![structure] 1-benzylpiperidin-4-ylamine | ![structure] benzo[1,3]dioxol-5-yl | 5.1 | 617.3 |
| 43 | ![structure] 1,2-diethylpyrazolidin-4-ylamine | ![structure] benzo[1,3]dioxol-5-yl | 4.9 | 570.3 |

-continued

| # | R group 1 | R group 2 | col1 | col2 |
|---|---|---|---|---|
| 44 | *-NH-CH2-(2-pyridyl) | benzo[1,3]dioxol-5-yl-* | 5.0 | 535.3 |
| 45 | *-CH2CH2CH2-N(Et)2 | benzo[1,3]dioxol-5-yl-* | 4.8 | 557.3 |
| 46 | (3-pyridyl)-CH2-NH-* | benzo[1,3]dioxol-5-yl-* | 4.8 | 535.2 |
| 47 | *-NH-CH2CH2-(4-hydroxyphenyl) | benzo[1,3]dioxol-5-yl-* | 5.8 | 564.3 |
| 48 | Ph2CH-CH2CH2-NH-* | benzo[1,3]dioxol-5-yl-* | 7.2 | 638.3 |
| 49 | *-NH-CH2CH2-(pyrrolidin-1-yl) | benzo[1,3]dioxol-5-yl-* | 4.7 | 541.3 |
| 50 | *-CH2-(2,6-difluorophenyl) | benzo[1,3]dioxol-5-yl-* | 6.3 | 570.2 |
| 51 | *-NH-CH2CH2-(morpholin-4-yl) | 4-(methylthio)phenyl-* | 5.0 | 559.3 |
| 52 | 1-benzylpiperidin-4-yl-NH-* | 4-(methylthio)phenyl-* | 5.4 | 619.3 |
| 53 | 1,2-diethylpyrazolidin-4-yl-NH-* | 4-(methylthio)phenyl-* | 5.2 | 572.3 |

-continued
| | | | | |
|---|---|---|---|---|
| 54 | 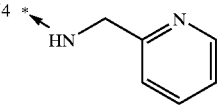 | 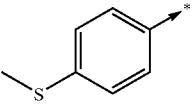 | 5.4 | 537.3 |
| 55 | 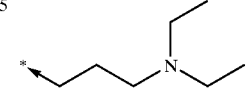 | 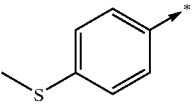 | 5.1 | 559.3 |
| 56 | 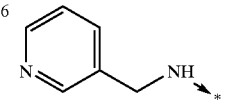 | 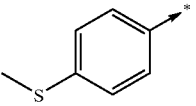 | 5.1 | 537.3 |
| 57 | 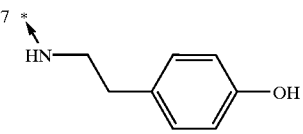 | 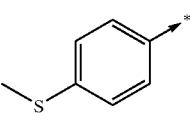 | 6.1 | 566.3 |
| 58 | 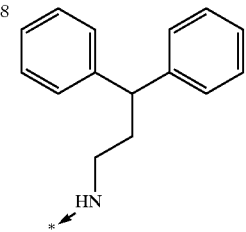 | 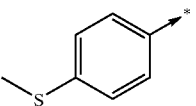 | 7.5 | 640.3 |
| 59 | 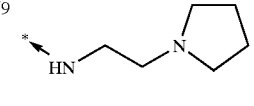 | 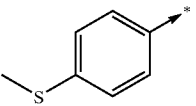 | 5.0 | 543.3 |
| 60 | 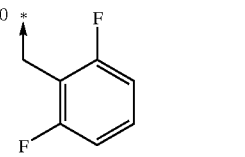 | 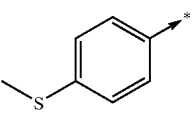 | 6.6 | 572.2 |
| 61 | 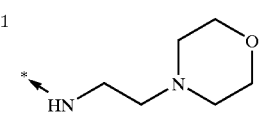 | 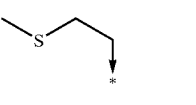 | 4.5 | 511.3 |
| 62 | 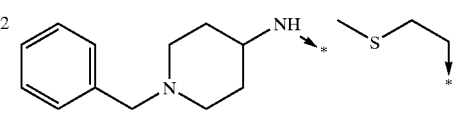 | 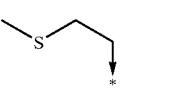 | 5.0 | 571.3 |
| 63 | 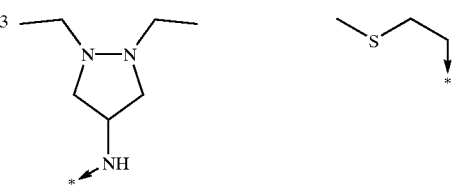 | 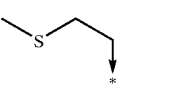 | 4.7 | 524.3 |
| 64 | 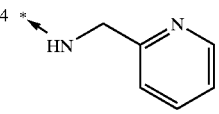 | 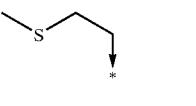 | 4.9 | 489.3 |

-continued
| | | | | |
|---|---|---|---|---|
| 65 | 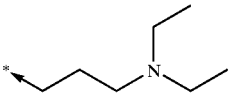 | 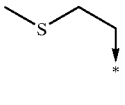 | 4.6 | 511.3 |
| 66 | 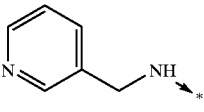 | 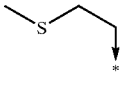 | 4.6 | 489.3 |
| 67 | 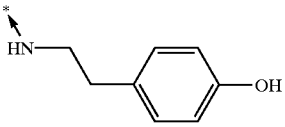 | 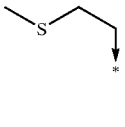 | 5.7 | 518.3 |
| 68 | 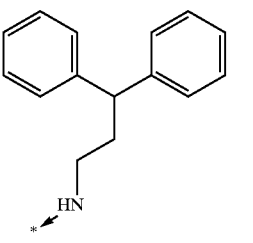 | 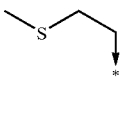 | 7.1 | 592.3 |
| 69 | 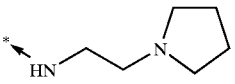 | 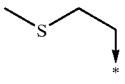 | 4.6 | 495.3 |
| 70 | 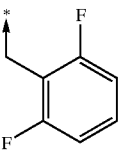 | 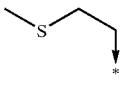 | 6.2 | 524.3 |
| 71 | 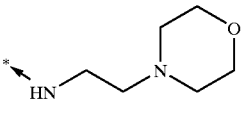 | 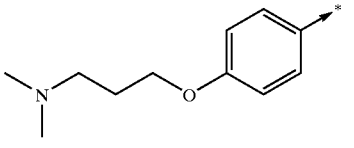 | 4.1 | 614.4 |
| 72 | 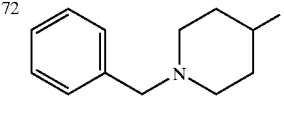 | 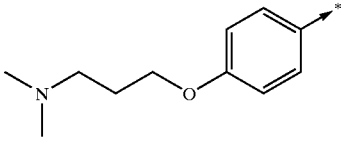 | 4.5 | 674.4 |
| 73 | 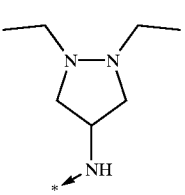 | 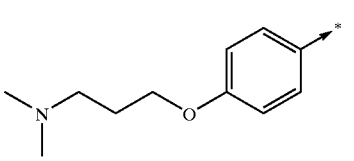 | 4.3 | 627.4 |
| 74 | 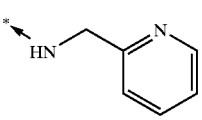 | 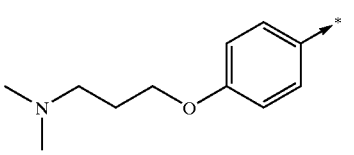 | 4.4 | 592.3 |

-continued

| | | | Rt | (M+H)+ |
|---|---|---|---|---|
| 75 | *N(Et)₂ sidechain | dimethylaminopropoxy-phenyl | 4.2 | 614.4 |
| 76 | pyridin-3-yl-CH₂-NH- | dimethylaminopropoxy-phenyl | 4.2 | 592.3 |
| 77 | 4-hydroxyphenethyl-NH- | dimethylaminopropoxy-phenyl | 4.9 | 621.4 |
| 78 | 3,3-diphenylpropyl-NH- | dimethylaminopropoxy-phenyl | 6.1 | 695.4 |
| 79 | 2-(pyrrolidin-1-yl)ethyl-NH- | dimethylaminopropoxy-phenyl | 4.2 | 598.4 |
| 80 | 2,6-difluorobenzyl- | dimethylaminopropoxy-phenyl | 5.3 | 627.3 |

FORMULA 2

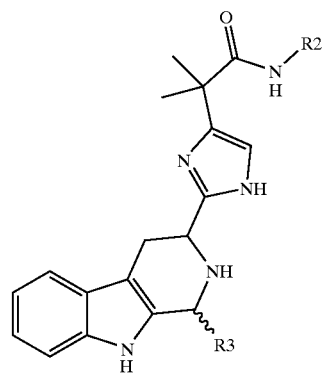

| | | Analyses | |
|---|---|---|---|
| R2 | R3 | Rt (min) | (M + H)+ |
| 1 imidazol-1-yl-propyl | n-butyl | 4.8 | 488.4 |

-continued

| # | R1 | R2 | t | MS |
|---|---|---|---|---|
| 2 | butyl-imidazole | propyl | 4.6 | 474.4 |
| 3 | butyl-imidazole | benzyloxymethyl | 5.2 | 552.4 |
| 4 | butyl-imidazole | 2-methoxy-3-nitrophenyl | 5.2; 5.1 | 583.3 |
| 5 | butyl-imidazole | benzo[1,3]dioxol-5-yl | 4.8 | 552.3 |
| 6 | butyl-imidazole | 4-tert-butylphenyl | 5.7 | 564.4 |
| 7 | butyl-imidazole | 3-methoxyphenyl | 4.9 | 538.4 |
| 8 | butyl-imidazole | 2-methoxyphenyl | 4.9 | 538.4 |
| 9 | butyl-imidazole | 3-bromophenyl | 5.3 | 586.2 |
| 10 | butyl-imidazole | cyclohexyl | 5.0 | 514.4 |
| 11 | butyl-imidazole | 2-(methylthio)ethyl | 4.7 | 506.4 |
| 12 | butyl-imidazole | 4-nitrophenyl | 5.1 | 553.3 |
| 13 | butyl-imidazole | 4-(methylthio)phenyl | 5.2 | 554.3 |

-continued
| | | | | |
|---|---|---|---|---|
| 14 | 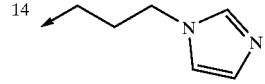 | 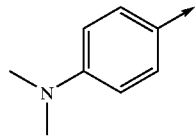 | 4.5 | 551.4 |
| 15 | 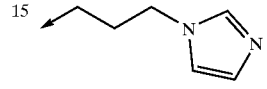 | 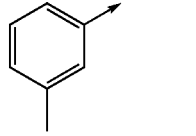 | 5.0 | 522.4 |
| 16 | 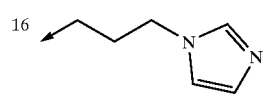 | 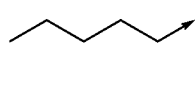 | 5.1 | 502.4 |
| 17 | 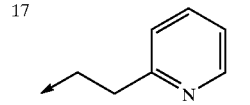 | 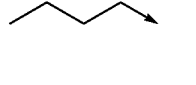 | 4.9 | 485.4 |
| 18 | 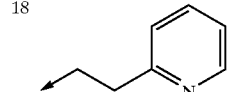 | 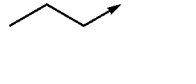 | 4.6 | 471.4 |
| 19 | 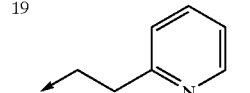 | 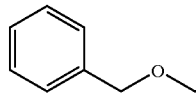 | 5.3 | 549.4 |
| 20 | 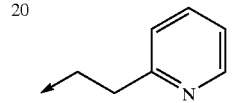 | 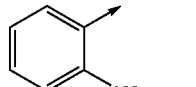 | 5.3; 5.2 | 580.3 |
| 21 | 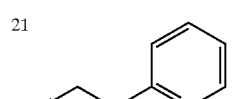 | 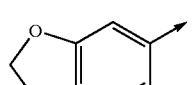 | 4.9 | 549.3 |
| 22 | 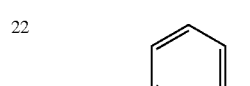 | 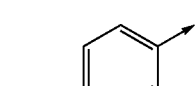 | 5.8 | 561.4 |
| 23 |  | 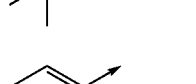 | 4.9 | 535.4 |
| 24 | 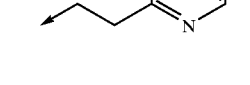 | 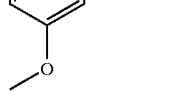 | 4.9 | 535.4 |

-continued
| | | | | |
|---|---|---|---|---|
| 25 | 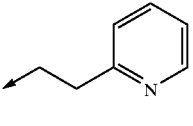 | 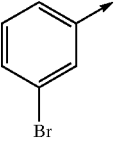 | 5.3 | 583.2 |
| 26 | 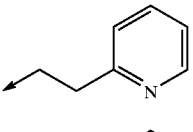 | 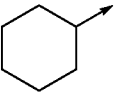 | 5.1 | 511.4 |
| 27 | 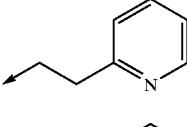 | 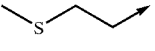 | 4.8 | 503.4 |
| 28 | 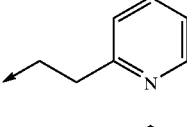 | 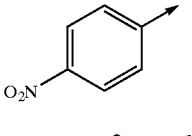 | 5.1 | 550.3 |
| 29 | 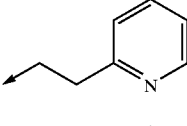 | 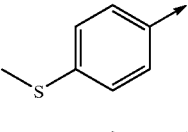 | 5.2 | 551.3 |
| 30 | 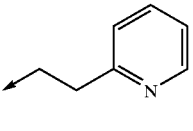 | 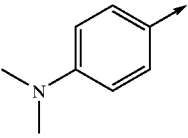 | 4.6 | 548.4 |
| 31 | 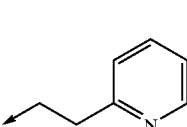 | 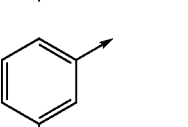 | 5.1 | 519.4 |
| 32 | 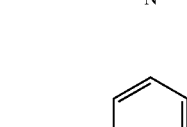 | 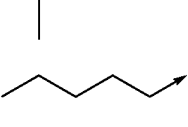 | 5.1 | 499.4 |
| 33 | 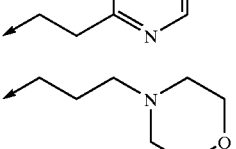 | 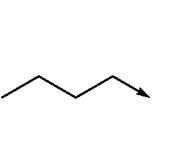 | 4.8 | 507.4 |
| 34 | 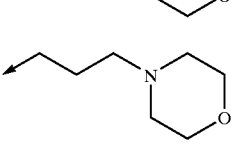 | 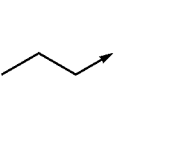 | 4.6 | 493.4 |
| 35 | 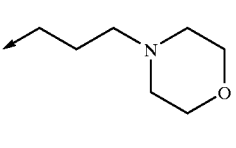 | 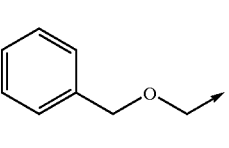 | 5.2 | 571.4 |
| 36 | 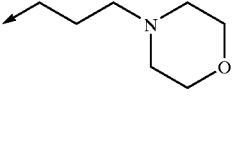 | 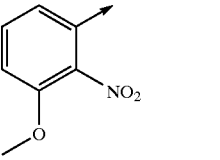 | 5.2; 5.1 | 602.4 |

-continued
| | | | | |
|---|---|---|---|---|
| 37 | 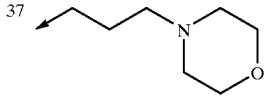 | 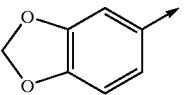 | 4.9 | 571.4 |
| 38 | 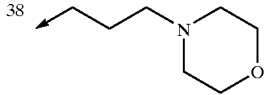 | 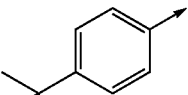 | 5.7 | 583.4 |
| 39 | 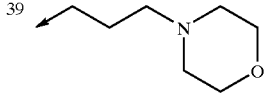 | 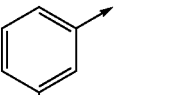 | 4.9 | 557.4 |
| 40 | 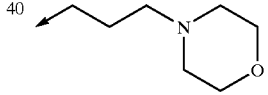 | 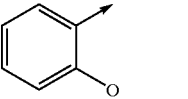 | 4.9 | 557.4 |
| 41 | 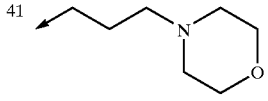 | 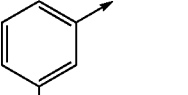 | 5.3 | 605.3 |
| 42 | 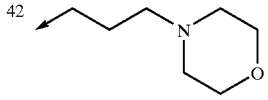 | 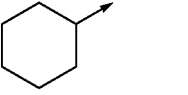 | 5.0 | 533.4 |
| 43 | 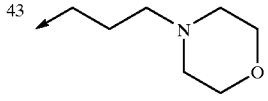 | 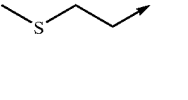 | 4.7 | 525.4 |
| 44 | 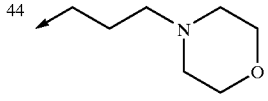 | 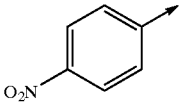 | 5.1 | 572.4 |
| 45 | 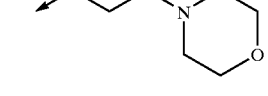 | 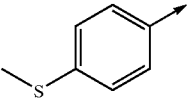 | 5.2 | 573.4 |
| 46 | 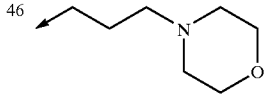 | 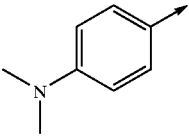 | 4.6 | 570.4 |
| 47 | 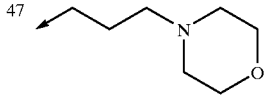 | 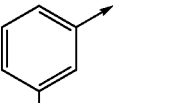 | 5.0 | 541.4 |

-continued
| | | | | |
|---|---|---|---|---|
| 48 | 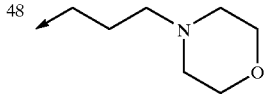 | 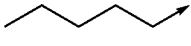 | 5.1 | 521.4 |
| 49 | 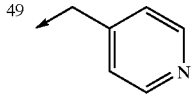 | 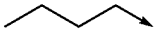 | 4.8 | 471.4 |
| 50 | 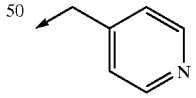 |  | 4.6 | 457.4 |
| 51 | 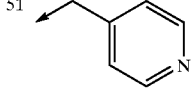 | 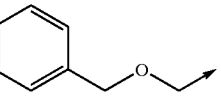 | 5.2 | 535.4 |
| 52 | 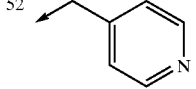 | 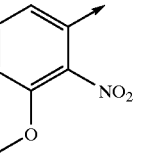 | 5.2; 5.1 | 566.3 |
| 53 | 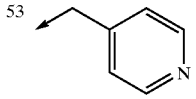 | 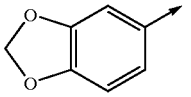 | 4.8 | 535.3 |
| 54 | 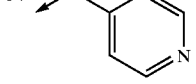 | 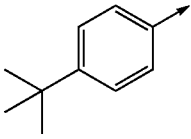 | 5.7 | 547.4 |
| 55 | 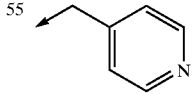 | 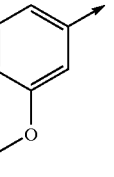 | 4.9 | 521.3 |
| 56 | 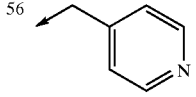 | 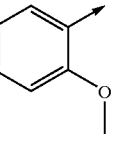 | 4.9 | 521.4 |
| 57 | 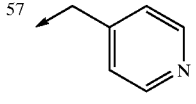 | 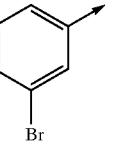 | 5.2 | 569.2 |
| 58 | 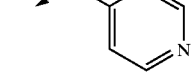 | 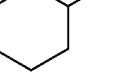 | 5.0 | 497.4 |
| 59 | 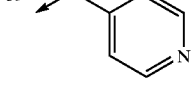 | 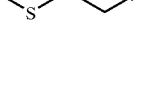 | 4.7 | 489.3 |

| | | | |
|---|---|---|---|
| 60 | 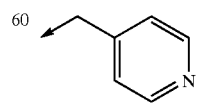 | 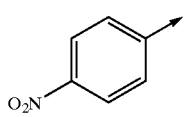 | 5.1 536.3 |
| 61 | 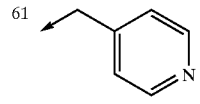 | 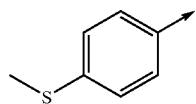 | 5.2 537.3 |
| 62 | 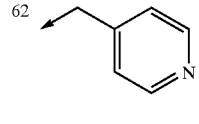 | 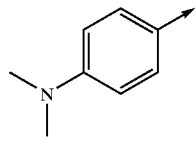 | 4.6 534.4 |
| 63 | 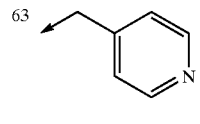 | 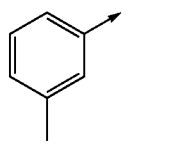 | 5.0 505.4 |
| 64 | 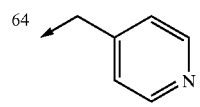 | 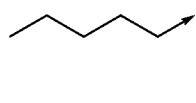 | 5.1 485.4 |
| 65 | 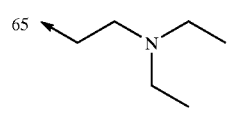 | 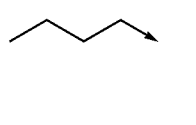 | 4.9 479.5 |
| 66 | 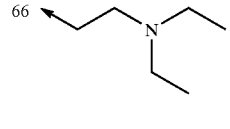 | 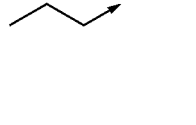 | 4.7 465.4 |
| 67 | 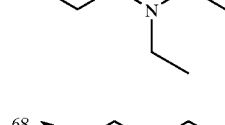 | 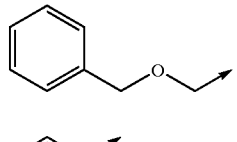 | 5.3 543.4 |
| 68 | 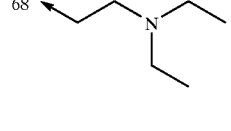 | 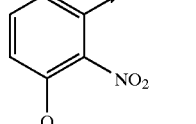 | 5.2; 5.3 574.4 |
| 69 | 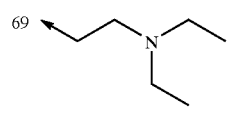 | 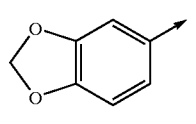 | 4.9 543.4 |
| 70 | 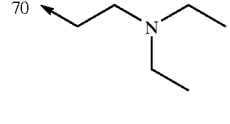 | 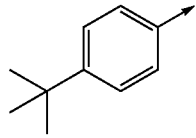 | 5.8 555.5 |

-continued

| | | | | |
|---|---|---|---|---|
| 71 | ◄╲N╱╲ (diethylaminoethyl) | 3-methoxyphenyl → | 5.0 | 529.5 |
| 72 | ◄╲N╱╲ | 2-methoxyphenyl → | 5.0 | 529.4 |
| 73 | ◄╲N╱╲ | 3-bromophenyl → | 5.3 | 577.3 |
| 74 | ◄╲N╱╲ | cyclohexyl → | 5.1 | 505.5 |
| 75 | ◄╲N╱╲ | $CH_3S$-ethyl → | 4.8 | 497.4 |
| 76 | ◄╲N╱╲ | 4-nitrophenyl → | 5.2 | 544.4 |
| 77 | ◄╲N╱╲ | 4-(methylthio)phenyl → | 5.3 | 545.4 |
| 78 | ◄╲N╱╲ | 4-(dimethylamino)phenyl → | 4.7 | 542.5 |
| 79 | ◄╲N╱╲ | 3-methylphenyl → | 5.1 | 513.5 |
| 80 | ◄╲N╱╲ | n-pentyl → | 5.2 | 493.5 |

-continued
FORMULA 3
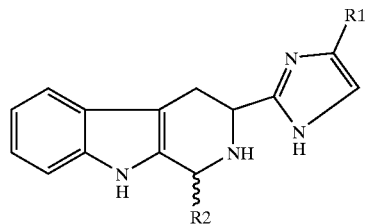
| R1 | R2 | Analyses | |
|---|---|---|---|
| | | Rt (min) | (M + H)+ |
| 1 (S) phenyl | 4-Cl-3-NO₂-phenyl | 6.7 | 470.1 |
| 2 (S) phenyl | 3-NO₂-phenyl | 6.4 | 436.1 |
| 3 (S) phenyl | 3-CN-phenyl | 6.2 | 416.1 |
| 4 (S) phenyl | 2,5-dimethoxyphenyl | 6.4 | 451.2 |
| 5 (S) phenyl | 2,3-methylenedioxyphenyl | 6.3 | 435.1 |
| 6 (S) phenyl | 2,3-dimethoxyphenyl | 6.4 | 451.2 |
| 7 (S) phenyl | 3-F-phenyl | 6.3 | 409.1 |

| | | | |
|---|---|---|---|
| 8 | 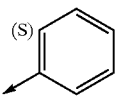 | 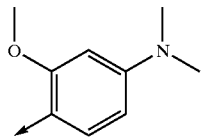 | 6.4 | 464.2 |
| 9 | 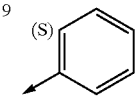 | 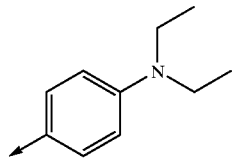 | 5.5; 5.3 | 462.2 |
| 10 | 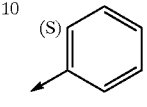 | 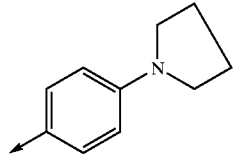 | 6.9 | 460.2 |
| 11 | 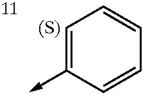 | 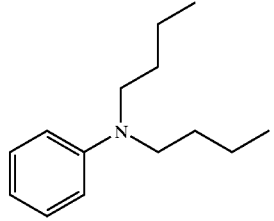 | 7.4; 7.2 | 518.3 |
| 12 | 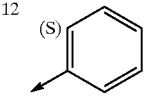 | 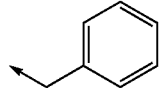 | 6.4 | 405.2 |
| 13 | 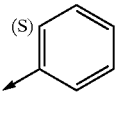 | 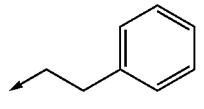 | 6.7; 6.6 | 419.2 |
| 14 | 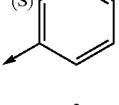 | 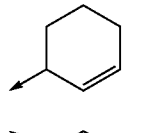 | 6.5; 6.4 | 395.2 |
| 15 | 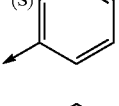 |  | 6.6 | 385.2 |
| 16 | 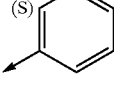 |  | 6.9 | 399.2 |
| 17 | 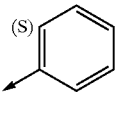 | 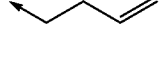 | 6.2 | 369.2 |
| 18 | 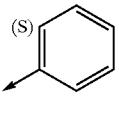 | 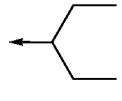 | 6.5; 6.4 | 385.2 |

-continued
| | | | | |
|---|---|---|---|---|
| 19 | 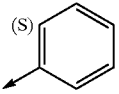 (S) | 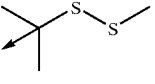 | 6.9 | 435.1 |
| 20 | 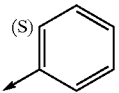 (S) | 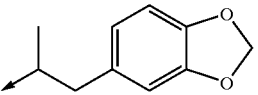 | 6.9 | 477.2 |
| 21 | 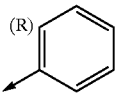 (R) | 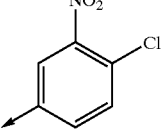 | 6.7 | 470.1 |
| 22 | 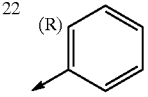 (R) | 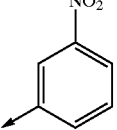 | 6.3 | 436.1 |
| 23 | 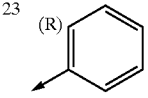 (R) | 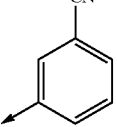 | 6.2 | 416.2 |
| 24 | 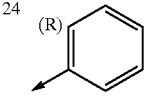 (R) | 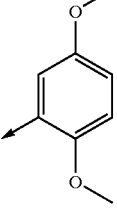 | 6.4 | 451.2 |
| 25 | 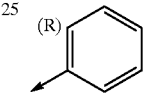 (R) | 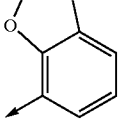 | 6.2 | 435.2 |
| 26 | 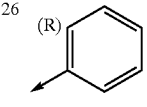 (R) | 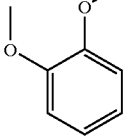 | 6.4 | 451.2 |
| 27 | 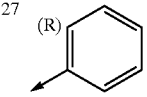 (R) | 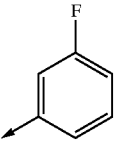 | 6.3 | 409.2 |
| 28 | 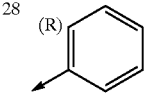 (R) | 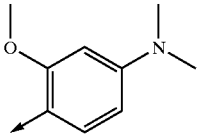 | 6.4 | 464.2 |

-continued

| | (R) group | Other group | Values | MW |
|---|---|---|---|---|
| 29 | phenyl | 4-(N,N-diethylamino)phenyl | 5.5; 5.3 | 462.2 |
| 30 | phenyl | 4-(pyrrolidin-1-yl)phenyl | 6.9 | 460.2 |
| 31 | phenyl | N,N-dibutylanilino | 7.4; 7.2 | 518.3 |
| 32 | phenyl | benzyl | 6.4 | 405.2 |
| 33 | phenyl | 2-phenylethyl | 6.7; 6.6 | 419.2 |
| 34 | phenyl | cyclohex-2-enyl | 6.5; 6.4 | 395.2 |
| 35 | phenyl | n-pentyl | 6.6 | 385.2 |
| 36 | phenyl | n-hexyl | 6.9 | 399.2 |
| 37 | phenyl | but-3-enyl | 6.2 | 369.2 |
| 38 | phenyl | 3-pentyl | 6.5; 6.4 | 385.2 |
| 39 | phenyl | tert-butyl methyl disulfide | 6.9 | 435.1 |
| 40 | phenyl | 2-(benzo[d][1,3]dioxol-5-yl)propyl | 6.9 | 477.2 |

-continued

| | | | |
|---|---|---|---|
| 41 (S) | 4-Cl-3-NO₂-phenyl | 6.6 | 450.1 |
| 42 (S) | 3-NO₂-phenyl | 6.3 | 416.2 |
| 43 (S) | 3-CN-phenyl | 6.1; 6.0 | 396.2 |
| 44 (S) | 2,5-dimethoxyphenyl | 6.1 | 431.2 |
| 45 (S) | benzo[1,3]dioxol-4-yl | 6.1 | 415.2 |
| 46 (S) | 2,3-dimethoxyphenyl | 6.1 | 431.2 |
| 47 (S) | 3-F-phenyl | 6.24; 6.17 | 389.2 |
| 48 (S) | 3-methoxy-4-(dimethylamino)phenyl | 5.6 | 444.2 |
| 49 (S) | 4-(diethylamino)phenyl | 5.1; 5.0 | 442.3 |

-continued
| | | | |
|---|---|---|---|
| 50 (S)  | 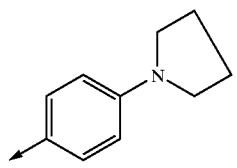 | 6.4 | 440.2 |
| 51 (S)  | 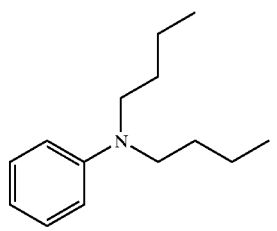 | 6.8 | 498.3 |
| 52 (S)  | 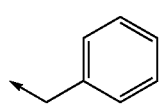 | 6.1 | 385.2 |
| 53 (S)  |  | 6.5 | 399.2 |
| 54 (S)  | 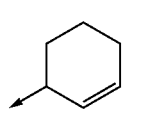 | 6.2; 6.3 | 375.2 |
| 55 (S)  | 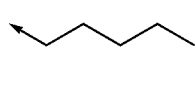 | 6.2 | 365.3 |
| 56 (S)  | 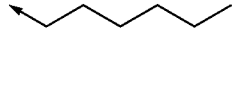 | 6.6 | 379.3 |
| 57 (S)  | 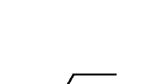 | 5.8 | 349.2 |
| 58 (S)  | 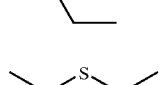 | 6.2 | 365.3 |
| 59 (S)  | 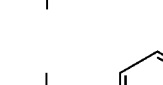 | 6.8 | 415.1 |
| 60 (S)  | 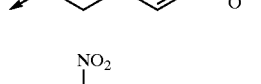 | 6.8 | 457.2 |
| 61 (R)  | 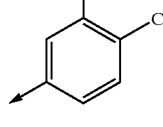 | 6.6 | 450.1 |

-continued
| | | | |
|---|---|---|---|
| 62 (R) | 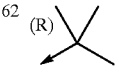 | 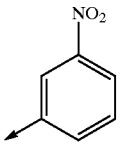 | 6.3 | 416.2 |
| 63 (R) | 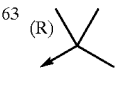 | 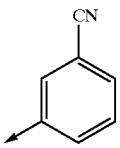 | 6.0; 6.1 | 396.2 |
| 64 (R) | 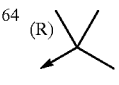 | 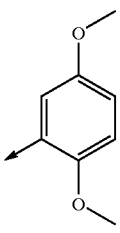 | 6.1 | 431.2 |
| 65 (R) | 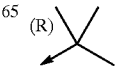 | 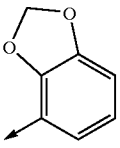 | 6.1 | 415.2 |
| 66 (R) | 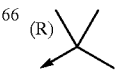 | 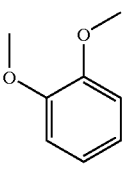 | 6.1 | 431.2 |
| 67 (R) | 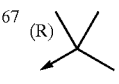 | 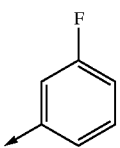 | 6.23; 6.17 | 389.2 |
| 68 (R) | 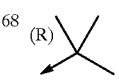 | 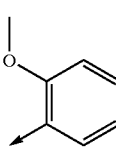 | 5.7 | 444.3 |
| 69 (R) | 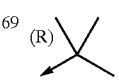 | 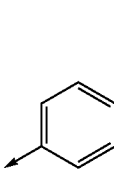 | 5.0; 5.1 | 442.3 |
| 70 (R) | 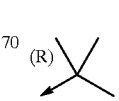 | 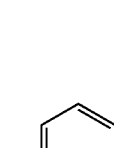 | 6.4 | 440.2 |

US 6,586,445 B1
-continued
| | | | 6.8 | 498.3 |
|---|---|---|---|---|
| 71 (R) | | | 6.8 | 498.3 |
| 72 (R) | | | 6.1 | 385.2 |
| 73 (R) | | | 6.5 | 399.2 |
| 74 (R) | | | 6.2 | 365.3 |
| 75 (R) | | | 6.6 | 379.3 |
| 76 (R) | | | 5.8 | 349.2 |
| 77 (R) | | | 6.2 | 365.3 |
| 78 (R) | | | 6.8 | 415.1 |
| 79 (R) | | | 6.8 | 457.2 |
FORMULA 4
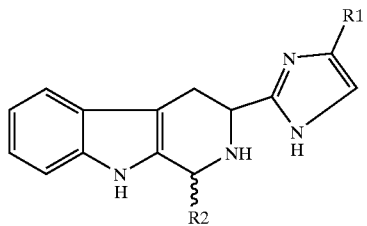
| | | Analyses | |
|---|---|---|---|
| R1 | R2 | Rt (min) | (M + H)+ |
| 1 (S) | | 6.2 | 451.2 |

-continued
| | | | | |
|---|---|---|---|---|
| 2 | 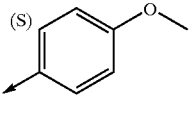 | 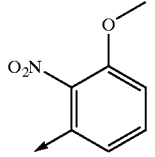 | 6.4 | 496.3 |
| 3 | 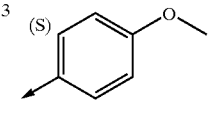 | 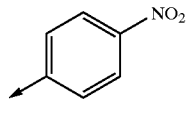 | 6.3 | 466.3 |
| 4 | 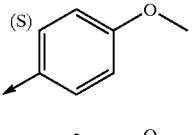 | 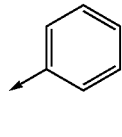 | 6.1 | 421.3 |
| 5 | 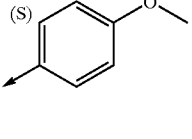 | 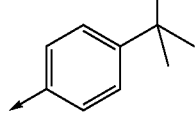 | 7.0 | 477.4 |
| 6 | 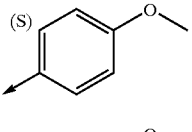 | 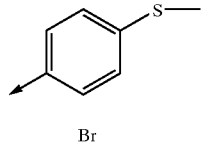 | 6.5 | 467.3 |
| 7 | 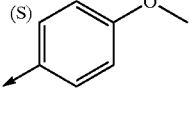 | 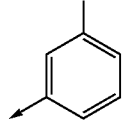 | 6.5 | 499.2 |
| 8 | 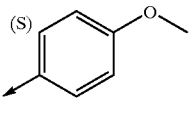 | 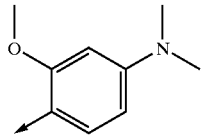 | 6.1 | 494.4 |
| 9 | 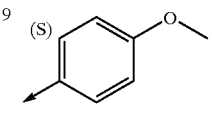 | 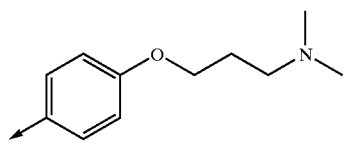 | 5.2 | 522.4 |
| 10 | 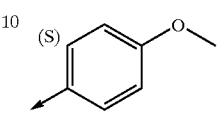 | 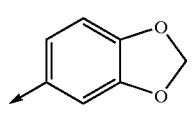 | 6.1 | 465.3 |
| 11 | 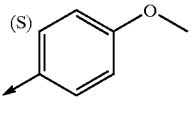 | 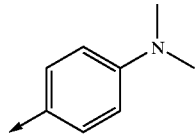 | 5.8 | 464.4 |
| 12 | 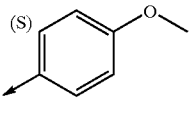 | 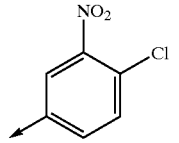 | 6.6 | 500.3 |

-continued
| | | | | |
|---|---|---|---|---|
| 13 | (S) 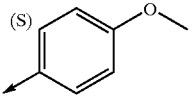 | 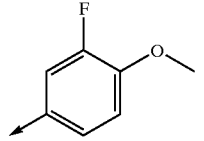 | 6.3 | 469.3 |
| 14 | (S) 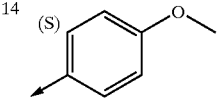 | 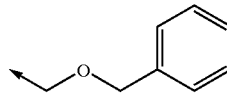 | 6.5 | 465.3 |
| 15 | (S) 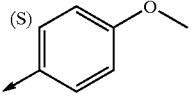 | 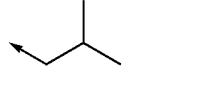 | 6.1 | 401.4 |
| 16 | (S) 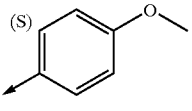 | 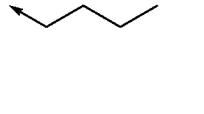 | 6.2 | 401.3 |
| 17 | (S) 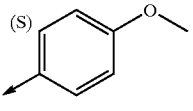 | 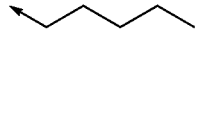 | 6.5 | 415.4 |
| 18 | (S) 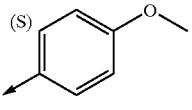 | 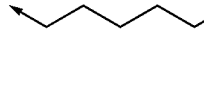 | 6.7 | 429.4 |
| 19 | (S) 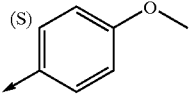 | 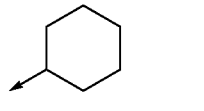 | 6.4; 5.9 | 427.4 |
| 20 | (S) 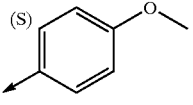 | 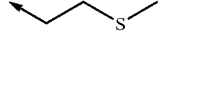 | 6.0 | 419.3 |
| 21 | (R) 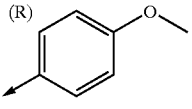 | 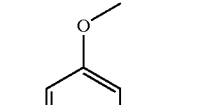 | 6.2 | 451.3 |
| 22 | (R) 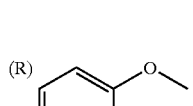 | 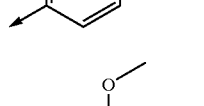 | 6.4 | 496.3 |
| 23 | (R) 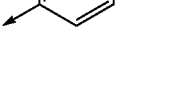 | 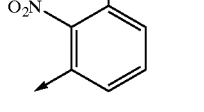 | 6.3 | 466.3 |
| 24 | (R) 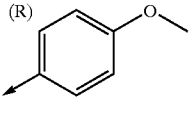 | 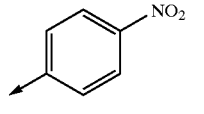 | 6.1 | 421.3 |

-continued
| | | | | |
|---|---|---|---|---|
| 25 (R) | 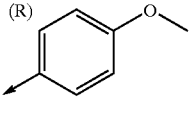 | 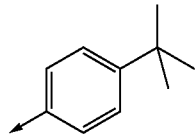 | 7.0 | 477.4 |
| 26 (R) | 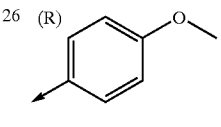 | 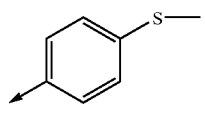 | 6.5 | 467.3 |
| 27 (R) | 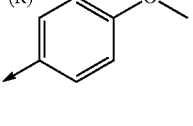 | 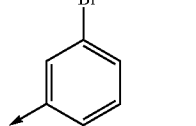 | 6.5 | 499.2 |
| 28 (R) | 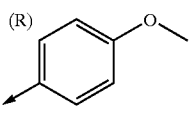 | 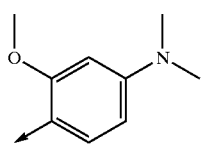 | 6.2 | 494.4 |
| 29 (R) | 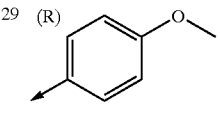 | 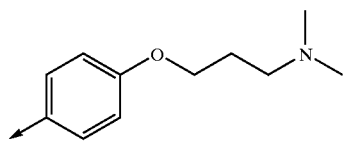 | 5.2 | 522.4 |
| 30 (R) | 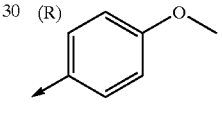 | 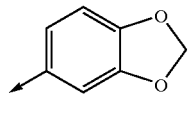 | 6.1 | 465.3 |
| 31 (R) | 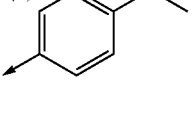 | 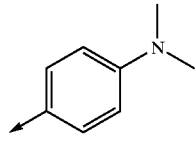 | 5.8 | 464.4 |
| 32 (R) | 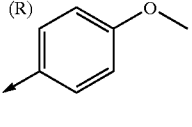 | 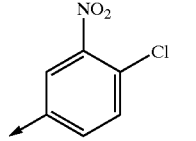 | 6.6 | 500.3 |
| 33 (R) | 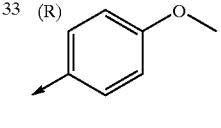 | 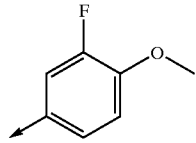 | 6.3 | 469.3 |
| 34 (R) | 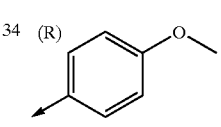 | 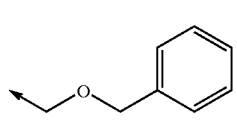 | 6.5 | 465.3 |
| 35 (R) | 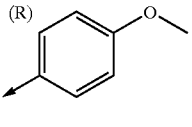 | 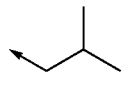 | 6.1 | 401.3 |

-continued

| # | R1 | R2 | (min) | MS |
|---|---|---|---|---|
| 36 (R) | 4-methoxyphenyl | pentyl | 6.2 | 401.3 |
| 37 (R) | 4-methoxyphenyl | hexyl | 6.5 | 415.3 |
| 38 (R) | 4-methoxyphenyl | heptyl | 6.7 | 429.4 |
| 39 (R) | 4-methoxyphenyl | cyclohexyl | 6.4; 5.9 | 427.4 |
| 40 (R) | 4-methoxyphenyl | 2-(methylthio)ethyl | 6.1 | 419.3 |
| 41 (S) | 4-nitrophenyl | 3-methoxyphenyl | 6.4 | 466.3 |
| 42 (S) | 4-nitrophenyl | 2-methoxy-3-nitrophenyl | 6.8 | 511.3 |
| 43 (S) | 4-nitrophenyl | 4-nitrophenyl | 6.5 | 481.3 |
| 44 (S) | 4-nitrophenyl | phenyl | 6.3 | 436.3 |
| 45 (S) | 4-nitrophenyl | 4-tert-butylphenyl | 7.1 | 492.4 |
| 46 (S) | 4-nitrophenyl | 4-(methylthio)phenyl | 6.6 | 482.3 |

-continued

| # | R1 | R2 | t | M |
|---|---|---|---|---|
| 47 | 4-nitrophenyl (S) | 3-bromophenyl | 6.7 | 514.2 |
| 48 | 4-nitrophenyl (S) | 3-methoxy-4-(dimethylamino)phenyl | 6.6 | 509.3 |
| 49 | 4-nitrophenyl (S) | 4-(3-(dimethylamino)propoxy)phenyl | 5.4 | 537.4 |
| 50 | 4-nitrophenyl (S) | benzo[1,3]dioxol-5-yl | 6.3 | 480.3 |
| 51 | 4-nitrophenyl (S) | 4-(dimethylamino)phenyl | 6.4 | 479.3 |
| 52 | 4-nitrophenyl (S) | 4-chloro-3-nitrophenyl | 6.9 | 515.2 |
| 53 | 4-nitrophenyl (S) | 3-fluoro-4-methoxyphenyl | 6.5 | 484.3 |
| 54 | 4-nitrophenyl (S) | benzyloxymethyl | 6.7 | 480.3 |
| 55 | 4-nitrophenyl (S) | isobutyl | 6.3 | 416.3 |
| 56 | 4-nitrophenyl (S) | n-butyl | 6.4 | 416.3 |

-continued
| | | | | |
|---|---|---|---|---|
| 57 | 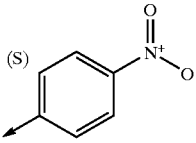 (S) | 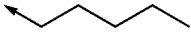 | 6.7 | 430.3 |
| 58 | 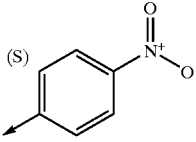 (S) |  | 6.9 | 444.4 |
| 59 | 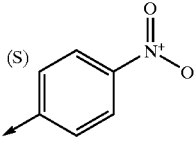 (S) |  | 6.6; 6.4 | 442.3 |
| 60 | 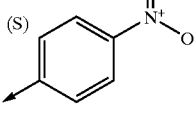 (S) |  | 6.3 | 434.3 |
| 61 | 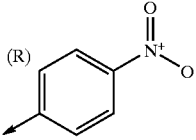 (R) | 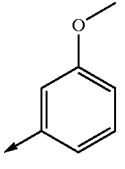 | 6.4 | 466.3 |
| 62 | 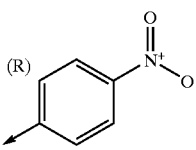 (R) | 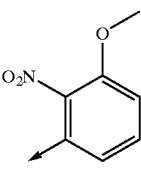 | 6.8 | 511.3 |
| 63 | 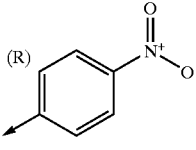 (R) | 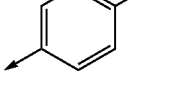 | 6.5 | 481.3 |
| 64 | 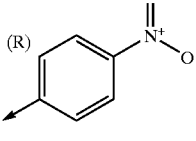 (R) |  | 6.3 | 436.3 |
| 65 | 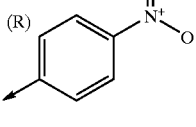 (R) | 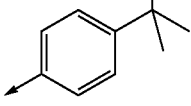 | 7.1 | 492.4 |

-continued
| | | | | |
|---|---|---|---|---|
| 66 | 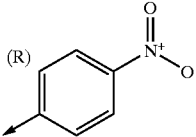 | 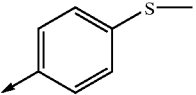 | 6.6 | 482.3 |
| 67 | 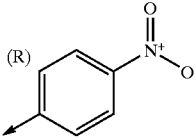 | 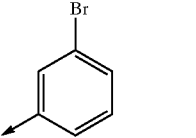 | 6.7 | 514.2 |
| 68 | 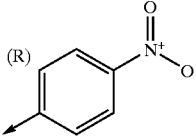 | 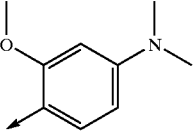 | 6.6 | 509.3 |
| 69 | 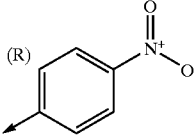 | 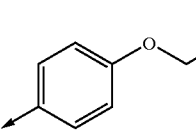 | 5.4 | 537.4 |
| 70 | 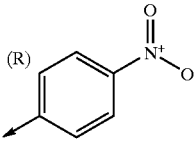 | 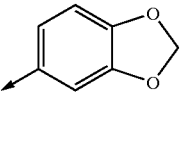 | 6.3 | 480.3 |
| 71 | 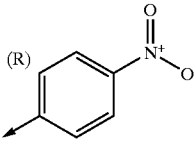 | 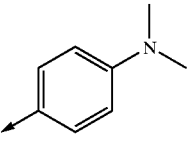 | 6.4 | 479.3 |
| 72 | 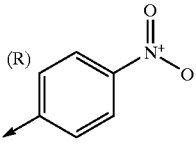 | 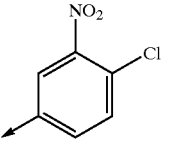 | 6.9 | 515.2 |
| 73 | 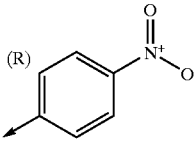 | 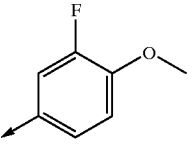 | 6.5 | 484.3 |
| 74 | 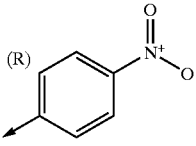 | 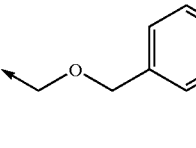 | 6.7 | 480.3 |
| 75 | 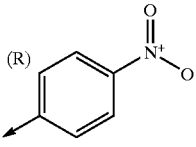 | 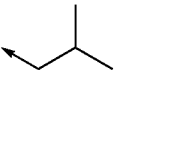 | 6.3 | 416.3 |

-continued
| | | | | |
|---|---|---|---|---|
| 76 | 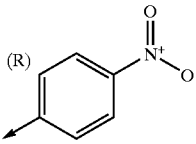 | 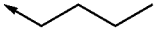 | 6.4 | 416.3 |
| 77 | 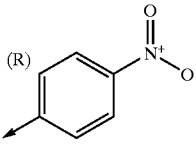 | 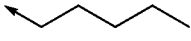 | 6.7 | 430.4 |
| 78 | 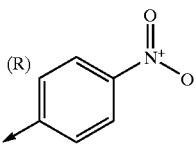 |  | 6.9 | 444.4 |
| 79 | 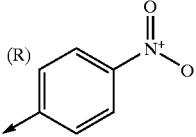 | 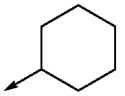 | 6.6; 6.3 | 442.3 |
| 80 | 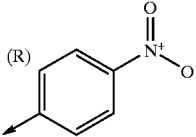 | 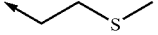 | 6.3 | 434.3 |
FORMULA 5
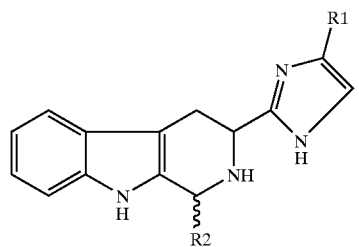
| | | Analyses | |
|---|---|---|---|
| R1 | R2 | Rt (min) | (M + H)+ |
| 1 | 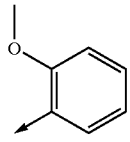 | 5.4 | 421.1 |
| 2 | 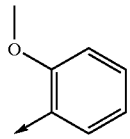 | 5.4 | 421.1 |

-continued

| | | | |
|---|---|---|---|
| 3 (S) Ph | 3-methoxyphenyl | 5.4 | 421.1 |
| 4 (R) Ph | 3-methoxyphenyl | 5.4 | 421.1 |
| 5 (S) Ph | 4-methoxyphenyl | 5.4 | 421.1 |
| 6 (R) Ph | 4-methoxyphenyl | 5.4 | 421.1 |
| 7 (S) Ph | 3,4,5-trimethoxyphenyl | 5.3 | 481.1 |
| 8 (R) Ph | 3,4,5-trimethoxyphenyl | 5.3 | 481.1 |
| 9 (S) Ph | 3,4-methylenedioxyphenyl | 5.3 | 435.1 |
| 10 (R) Ph | 3,4-methylenedioxyphenyl | 5.4 | 435.1 |
| 11 (S) Ph | 6-nitro-3,4-methylenedioxyphenyl | 5.4 | 480.1 |
| 12 (R) Ph | 6-nitro-3,4-methylenedioxyphenyl | 5.4 | 480.1 |

-continued

| | | | | |
|---|---|---|---|---|
| 13 | (S) phenyl | 2-methoxy-3-nitrophenyl (O₂N, OMe) | 5.5 | 466.1 |
| 14 | (R) phenyl | 2-methoxy-3-nitrophenyl (O₂N, OMe) | 5.5 | 466.1 |
| 15 | (S) phenyl | 4-butoxyphenyl | 5.7 | 463.2 |
| 16 | (R) phenyl | 4-butoxyphenyl | 5.7 | 463.2 |
| 17 | (S) phenyl | 3-ethoxy-4-methoxyphenyl | 5.4 | 465.1 |
| 18 | (R) phenyl | 3-ethoxy-4-methoxyphenyl | 5.4 | 465.1 |
| 19 | (S) phenyl | 2-nitrophenyl (O₂N) | 5.4 | 436.1 |
| 20 | (R) phenyl | 2-nitrophenyl (O₂N) | 5.4 | 436.1 |
| 21 | (S) phenyl | 4-nitrophenyl (NO₂) | 5.4 | 436.1 |
| 22 | (R) phenyl | 4-nitrophenyl (NO₂) | 5.4 | 436.1 |
| 23 | (S) phenyl | 4-OCF₂-phenyl | 5.6 | 475.1 |

-continued
| | | | | |
|---|---|---|---|---|
| 24 | 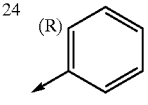 (R) | 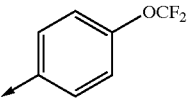 OCF₂ | 5.6 | 475.1 |
| 25 | 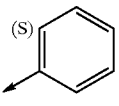 (S) | 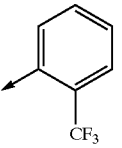 CF₃ | 5.5 | 459.1 |
| 26 | 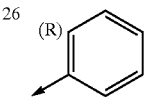 (R) | 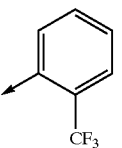 CF₃ | 5.5 | 459.1 |
| 27 | 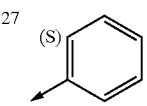 (S) | 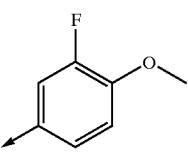 F, O | 5.4 | 439.1 |
| 28 | 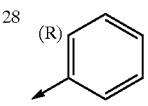 (R) | 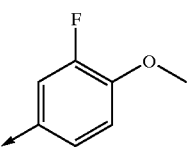 F, O | 5.4 | 439.1 |
| 29 | 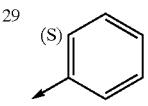 (S) | 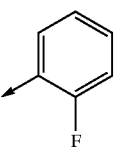 F | 5.4 | 409.1 |
| 30 | 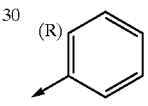 (R) | 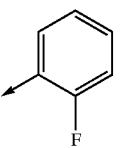 F | 5.4 | 409.1 |
| 31 | 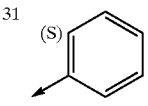 (S) | 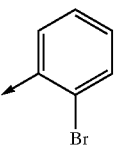 Br | 5.5 | 469.0 |
| 32 | 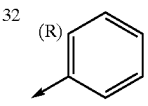 (R) | 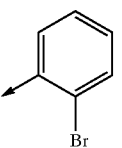 Br | 5.5 | 469.0 |
| 33 | 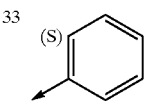 (S) | 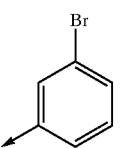 Br | 5.5 | 469.0 |

-continued
| | | | | |
|---|---|---|---|---|
| 34 | 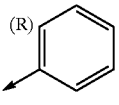 (R) | 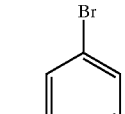 Br | 5.5 | 469.0 |
| 35 | 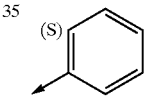 (S) | 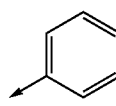 Br | 5.5 | 469.0 |
| 36 | 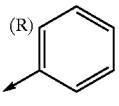 (R) | 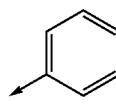 Br | 5.5 | 469.0 |
| 37 | 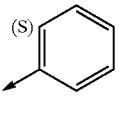 (S) | 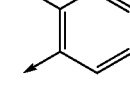 Cl, Cl | 5.6 | 459.0 |
| 38 | 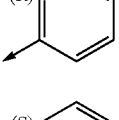 (R) | 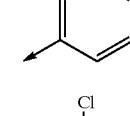 Cl, Cl | 5.6 | 459.0 |
| 39 | 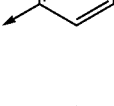 (S) | 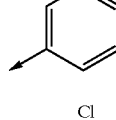 Cl, Cl | 5.6 | 459.0 |
| 40 | 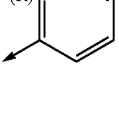 (R) | 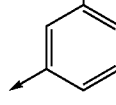 Cl, Cl | 5.6 | 459.0 |
| 41 | 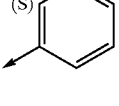 (S) | 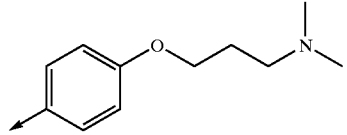 | 4.9 | 492.2 |
| 42 | 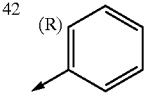 (R) | 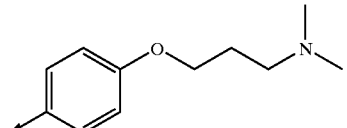 | 4.6 | 492.2 |
| 43 | 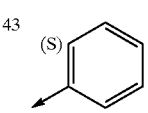 (S) | 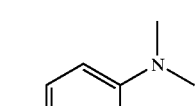 | 5.3 | 434.1 |
| 44 | 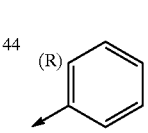 (R) | 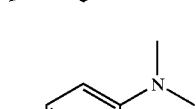 | 5.3 | 434.1 |

-continued

| | | | | |
|---|---|---|---|---|
| 45 | (S)-phenyl | 4-(N-acetylamino)phenyl | 5.1 | 448.1 |
| 46 | (R)-phenyl | 4-(N-acetylamino)phenyl | 5.1 | 448.1 |
| 47 | (S)-phenyl | 4-tert-butylphenyl | 5.7 | 447.2 |
| 48 | (R)-phenyl | 4-tert-butylphenyl | 5.7 | 447.2 |
| 49 | (S)-phenyl | 4-(tert-butylthio)phenyl | 5.6 | 479.1 |
| 50 | (R)-phenyl | 4-(tert-butylthio)phenyl | 5.6 | 479.1 |
| 51 | (S)-phenyl | 4-hydroxyphenyl | 5.2 | 407.1 |
| 52 | (R)-phenyl | 4-hydroxyphenyl | 5.2 | 407.1 |
| 53 | (S)-phenyl | 3-hydroxy-4-methoxyphenyl | 5.2 | 437.1 |
| 54 | (R)-phenyl | 3-hydroxy-4-methoxyphenyl | 5.2 | 437.1 |
| 55 | (S)-phenyl | 4-biphenyl | 5.6 | 467.1 |

-continued
| | | | | |
|---|---|---|---|---|
| 56 | 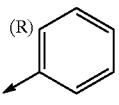 (R) | 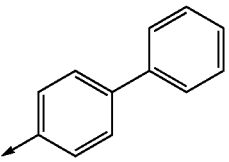 | 5.6 | 467.1 |
| 57 | 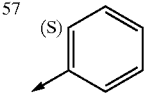 (S) | 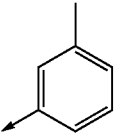 | 5.4 | 405.2 |
| 58 | 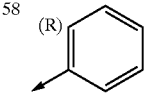 (R) | 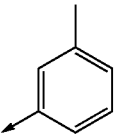 | 5.4 | 405.2 |
| 59 | 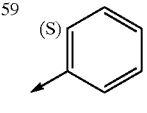 (S) | 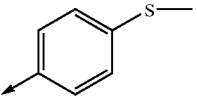 | 5.5 | 437.1 |
| 60 | 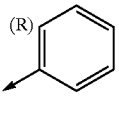 (R) | 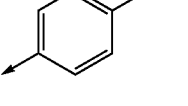 | 5.5 | 437.1 |
| 61 | 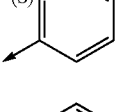 (S) | 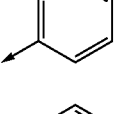 | 5.3 | 391.1 |
| 62 | 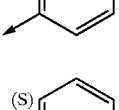 (R) | 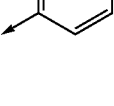 | 5.3 | 391.1 |
| 63 | 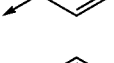 (S) | 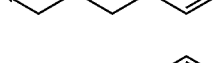 | 5.5 | 435.1 |
| 64 | 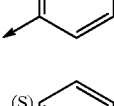 (R) | 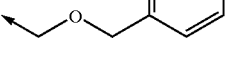 | 5.5 | 435.1 |
| 65 | 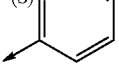 (S) | 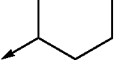 | 5.5 | 397.2 |
| 66 | 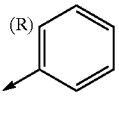 (R) | 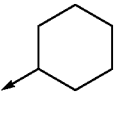 | 5.4 | 397.2 |
| 67 | 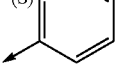 (S) |  | 5.1 | 355.2 |

-continued
| | | | | |
|---|---|---|---|---|
| 68 | 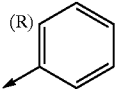 (R) |  | 5.1 | 355.2 |
| 69 | 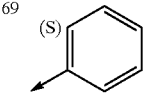 (S) | 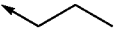 | 5.2 | 357.2 |
| 70 | 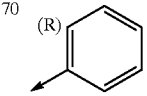 (R) | 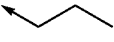 | 5.2 | 357.2 |
| 71 | 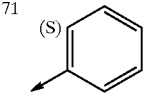 (S) | 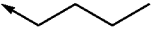 | 5.3 | 371.2 |
| 72 | 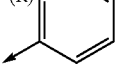 (R) |  | 5.3 | 371.2 |
| 73 | 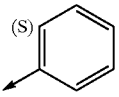 (S) | 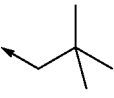 | 5.3 | 385.2 |
| 74 | 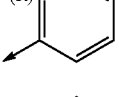 (R) | 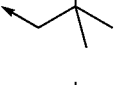 | 5.3 | 385.2 |
| 75 | 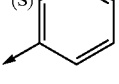 (S) | 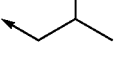 | 5.3 | 371.2 |
| 76 | 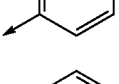 (R) | 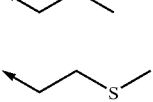 | 5.3 | 371.2 |
| 77 | 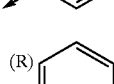 (S) |  | 5.3 | 389.1 |
| 78 | 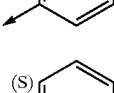 (R) |  | 5.3 | 389.1 |
| 79 | 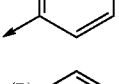 (S) |  | 5.6 | 413.2 |
| 80 | 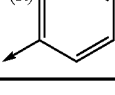 (R) |  | 5.7 | 413.2 |

What is claimed is:

1. A compound of formula (II),

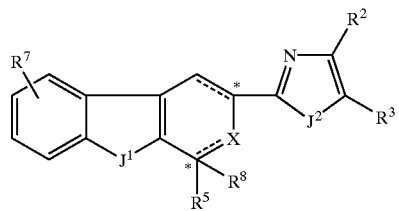

(II)

the racemic-diastereomeric mixtures and optical isomers of said compound of formula (II), and pharmaceutically-acceptable salts thereof,
wherein
- - - represents an optional bond;
$J^1$ is N—$R^6$;
$J^2$ is N—$R^1$, O or S;
X is N or N—$R^4$, where X is N when both optional bonds are present and X is N—$R^4$ when the optional bonds are not present;
$R^1$ is H, —$(CH_2)_m$—C(O)—$(CH_2)_m$—$Z^1$, —$(CH_2)_m$—$Z^1$, —$(CH_2)_m$—O—$Z^1$ or $(C_0$-$C_6)$alkyl-C(O)—NH—$(CH_2)_m$—$Z^3$;
$Z^1$ is an optionally substituted moiety selected from the group consisting of $(C_1$-$C_{12})$alkyl, benzo[b]thiophene, phenyl, naphthyl, benzo[b]furanyl, thiophene, isoxazolyl, indolyl,

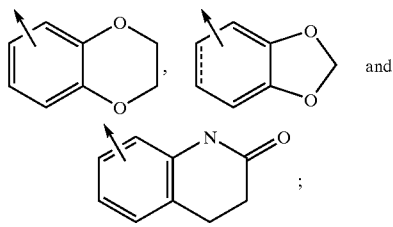

and

;

$R^2$ is $(C_1$-$C_{12})$alkyl, $(C_0$-$C_6)$alkyl-C(O)—O—$Z^5$, $(C_0$-$C_6)$alkyl-C(O)—NH—$(CH_2)_m$—$Z^3$ or optionally substituted phenyl;
$Z^5$ is H, $(C_1$-$C_{12})$alkyl or $(CH_2)_m$-aryl;
$Z^3$ is amino, $(C_1$-$C_{12})$alkylamino, N,N-di-$(C_1$-$C_{12})$alkylamino, —NH—C(O)—O—$(CH_2)_m$-phenyl, —NH—C(O)—O—$(CH_2)_m$—$(C_1$-$C_6)$alkyl or an optionally substituted moiety selected from the group consisting of phenyl, imidazolyl, pyridinyl and morpholinyl, piperidinyl, piperazinyl, pyrazolidinyl, furanyl and thiophene;
$R^3$ is H, $(C_1$-$C_6)$alkyl or optionally substituted phenyl;
$R^4$ is H, —C(=Y)—N($X^1X^2$), C(=O)$X^2$ or $X^2$;
Y is O or S;
$X^2$ is H or —$(CH_2)_m$—$Y^1$—$X^3$;
$X^3$ is H or an optionally substituted moiety selected from the group consisting of $(C_1$-$C_{12})$alkyl, $(C_3$-$C_8)$cycloalkyl, $(C_1$-$C_{12})$alkoxy, aryloxy, $(C_1$-$C_{12})$alkylamino, N,N-di-$(C_1$-$C_{12})$alkylamino, —CH-di-$(C_1$-$C_{12})$alkoxy or phenyl;
$R^5$ and $R^8$ are each independently selected from the group consisting of H, $(C_1$-$C_{12})$alkyl, —$(CH_2)_m$—$Y^1$—$(CH_2)_m$-phenyl-$(X^1)_n$, $(C_3$-$C_{12})$cycloalkyl, $(C_3$-$C_{12})$cycloalkenyl, —$(CH_2)_m$—S—$(C_1$-$C_{12})$alkyl, $(C_1$-$C_{12})$alkyl-S—S—$(C_1$-$C_{12})$alkyl, —$(CH_2)_m$—$(C_1$-$C_{12})$alkenyl and an optionally substituted moiety selected from the group consisting of phenyl, furanyl, thiophene, pyrrolyl, pyridinyl and

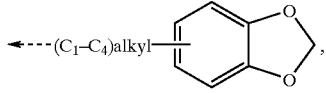, provided that $R^5$ and $R^8$ are not both H at the same time;
or $R^5$ and $R^8$ are taken together with the carbon atom to which they are attached to form

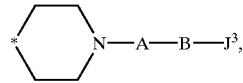, spiro($C_4$-$C_{12}$)cycloalkyl,

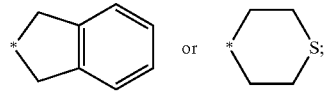;

$Y^1$ is O, S, NH or a bond;
A is a bond, —CO—, —C(O)O—, —C(O)NH—, —C(S)NH—, or —$SO_2$—;
B is a bond or —$(CH_2)_q$—, where q is an integer from 1 to 6;
$J^3$ is H, $(C_1$-$C_6)$alkyl, optionally substituted phenyl, optionally substituted heteroaryl or N($R^9R^{10}$), where $R^9$ and $R^{10}$ are each independently selected from the group consisting of $(C_1$-$C_6)$alkyl, and optionally substituted phenyl, or $R^9$ and $R^{10}$ are taken together with the nitrogen to which they are attached to form a ring having 5 to 8 members including the nitrogen atom that $R^9$ and $R^{10}$ are attached to, where one of the ring members may optionally be an oxygen atom or $NR^{11}$, where $R^{11}$ is $(C_1$-$C_6)$alkyl, —C(O)—$(C_1$-$C_6)$alkyl, —C(O)—N($V^1V^2$), —C(S)—N($V^1V^2$), or optionally-substituted-phenyl-$(C_0$-$C_6)$alkyl-, where $V^1$ and $V^2$ are each independently H, $(C_1$-$C_6)$alkyl or optionally-substituted-phenyl-$(C_0$-$C_6)$alkyl;
$R^6$ is H or $SO_2$-phenyl;
$R^7$ is H, Cl, F, Br, I, $CF_3$, $NO_2$, OH, $SO_2NH_2$, CN, $N_3$, —$OCF_3$, $(C_1$-$C_{12})$alkoxy, —$(CH_2)_m$-phenyl-$(X^1)_n$, —NH—CO—$(C_1$-$C_6)$alkyl, —S—$(C_1$-$C_{12})$alkyl, —S-phenyl-$(X^1)_n$, —O—$(CH_2)_m$-phenyl-$(X^1)_n$, —$(CH_2)_m$—C(O)—O—$(C_1$-$C_6)$alkyl, —$(CH_2)_m$—C(O)—$(C_1$-$C_6)$alkyl, —O—$(CH_2)_m$—$NH_2$, —O—$(CH_2)_m$—NH—$(C_1$-$C_6)$alkyl, —O—$(CH_2)_m$—N-di-(($C_1$-$C_6)$alkyl) and —$(C_0$-$C_{12})$alkyl-$(X^1)_n$;
wherein an optionally substituted moiety or optionally substituted phenyl is optionally substituted by one or more substituents, each independently selected from the group consisting of Cl, F, Br, I, $CF_3$, $NO_2$, OH, $SO_2NH_2$, CN, $N_3$, —$OCF_3$, $(C_1$-$C_{12})$alkoxy, —$(CH_2)_m$-phenyl-$(X^1)_n$, —NH—CO—$(C_1$-$C_6)$alkyl, —S—$(C_1$-$C_{12})$alkyl, —S-phenyl-$(X^1)_n$, —O—$(CH_2)_m$-phenyl-$(X^1)_n$, —$(CH_2)_m$—C(O)—O—$(C_1$-$C_6)$alkyl, —$(CH_2)_m$—C(O)—$(C_1$-$C_6)$alkyl, —O—$(CH_2)_m$—$NH_2$, —O—$(CH_2)_m$—NH—$(C_1$-$C_6)$alkyl, —O—$(CH_2)_m$—N-di-(($C_1$-$C_6)$alkyl) and —$(C_0$-$C_{12})$alkyl-$(X^1)_n$;

$X^1$ for each occurrence is independently selected from the group consisting of hydrogen, Cl, F, Br, I, $NO_2$, OH, $-CF_3$, $-OCF_3$, $(C_1-C_{12})$alkyl, $(C_1-C_{12})$alkoxy, $-S-(C_1-C_6)$alkyl, $-(CH_2)_m$-amino, $-(CH_2)_m-NH-(C_1-C_6)$alkyl, $-(CH_2)_m-N$-di-$((C_1-C_6)$alkyl), $-(CH_2)_m$-phenyl and $-(CH_2)_m-NH-(C_3-C_6)$cycloalkyl;

m for each occurrence is independently 0 or an integer from 1 to 6; and n for each occurrence is independently an integer from 1 to 5.

2. A compound according to claim 1 having the formula (IIa)

wherein $R^3$ is H or methyl;

$R^4$ is H or methyl;

$R^5$ is H, methyl, ethyl, butyl, pentyl or hexyl;

$R^8$ is ethyl, butyl, pentyl, hexyl, or cyclohexyl; or $R^5$ and $R^8$ are taken together with the carbon to which they are attached to form spirocyclohexyl, spirocycloheptyl, spiroadamantyl, or where A is a bond or $-C(O)O-$; B is a bond, $-(CH_2)-$ or $-(CH_2)_2-$; $J^3$ is H, or phenyl; and $R^7$ is H, Me, F, Cl, OH, $-O$-methyl or $-O-CH_2$-phenyl.

3. A compound according to claim 2 wherein:

$R^3$, $R^4$ and $R^7$ are each hydrogen, $R^5$ and $R^8$ are together and the imidazolyl is in the R-configuration;

$R^3$, $R^4$ and $R^7$ are each hydrogen, $R^5$ and $R^8$ are together and the imidazolyl is in the R-configuration;

$R^3$, $R^4$ and $R^7$ are each hydrogen, $R^5$ and $R^8$ are together and the imidazolyl is in the R-configuration;

$R^3$, $R^4$ and $R^7$ are each hydrogen, $R^5$ and $R^8$ are together and the imidazolyl is in the R-configuration, or its hydrochloride salt;

$R^3$ is methyl, $R^4$ and $R^7$ are each hydrogen, $R^5$ and $R^8$ are each n-butyl and the imidazolyl is in the R-configuration;

$R^3$, $R^4$ and $R^7$ are each hydrogen, $R^5$ and $R^8$ are together and the imidazolyl is in the R-configuration, or its hydrochloride salt;

$R^3$ and $R^4$ are each hydrogen, $R^7$ is 6-O—$CH_2$-phenyl, $R^5$ and $R^8$ are each n-butyl and the imidazolyl is a racemic mixture of the S- and R-configurations;

$R^3$, $R^4$ and $R^7$ are each hydrogen, $R^5$ and $R^8$ are together and the imidazolyl is in the R-configuration, or its hydrochloride salt;

$R^3$, $R^4$ and $R^7$ are each hydrogen, $R^5$ and $R^8$ are together and the imidazolyl is in the R-configuration;

$R^3$ and $R^7$ are each hydrogen, $R^4$ is methyl, $R^5$ and $R^8$ are each n-butyl and the imidazolyl is in the R-configuration;

$R^3$, $R^4$ and are each hydrogen, $R^7$ is 7-fluoro, $R^5$ and $R^8$ are each n-pentyl and the imidazolyl is the racemic mixture of the S- and R-configurations;

$R^3$, $R^4$ and $R^7$ are each hydrogen, $R^5$ and $R^8$ are each n-hexyl and the imidazolyl is in the R-configuration;

R³, R⁴ and R⁷ are each hydrogen, R⁵ is hydrogen and R⁸ is hexyl in the S-configuration and the imidazolyl is in the R-configuration, or its fumarate salt;

R³, R⁴ and R⁷ are each hydrogen, R⁵ and R⁸ are each n-butyl and the imidazolyl is in the R-configuration, or its fumarate salt;

R³, R⁴ and R⁷ are each hydrogen, R⁵ and R⁸ are together

and the imidazolyl is in the R-configuration;

R³, R⁴ and R⁷ are each hydrogen, R⁵ and R⁸ are each n-butyl and the imidazolyl is in the S-configuration;

R³, R⁴ and R⁷ are each hydrogen, R⁵ and R⁸ are each ethyl and the imidazolyl is in the R-configuration;

R³, R⁴ and R⁷ are each hydrogen, R⁵ and R⁸ are each n-pentyl and the imidazolyl is in the R-configuration;

R³, R⁴ and R⁷ are each hydrogen, R⁵ is methyl and R⁸ is cyclohexyl and the imidazolyl is in the R-configuration;

R³ and R⁴ are each hydrogen, R⁷ is 6-methyl R⁵ and R⁸ are each n-butyl and the imidazolyl is a racemic mixture of the S- and R-configurations;

R³ and R⁴ are each hydrogen, R⁷ is 7-fluoro, R⁵ and R⁸ are each n-butyl and the imidazolyl is a racemic mixture of the S- and R-configurations;

R³ and R⁴ are each hydrogen, R⁷ is 6-methoxy, R⁵ and R⁸ are each n-butyl and the imidazolyl is a racemic mixture of the S- and R-configurations;

R³ and R⁴ are each hydrogen, R⁷ is 6-hydroxy, R⁵ and R⁸ are each n-butyl and the imidazolyl is a racemic mixture of the S- and R-configurations;

R³ and R⁴ are each hydrogen, R⁷ is 6-fluoro, R⁵ and R⁸ are each n-butyl and the imidazolyl is a racemic mixture of the S- and R-configurations, or its hydrochloride salt;

R³ and R⁴ are each hydrogen, R⁷ is 8-methyl, R⁵ and R⁸ are each n-butyl and the imidazolyl is a racemic mixture of the S- and R-configurations;

R³ and R⁴ are each hydrogen, R⁷ is 6-methyl, R⁵ and R⁸ are each n-pentyl and the imidazolyl is a racemic mixture of the S- and R-configurations; or R³ and R⁴ are each hydrogen, R⁷ is 6-chloro, R⁵ and R⁸ are each n-butyl and the imidazolyl is a racemic mixture of the S- and R-configurations.

4. A compound according to claim 3 wherein said compound is selected from the group consisting of R³, R⁴ and R⁷ are each hydrogen, R⁵ is hydrogen and R⁸ is hexyl in the S-configuration and the imidazolyl is in the R-configuration, or its fumarate salt;

R³, R⁴ and R⁷ are each hydrogen, R⁵ and R⁸ are each n-butyl and the imidazolyl is in the R-configuration, or its fumarate salt;

R³, R⁴ and R⁷ are each hydrogen, R⁵ and R⁸ are together

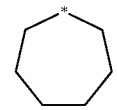

and the imidazolyl is in the R-configuration;

R³, R⁴ and R⁷ are each hydrogen, R⁵ and R⁸ are each n-butyl and the imidazolyl is in the S-configuration;

R³, R⁴ and R⁷ are each hydrogen, R⁵ and R⁸ are each ethyl and the imidazolyl is in the R-configuration;

R³, R⁴ and R⁷ are each hydrogen, R⁵ and R⁸ are each n-pentyl and the imidazolyl is in the R-configuration;

R³, R⁴ and R⁷ are each hydrogen, R⁵ is methyl and R⁸ is cyclohexyl and the imidazolyl is in the R-configuration;

R³ and R⁴ are each hydrogen, R⁷ is 6-methyl R⁵ and R⁸ are each n-butyl and the imidazolyl is a racemic mixture of the S- and R-configurations;

R³ and R⁴ are each hydrogen, R⁷ is 7-fluoro, R⁵ and R⁸ are each n-butyl and the imidazolyl is a racemic mixture of the S- and R-configurations;

R³ and R⁴ are each hydrogen, R⁷ is 6-methoxy, R⁵ and R⁸ are each n-butyl and the imidazolyl is a racemic mixture of the S- and R-configurations;

R³ and R⁴ are each hydrogen, R⁷ is 6-hydroxy, R⁵ and R⁸ are each n-butyl and the imidazolyl is a racemic mixture of the S- and R-configurations;

R³ and R⁴ are each hydrogen, R⁷ is 6-fluoro, R⁵ and R⁸ are each n-butyl and the imidazolyl is a racemic mixture of the S- and R-configurations, or its hydrochloride salt;

R³ and R⁴ are each hydrogen, R⁷ is 8-methyl, R⁵ and R⁸ are each n-butyl and the imidamolyl is a racemic mixture of the S- and R-configurations;

R³ and R⁴ are each hydrogen, R⁷ is 6-methyl, R⁵ and R⁸ are each n-pentyl and the imidazolyl is a racemic mixture of the S- and R-configurations; and R³ and R⁴ are each hydrogen, R⁷ is 6-chloro, R⁵ and R⁸ are each n-butyl and the imidazolyl is a racemic mixture of the S- and R-configurations.

5. A pharmaceutical composition comprising a compound according to claim 1 or a pharmaceutically acceptable salt thereof and a pharmaceutically acceptable carrier.

6. A method of treating diarrhea in a subject in need thereof, which comprises administering a compound according to claim 1 or a pharmaceutically acceptable salt thereof to said subject.

7. A method of treating diabetes mellitus, enterocutaneous and pancreaticocutaneous fistula, Dumping syndrome, watery diarrhea syndrome, or inflammatory disorders in a subject in need thereof, which comprises administering a compound according to claim 1 or a pharmaceutically acceptable salt thereof to said subject.

8. The method according to claims 6, wherein said diarrhea comprises AIDS related diarrhea or chemotherapy related diarrhea.

* * * * *